(12) United States Patent
Bushell et al.

(10) Patent No.: US 9,492,496 B2
(45) Date of Patent: Nov. 15, 2016

(54) AMINOTHIAZOLES AND THEIR USES

(71) Applicants: Simon Bushell, Boston, MA (US); Matthew J. Lamarche, Reading, MA (US); Jennifer Leeds, Arlington, MA (US); Lewis Whitehead, Swampscott, MA (US)

(72) Inventors: Simon Bushell, Boston, MA (US); Matthew J. Lamarche, Reading, MA (US); Jennifer Leeds, Arlington, MA (US); Lewis Whitehead, Swampscott, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/291,572

(22) Filed: May 30, 2014

(65) Prior Publication Data

US 2014/0274878 A1    Sep. 18, 2014

Related U.S. Application Data

(63) Continuation of application No. 13/864,779, filed on Apr. 17, 2013, now abandoned, which is a continuation of application No. 12/333,602, filed on Dec. 12, 2008, now Pat. No. 8,426,356.

(60) Provisional application No. 61/024,709, filed on Jan. 30, 2008, provisional application No. 61/013,122, filed on Dec. 12, 2007.

(51) Int. Cl.
| | | |
|---|---|---|
| C07D 417/04 | (2006.01) |
| A61K 38/05 | (2006.01) |
| A61K 45/06 | (2006.01) |
| C07K 5/078 | (2006.01) |

(52) U.S. Cl.
CPC .............. *A61K 38/05* (2013.01); *A61K 45/06* (2013.01); *C07D 417/04* (2013.01); *C07K 5/06139* (2013.01)

(58) Field of Classification Search
None
See application file for complete search history.

(56) References Cited

U.S. PATENT DOCUMENTS

| | | |
|---|---|---|
| 5,139,778 A | 8/1992 | Selva et al. |
| 5,202,241 A | 4/1993 | Selva et al. |
| 5,322,777 A | 6/1994 | Selva et al. |
| 5,514,649 A | 5/1996 | Selva et al. |
| 5,547,666 A | 8/1996 | Selva et al. |
| 5,599,791 A | 2/1997 | Tavecchia et al. |
| 5,747,295 A | 5/1998 | Selva et al. |
| 5,843,890 A | 12/1998 | Selva et al. |
| 5,882,900 A | 3/1999 | Rizzo et al. |
| 5,891,869 A | 4/1999 | Lociuro et al. |
| 6,008,225 A | 12/1999 | Lociuro et al. |
| 6,143,739 A | 11/2000 | Lociuro et al. |
| 7,851,439 B2* | 12/2010 | Bushell ............. C07K 5/06139 424/116 |
| 2008/0221142 A1 | 9/2008 | LaMarch et al. |
| 2010/0267757 A1 | 10/2010 | LaMarch et al. |

FOREIGN PATENT DOCUMENTS

| | | |
|---|---|---|
| EP | 494078 | 7/1992 |
| EP | 675900 | 2/1998 |
| EP | 825194 | 2/1998 |
| WO | WO 96/14427 | 5/1996 |
| WO | WO 03/105881 | 12/2003 |
| WO | WO 2006/086012 | 8/2006 |
| WO | WO 2007/007399 | 1/2007 |
| WO | WO 2007/142986 | 12/2007 |
| WO | WO 2008/082562 | 7/2008 |
| WO | WO 2008/148754 | 12/2008 |

OTHER PUBLICATIONS

Clough et al, *Bioorganic and Medicinal Chemistry Letters* 13(20):3409-3414.

Selva et al.,"C omponents of the GE2270 Complex Produced by Planobispora Rosea ATCC 53773" *Journal of Antibiotics*, Japan Antibiotics Research Association, Tokyo, JP 48(9):1039-1042, Sep. 1, 1995.

(Continued)

*Primary Examiner* — James H Alstrum Acevedo
*Assistant Examiner* — Roy Teller
(74) *Attorney, Agent, or Firm* — Michael G. Smith

(57) ABSTRACT

The present application describes organic compounds of Formula (I)

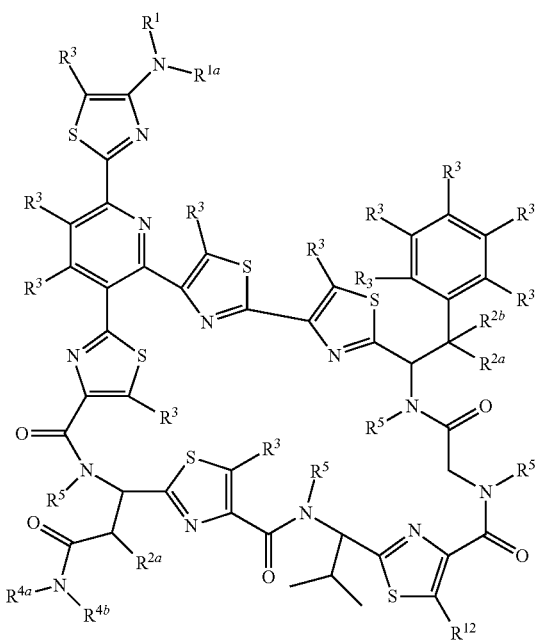

and pharmaceutical compositions thereof, and their use for the treatment, prevention and/or amelioration of diseases, particularly bacterial infections.

14 Claims, No Drawings

(56) References Cited

OTHER PUBLICATIONS

Sussmuth "Vancomycin Resistance: Small Molecule Approaches Targeting the Bacterial Cell Wall Biosynthesis" *Chembiochem* 3:295-298, 2002.

Tavecchia et al., "Degradation Studies of Antibiotic MDL 62,879 (GE2270A) and Revision of the Structure" *Tetrahedron* 51(16):4867-4890, 1995 Great Britain.

Selva et al., "Antibiotic GE2270 A: A Novel Inhibitor of Bacterial Protein Synthesis. I. Isolation and Characterization" *Journal of Antibiotics* 44(7):693-701, 1991.

LaMarche, "Discovery of LFF571: An Investigational Agent for Clostridium Difficile Infection" *Journal of Medicinal Chemistry* 55:2376-2387, 2012.

Atropisomer from http://www.allwords.com/word-atropisomer.html; pp. 1. [Accessed Jul. 23, 2009].

Bacterial Infection (Types of); Merck Manual; http://www.merck.com/mmhe/sec17/ch190/ch190a.html;pp. 1-5; Accessed Apr. 16, 2009].

Cislak, "Pyridine-N-Oxide" *Industrial and Engineering Chemistry* 47(4):800-802, 1955.

Diastereoisomer from http://www.allwords.com/word-diastereoisomer. Html; pp. 1 (Accessed Jul. 23, 2009].

Enantiomer from http://www.chemicool.com/definition/enantiomer. Html; pp. 1 [Accessed Jul. 23, 2009].

Kirromycin (Structure of) (K1507); SIGMA.com; pp. 1 [Accessed Apr. 16, 2009].

Pyridine N-Oxide; Sigma.com; pp. 1-6 [Accessed Jul. 23, 2009].

Racemate from http://www.chemicool.com/definition/racemate.html; pp. 1 [Access Jul. 23, 2009].

Residue (Definition of) from http://dictionary reference.com/browse/residue; pp. 1.3 [Accessed Jul. 13, 2009].

Rotamer from http;1 fll fll.chemicool.com/definition/rotamer.html; pp. 1 [Accessed Jul. 23, 2009].

Stereoisomers from http://www.chemicool.com/definition/stereoisomers.html; pp. 1-2 [Accessed Jul. 23, 2009].

Tautomer from http://medical-dictionary.thefreedictionary.com/tautomer; pp. 1-2 [Accessed Jul. 23, 2009].

Wolf et al., "Kirromycin, an Inhibitor of Protein Biosynthesis that Acts on Elongation Factor Tu", *Proceedings of National Academy of Sciences USA*: 71(12):4910-4914, 1974.

* cited by examiner

AMINOTHIAZOLES AND THEIR USES

CROSS-REFERENCE TO RELATED APPLICATIONS

This application is a continuation application of U.S. Ser. No. 13/864,779, filed Apr. 17, 2013, which is a continuation application of U.S. Ser. No. 12/333,602, filed Dec. 12, 2008, which issued as U.S. Pat. No. 8,426,356, which claims the benefit of priority to U.S. Provisional Application No. 61/024,709, filed Jan. 30, 2008, and U.S. Provisional Application No. 61/013,122, filed Dec. 12, 2007, the contents of which are incorporated herein by reference.

BACKGROUND

Since the discovery of penicillin, pharmaceutical companies have produced a number of antibacterial agents to combat a wide variety of bacterial infections. In the past several years, there has been rapid emergence of bacterial resistance to several of these antibiotics. The multidrug resistance among these bacterial pathogens may also be due to mutation leading to more virulent clinical isolation. Perhaps the most disturbing occurrence has been the acquisition of resistance to vancomycin, an antibiotic generally regarded as the agent of last resort for serious Gram-positive infections.

This is true especially of some Gram-positive pathogen groups, such as staphylococci, pneumococci and enterococci (S. Ewig et al.; Antibiotika-Resistenz bei Erregern ambulant erworbener Atemwegsinfektionen (Antibiotic resistance in pathogens of outpatient-acquired respiratory tract infections); Chemother. J. 2002, 11, 12-26; F. Tenover; Development and spread of bacterial resistance to antimicrobial agents: an overview; Clin. Infect. Dis. 2001 Sep. 15, 33 Suppl. 3, 108-115) as well as *Staphylococcus, Streptococcus, Mycobacterium, Enterococcus, Corynebacterium, Borrelia, Bacillus, Chlamydia, Mycoplasma*, and the like.

A problem of equally large dimension is the increasing incidence of the more virulent, methicillin-resistant *Staphylococcus aureas* (MRSA) among clinical isolates found worldwide. As with vancomycin resistant organisms, many MRSA strains are resistant to most of the known antibiotics, but MRSA strains have remained sensitive to vancomycin. However, in view of the increasing reports of vancomycin resistant clinical isolates and growing problem of bacterial resistance, there is an urgent need for new molecular entities effective against the emerging and currently problematic Gram-positive organisms.

This growing multidrug resistance has recently rekindled interest in the search for new structural classes of antibiotics that inhibit or kill these bacteria.

SUMMARY OF THE INVENTION

There remains a need for new treatments and therapies for bacterial infections. There is also a need for compounds useful in the treatment or prevention or amelioration of one or more symptoms of bacterial infections. Furthermore, there is a need for methods for modulating the activity of the elongation factor EF-Tu, using the compounds provided herein.

In one aspect, the invention provides a compound of formula I:

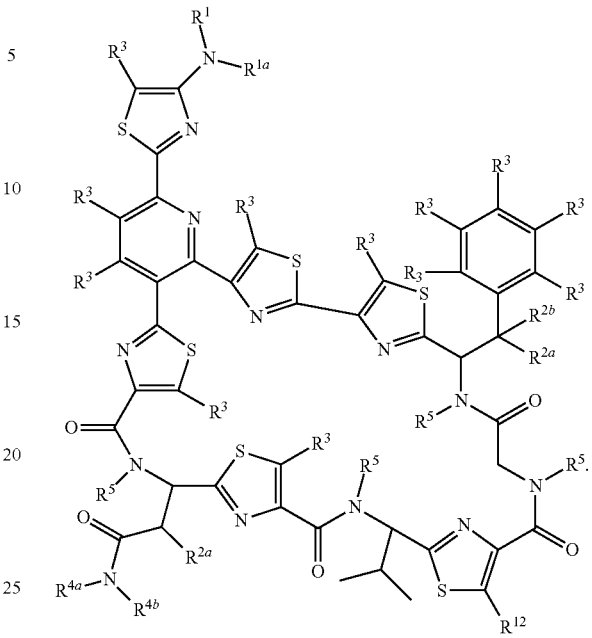

I

In another aspect, the invention provides a method of treating a bacterial infection wherein the treatment includes administering to a subject in need thereof a pharmaceutically acceptable amount of a compound of formula I, II, III, IV, V, or VI, such that the bacterial infection is treated.

In another aspect, the invention provides a method of treating an EF-Tu associated-state wherein the treatment includes administering to a subject in need thereof a pharmaceutically acceptable amount of a compound of formula I, II, III, IV, V, or VI, such that the EF-Tu associated state is treated.

In still another aspect, the invention provides a method of treating, inhibiting or preventing the activity of EF-Tu in a subject in need thereof, which includes administering to the subject a pharmaceutically acceptable amount of a compound of formula I, II, III, IV, V, or VI. In one embodiment, a bacterial infection is treated in a subject in need thereof.

In another aspect, the invention provides a method of treating, inhibiting or preventing the activity of bacteria in a subject in need thereof, which includes administering to the subject a pharmaceutically acceptable amount of a compound of formula I, II, III, IV, V, or VI, wherein the compound interacts with any target in the life cycle of the bacteria. In one embodiment, the target is EF-Tu.

In another aspect, the invention provides a method of treating a bacterial infection in a subject, wherein the treatment includes administering to a subject in need thereof a pharmaceutically acceptable amount of a compound of the formula I, II, III, IV, V, or VI, and a pharmaceutically acceptable carrier, such that the bacterial infection is treated.

In still another aspect, the invention provides a method of treating a bacterial infection wherein the treatment includes administering to a subject in need thereof a pharmaceutically effective amount of a compound of the formula I, II, III, IV, V, or VI, in combination with a pharmaceutically effective amount of an additional therapeutic agent, such that the bacterial infection is treated. In one embodiment, the compound of the formula I, II, III, IV, V, or VI and the other pharmaceutical agent are administered as part of the same pharmaceutical composition. In another embodiment, the compound of the formula I, II, III, IV, V, or VI and the other therapeutic agent are administered as separate pharmaceutical compositions, and the compound is administered prior to, at the same time as, or following administration of the other agent.

In another aspect, the invention provides a packaged bacterial infection treatment, comprised of formula I, II, III, IV, V, or VI, packaged with instructions for using an effective amount of the compound to treat a bacterial infection.

In another aspect, the invention provides a method of treating acne in subject in need thereof, wherein the treatment includes administering to the subject a pharmaceutically acceptable amount of a compound of formula I, II, III, IV, V, or VI.

In yet another aspect, the invention provides a pharmaceutical composition which includes a compound of formula I, II, III, IV, V, or VI, and at least one pharmaceutically acceptable carrier or diluent.

DETAILED DESCRIPTION OF THE INVENTION

This invention is directed to compounds, e.g., thiopeptide compounds, and intermediates thereto, as well as pharmaceutical compositions containing the compounds for use in treatment of bacterial infection. This invention is also directed to the compounds of the invention or compositions thereof as modulators of the elongation factor EF-Tu. The compounds are particularly useful in interfering with the life cycle of bacteria and in treating or preventing a bacterial infection or physiological conditions associated therewith. The present invention is also directed to methods of combination therapy for inhibiting EF-Tu activity in cells, or for treating or preventing a bacterial infection in patients using the compounds of the invention or pharmaceutical compositions, or kits thereof.

In one aspect, the invention provides compounds of the formula I:

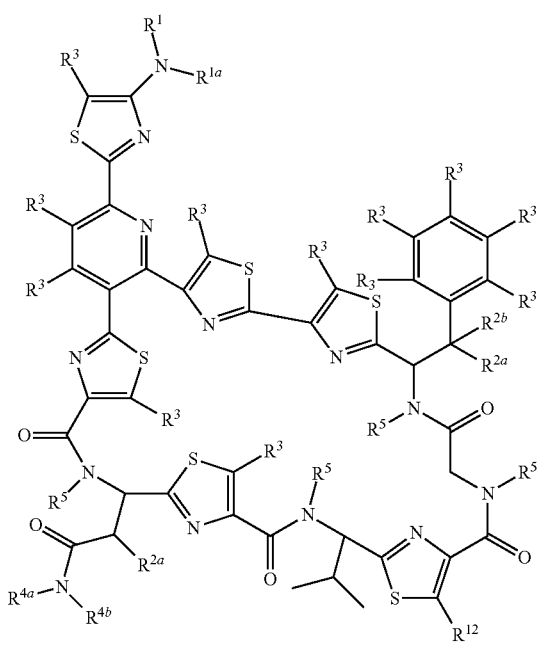

I and pharmaceutically acceptable salts, enantiomers, stereoisomers, rotamers, tautomers, diastereomers, atropisomers or racemates thereof, including the pyridine N-oxide thereof;

wherein $R^1$ is —Z—$CO_2$H and -A-Z—$CO_2$H;

$R^{1a}$ is hydrogen, —Z—$CO_2$H, and -A-Z—$CO_2$H, wherein if $R^{1a}$ is hydrogen, then the Z residue of $R^1$ is substituted by at least two $CO_2$H groups; or $R^1$ and $R^{1a}$, taken in combination, form a saturated, partially unsaturated or aromatic heterocycle having 4 to 7 ring atoms and having 0-3 additional ring heteroatoms selected from N, O and S, wherein the heterocycle is substituted by at least two residues independently selected from $CO_2$H, —Z—$CO_2$H, and -A-Z—$CO_2$H;

A is independently selected at each occurrence from the group consisting of a —C(O)—, —C(O)O—, —C(O)N($R^{8a}$)—, —S(O)$_2$—, —S(O)—, —C(H)=N—, —S(O)$_2$N($R^{8a}$)—, and —S(O)N($R^{8a}$)—;

Z is $C_1$-$C_{10}$alkylene, $C_3$-$C_8$cycloalkylene, $C_3$-$C_8$heterocycloalkylene, phenylene, or 5-6 membered heteroarylene, each of which is optionally substituted with one or more groups independently selected from $C_1$-$C_4$alkyl, $C_1$-$C_4$alkoxy, hydroxy, amino, mono- and di-$C_1$-$C_6$alkylamino, C(O)OH, or halogen;

$R^{2a}$ is selected from the group consisting of H, substituted or unsubstituted alkyl, OH, $OR^{4a}$, $OC(O)R^{4a}$, $OC(O)N(R^{8a})_2$ and $N(R^{8a})_2$;

$R^{2b}$ is selected from the group consisting of absent, H and alkyl, or $R^{2a}$ and $R^{2b}$ may together form =O or =NH;

$R^3$ an $R^{12}$ are each, independently, selected from the group consisting of H, halogen, $OR^{4b}$, -A-J, and $N(R^{8a})_2$;

$R^{4a}$ is selected from the group consisting of H, and alkyl;

$R^{4b}$ is selected from the group consisting of alkyl and —(CH$_2$—CH$_2$—O—)$_n$—$R^9$, wherein n is an integer of 1-500, 1,000, 2,000, 3,000, 4,000, 5,000, 10,000, 20,000, 30,000, 40,000, 50,000, or 60,000 or is a mean of a plurality of integers having a value of 1-500, 1,000, 2,000, 3,000, 4,000, 5,000, 10,000, 20,000, 30,000, 40,000, 50,000, or 60,000;

$R^5$ is selected from the group consisting of H, alkyl, and $R^{4b}$;

J is selected from the group consisting of H, F, O-alkyl, $N(R^{8a})_2$, $N^+(R^{8a})_3$, $N(R^{8a})C(O)$alkyl, $CO_2$H, C(=O)N($R^{8a})_2$, $CO_2$-alkyl, P(O)(OH)$_2$, P(O)(O-alkyl)$_2$, and a substituted nitrogen-containing heterocycle;

$R^{8a}$ is absent, or selected from the group consisting of H, -(alkyl)-, -(cycloalkyl)-, C(alkyl)$_2$-J, —$R^{4b}$, wherein $R^{8a}$ can also cyclize with the atom to which $R^{8a}$ is bonded to form a 3, 4, 5, 6 or 7-membered ring that is aromatic or non-aromatic and may contain one or more heteroatoms, wherein the ring may be further substituted one or more times with substituents that are the same or different; and $R^9$ is selected from the group consisting of H, alkyl and CH$_2$CO$_2$H.

Certain compounds of formula I provided herein include compounds of formula II and formula III:

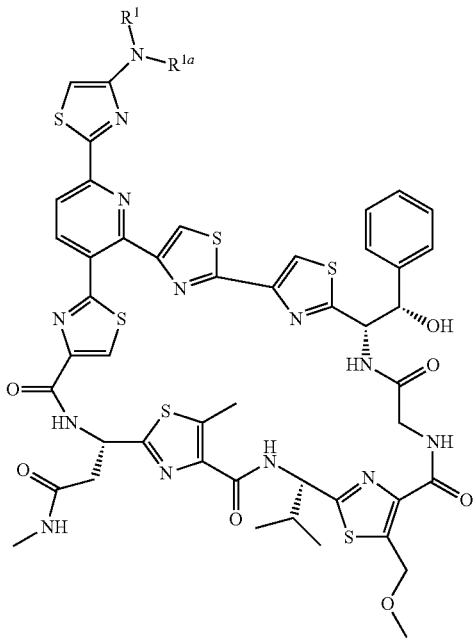

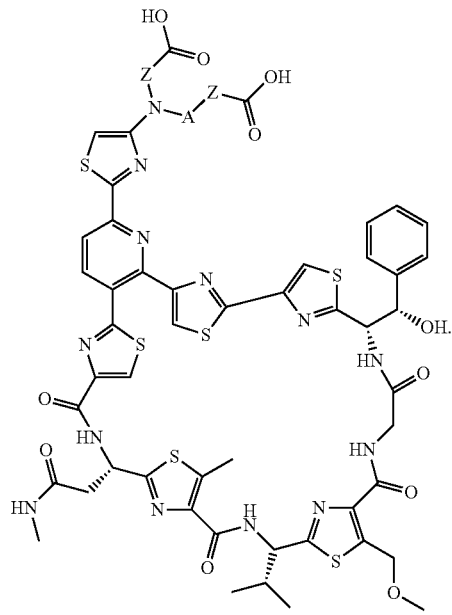

Certain compounds of formula I include those compounds represented by formula V:

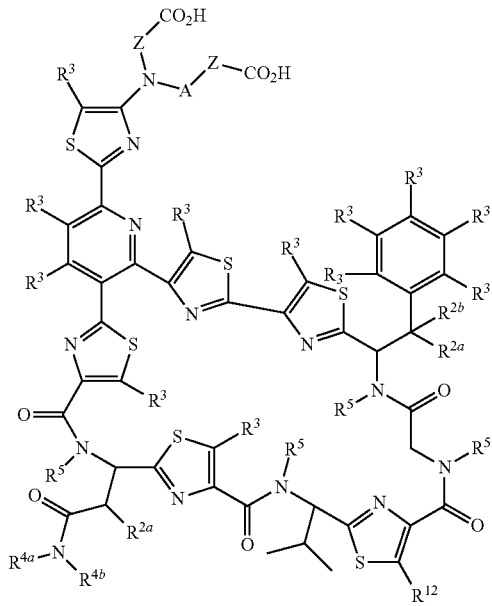

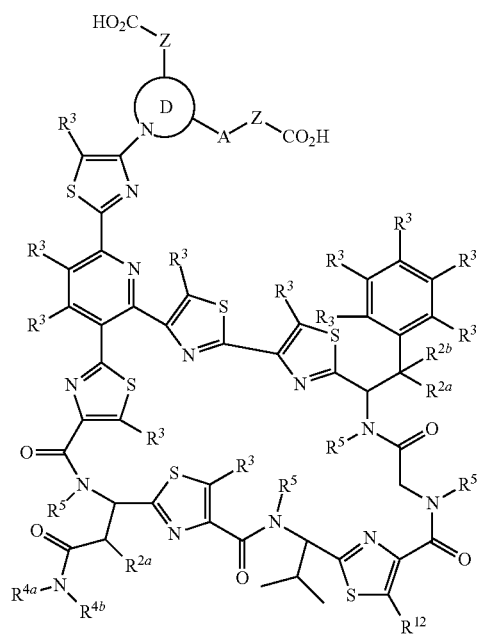

and pharmaceutically acceptable salts, enantiomers, stereoisomers, rotamers, tautomers, diastereomers, atropisomers or racemates thereof, including the pyridine N-oxide thereof.

Certain compounds of formula III include those compounds represented by formula IV:

and pharmaceutically acceptable salts, enantiomers, stereoisomers, rotamers, tautomers, diastereomers, atropisomers or racemates thereof, including the pyridine N-oxide thereof, wherein D represents a five or six membered heterocyclic ring which is saturated or aromatic, which ring comprises 0-2 additional ring heteroatoms selected from N, O or S.

Certain compounds of formula IV include those compounds represented by formula V-a:

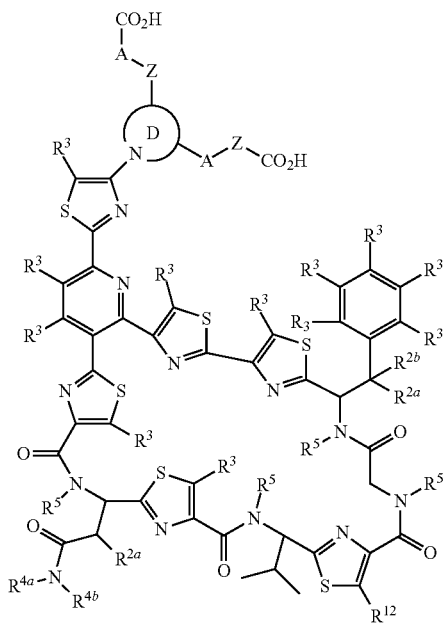

V-a and pharmaceutically acceptable salts, enantiomers, stereoisomers, rotamers, tautomers, diastereomers, atropisomers or racemates thereof, including the pyridine N-oxide thereof, wherein D represents a five or six membered heterocyclic ring which is saturated or aromatic, which ring comprises 0-2 additional ring heteroatoms selected from N, O or S.

Certain preferred compounds of Formula I, III, or V include those compounds in which $R^{2b}$, $R^{4b}$ and $R^5$ are H, and $R^{4a}$ is $CH_3$. Other preferred compounds of Formula I include those compounds in which $R^{2b}$, $R^{4b}$ and $R^5$ are H, $R^{4a}$ is $CH_3$, and $R^{12}$ is $CH_2$—O—$CH_3$.

Certain compounds of formula V include those compounds represented by formula VI:

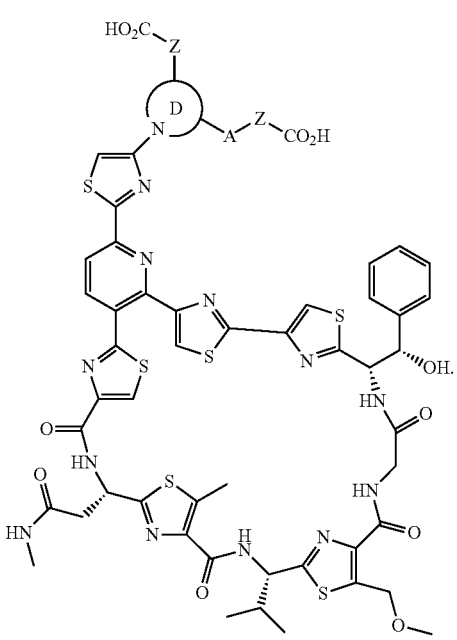

VI

Certain compounds of formula I include those compounds represented by formula VI-a:

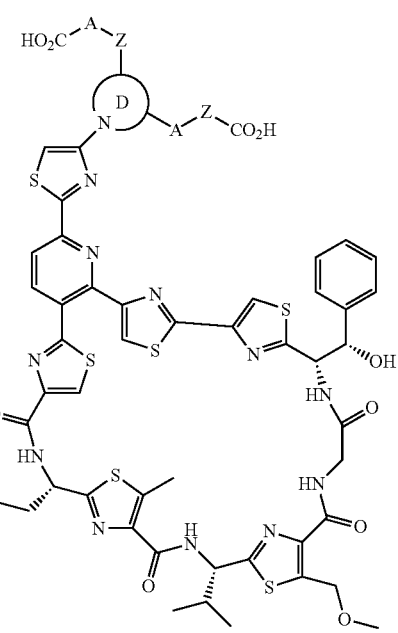

VI-a and pharmaceutically acceptable salts, enantiomers, stereoisomers, rotamers, tautomers, diastereomers, atropisomers or racemates thereof, including the pyridine N-oxide thereof, wherein D represents a five or six membered heterocyclic ring which is saturated or aromatic, which ring comprises 0-2 additional ring heteroatoms selected from N, O or S.

Certain preferred compounds of Formula III, IV, V, V-a, VI, VI-a include those compounds in which A is selected from the group consisting of —C(O)O—, C(O)—NH—, —C(O)—, —S(O)$_2$—, and —S(O)$_2$NH—; and Z is independently selected at each occurrence from the group consisting of $C_1$-$C_{10}$alkylene,

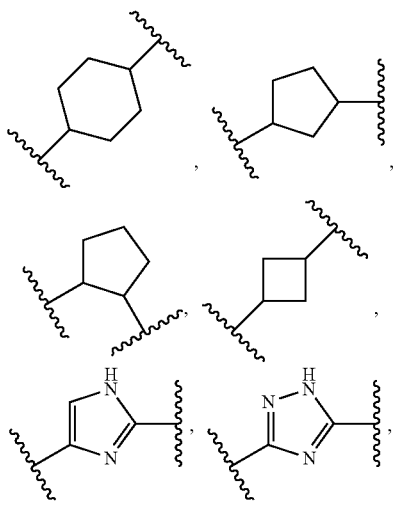

-continued

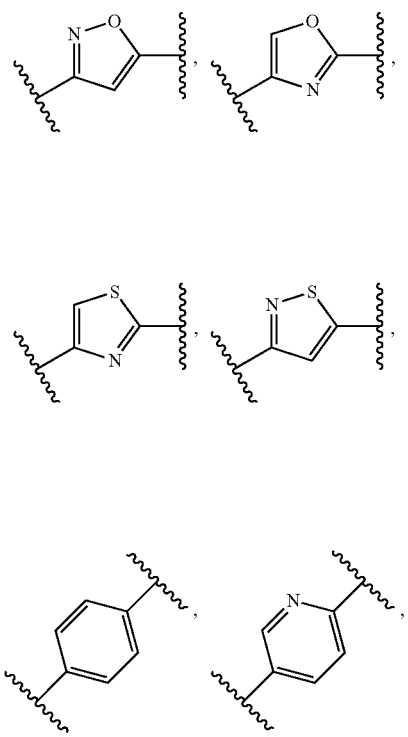

Still other compounds of formula I provided herein include those compounds in which $R^{2a}$ is OH or OAC.

Yet other compounds of formula I provided herein include those compounds in which the core pyridine functionality is of the following N-oxide formula:

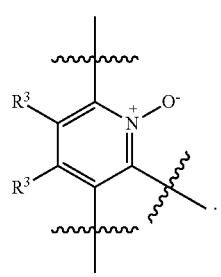

In yet another aspect, the invention provides compounds of the formula VII:

VII

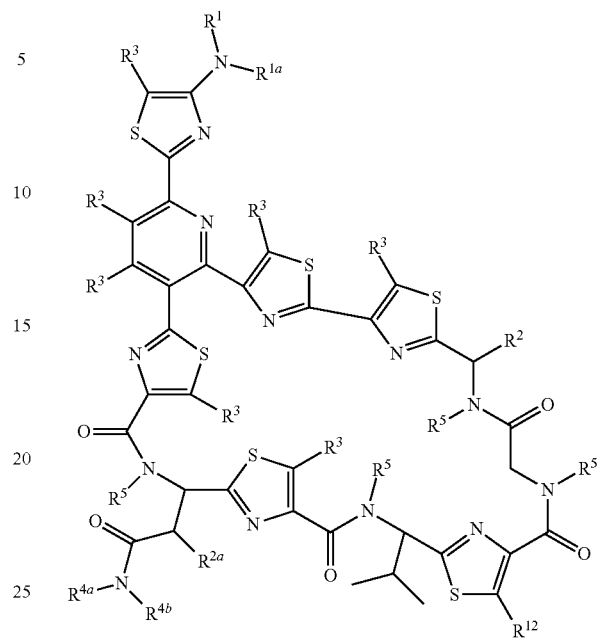

and pharmaceutically acceptable salts, enantiomers, stereoisomers, rotamers, tautomers, diastereomers, atropisomers or racemates thereof, including the pyridine N-oxide thereof;

wherein $R^1$ is —Z—CO$_2$H and -A-Z—CO$_2$H;

$R^{1a}$ is hydrogen, —Z—CO$_2$H, and -A-Z—CO$_2$H, wherein if $R^{1a}$ is hydrogen, then the Z residue of $R^1$ is substituted by at least two CO$_2$H groups; or $R^1$ and $R^{1a}$, taken in combination, form a saturated, partially unsaturated or aromatic heterocycle having 4 to 7 ring atoms and having 0-3 additional ring heteroatoms selected from N, O and S, wherein the heterocycle is substituted by at least two residues independently selected from CO$_2$H, —Z—CO$_2$H, and -A-Z—CO$_2$H;

A is independently selected at each occurrence from the group consisting of a —C(O)—, —C(O)O—, —C(O)N(R$^{8a}$)—, —S(O)$_2$—, —S(O)—, —C(H)=N—, —S(O)$_2$N(R$^{8a}$)—, and —S(O)N(R$^{8a}$)—;

Z is C$_1$-C$_{10}$alkylene, C$_3$-C$_8$cycloalkylene, C$_3$-C$_8$heterocycloalkylene, phenylene, or 5-6 membered heteroarylene, each of which is optionally substituted with one or more groups independently selected from C$_1$-C$_4$alkyl, C$_1$-C$_4$alkoxy, hydroxy, amino, mono- and di-C$_1$-C$_6$alkylamino, C(O)OH, or halogen;

$R^2$ is hydrogen, C$_{1-6}$alkyl, hydroxyC$_{1-6}$alkyl, C$_{1-6}$alkoxyC$_{0-6}$alkyl, C$_{3-7}$cycloalkylC$_{0-4}$-alkyl, arylC$_{0-4}$alkyl, or a residue of the formula:

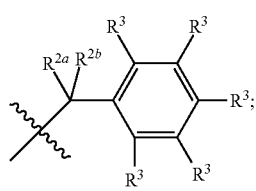

$R^{2a}$ is selected from the group consisting of H, substituted or unsubstituted alkyl, OH, $OR^{4a}$, $OC(O)R^{4a}$, $OC(O)N(R^{8a})_2$ and $N(R^{8a})_2$;

$R^{2b}$ is selected from the group consisting of absent, H and alkyl, or $R^{2a}$ and $R^{2b}$ may together form =O or =NH;

$R^3$ an $R^{12}$ are each, independently, selected from the group consisting of H, halogen, $OR^{4b}$, -A-J, and $N(R^{8a})_2$;

$R^{4a}$ is selected from the group consisting of H, and alkyl;

$R^{4b}$ is selected from the group consisting of alkyl and $-(CH_2-CH_2-O-)_n-R^9$, wherein n is an integer of 1-500, 1,000, 2,000, 3,000, 4,000, 5,000, 10,000, 20,000, 30,000, 40,000, 50,000, or 60,000 or is a mean of a plurality of integers having a value of 1-500, 1,000, 2,000, 3,000, 4,000, 5,000, 10,000, 20,000, 30,000, 40,000, 50,000, or 60,000;

$R^5$ is selected from the group consisting of H, alkyl, and $R^{4b}$;

J is selected from the group consisting of H, F, O-alkyl, $N(R^{8a})_2$, $N^+(R^{8a})_3$, $N(R^{8a})C(O)$alkyl, $CO_2H$, $C(=O)N(R^{8a})_2$, $CO_2$-alkyl, $P(O)(OH)_2$, $P(O)(O$-alkyl$)_2$, and a substituted nitrogen-containing heterocycle;

$R^{8a}$ is absent, or selected from the group consisting of H, -(alkyl)-, -(cycloalkyl)-, C(alkyl)$_2$-J, —$R^{4b}$, wherein $R^{8a}$ can also cyclize with the atom to which $R^{8a}$ is bonded to form a 3, 4, 5, 6 or 7-membered ring that is aromatic or non-aromatic and may contain one or more heteroatoms, wherein the ring may be further substituted one or more times with substitutents that are the same or different; and $R^9$ is selected from the group consisting of H, alkyl and $CH_2CO_2H$.

Preferred embodiments of the compounds of the invention (including pharmaceutically acceptable salts thereof, as well as enantiomers, stereoisomers, rotamers, tautomers, diastereomers, or racemates thereof) are shown below in Table A and Table B, and are also considered to be "compounds of the invention."

TABLE A

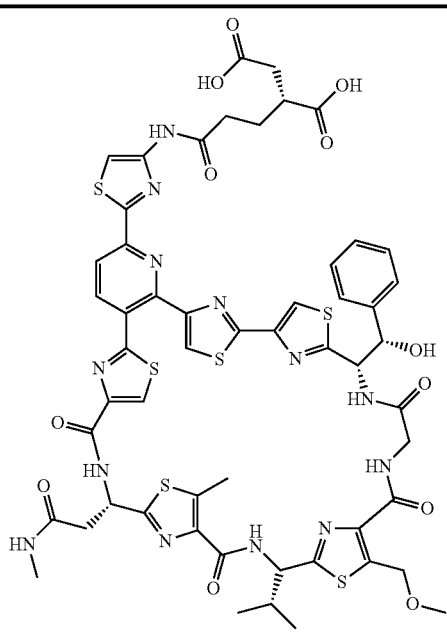

1.

TABLE A-continued

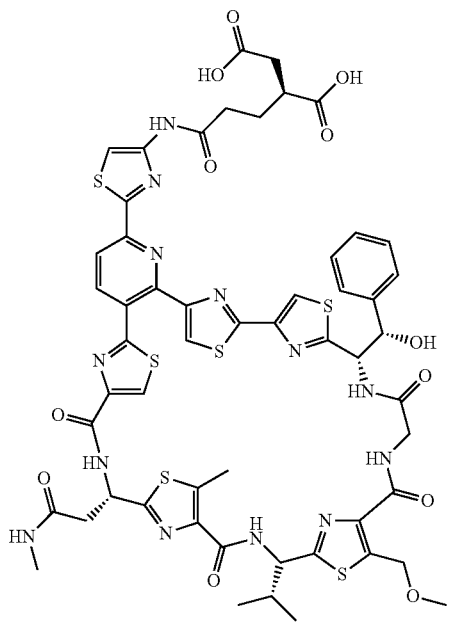

2.

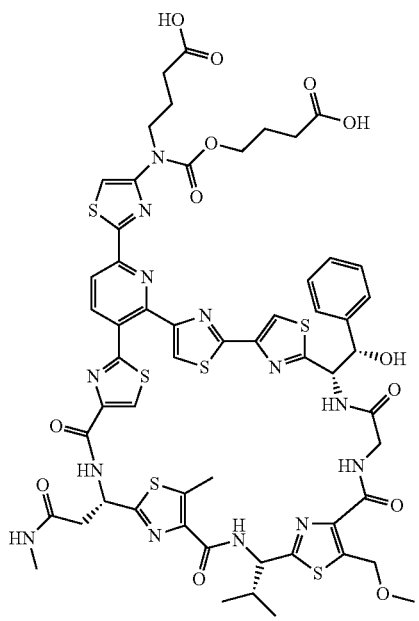

3.

TABLE A-continued
4.
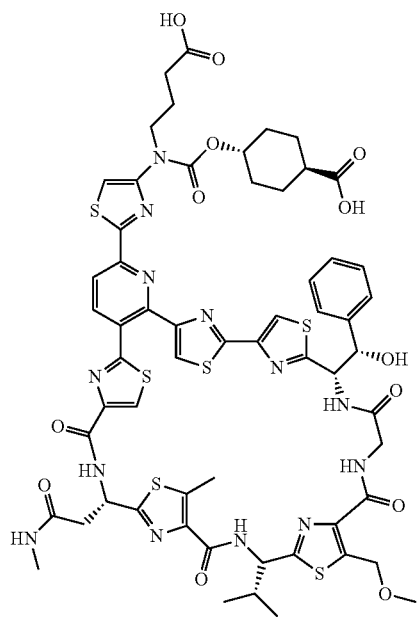
5.
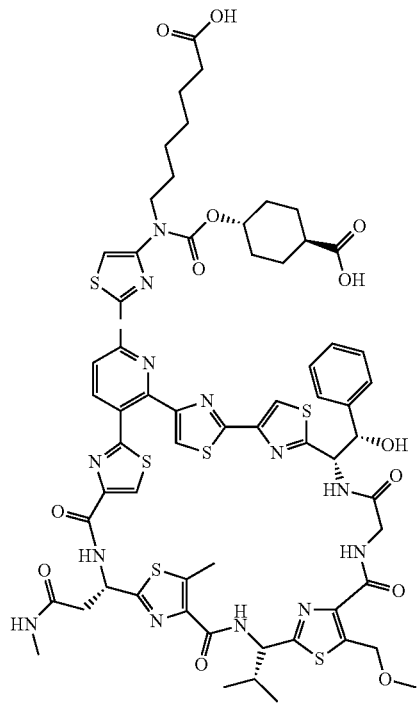
6.
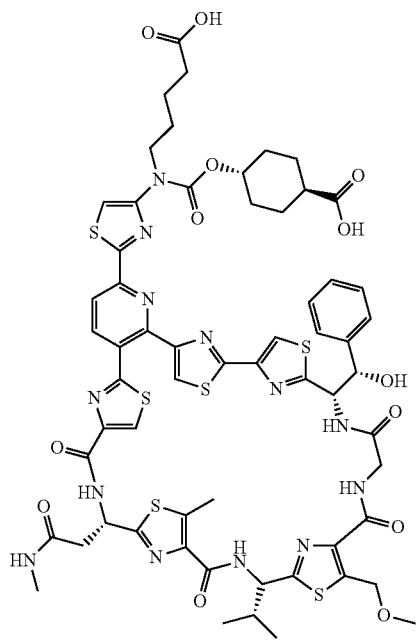
7.
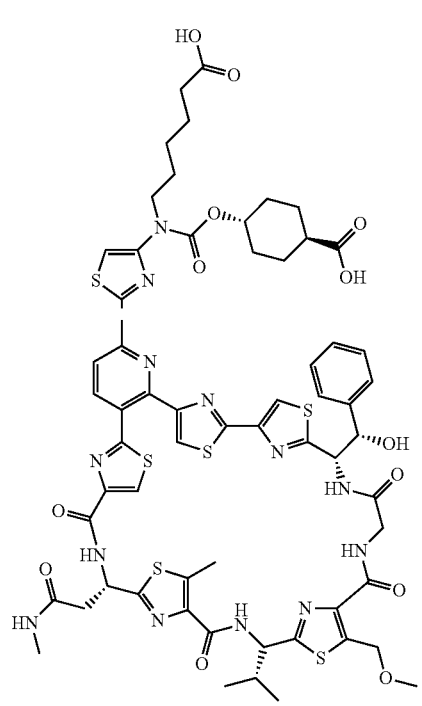

TABLE A-continued
8.
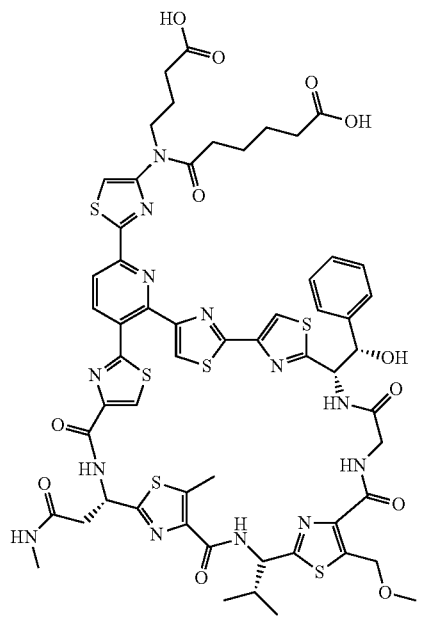
9.
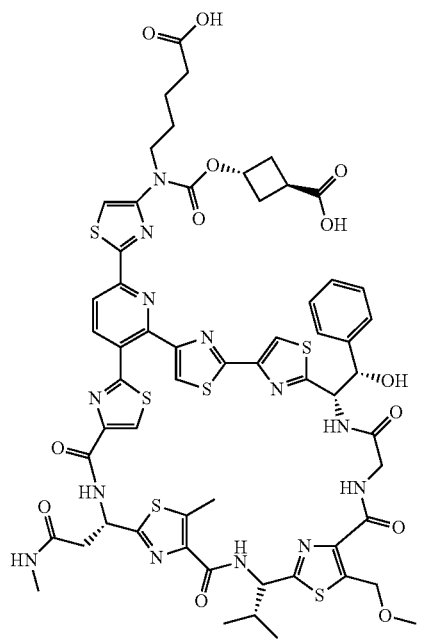
10.
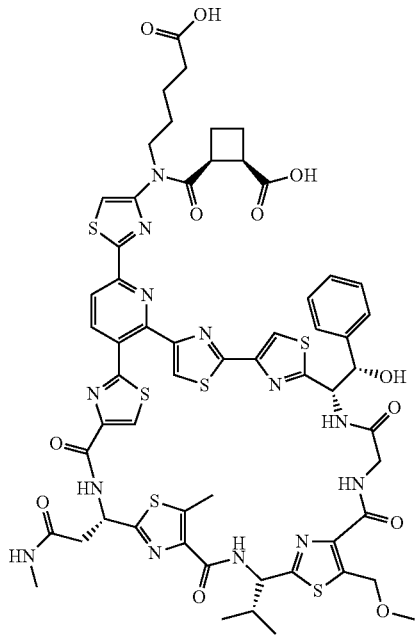
11.
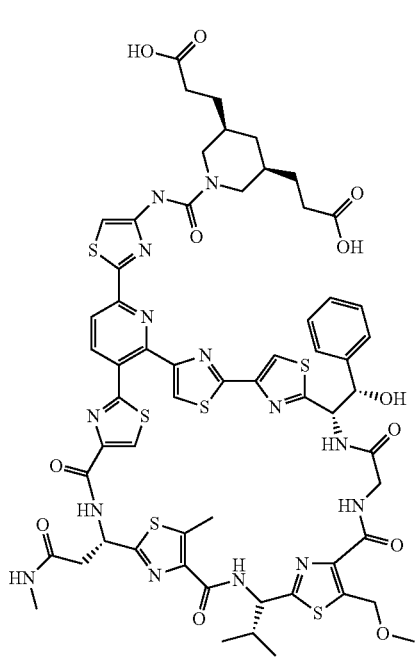

TABLE A-continued
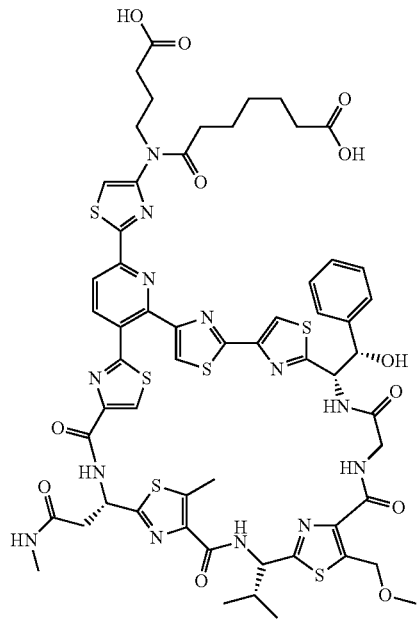
12.
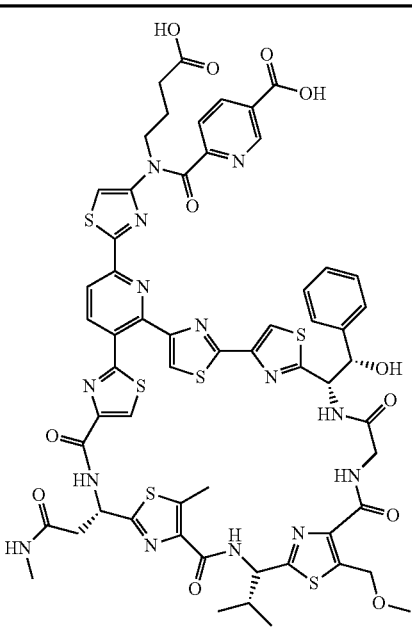
14.
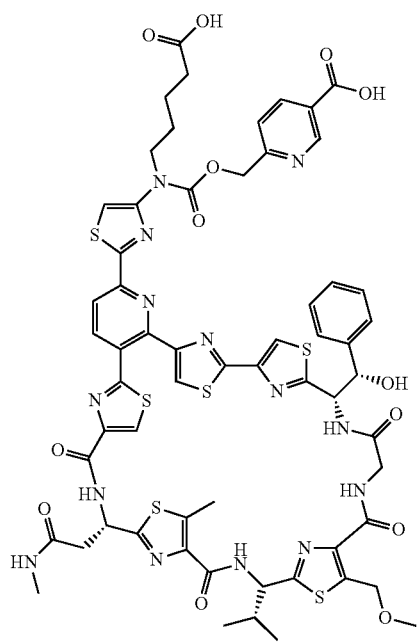
13.
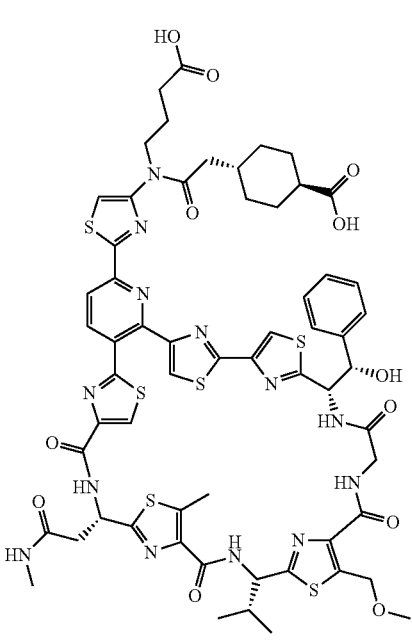
15.

TABLE A-continued
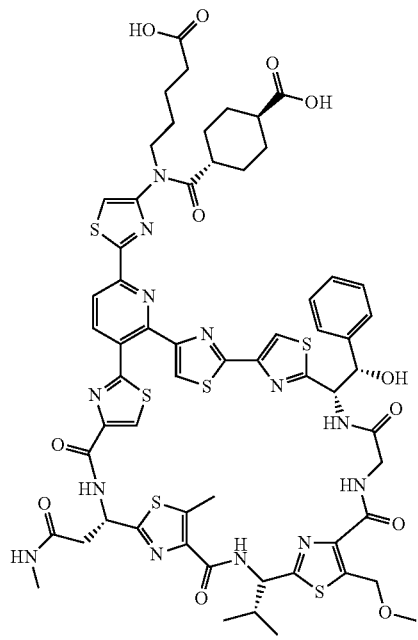
16.
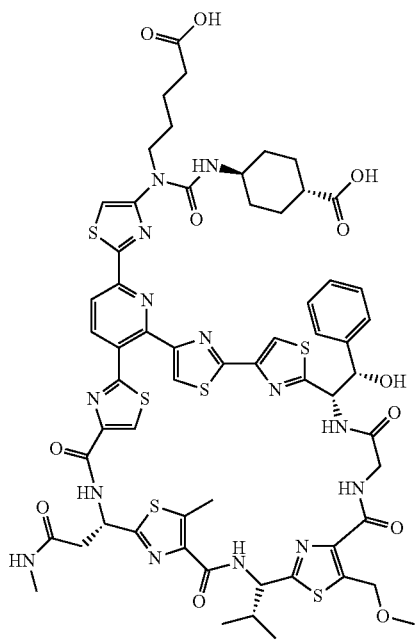
18.
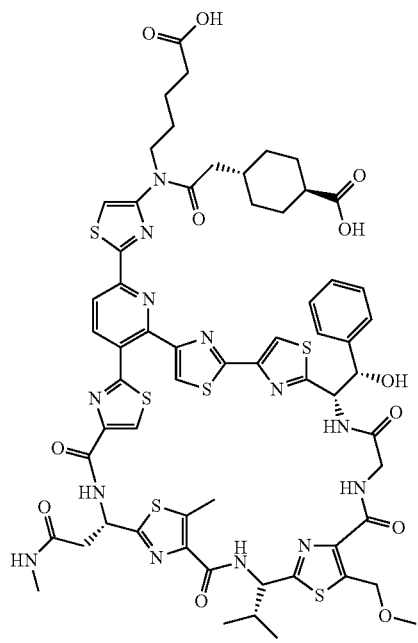
17.
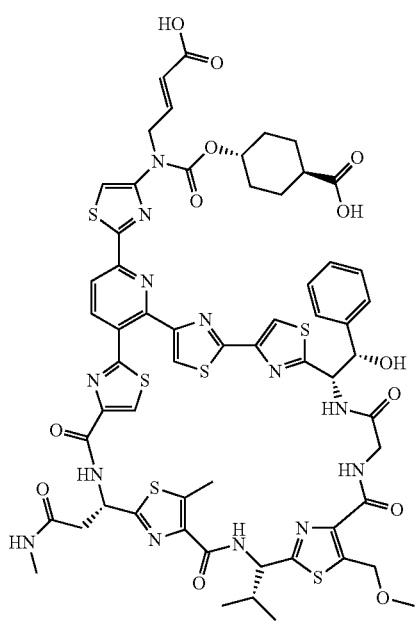
19.

TABLE A-continued
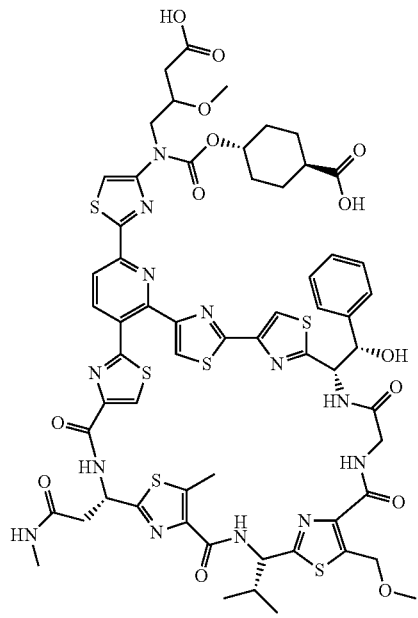
20.
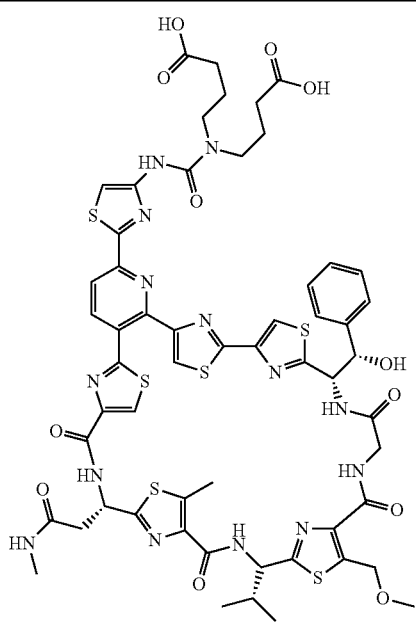
22.
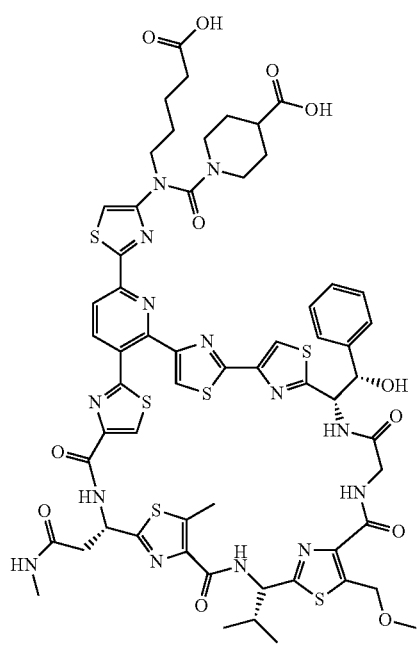
21.
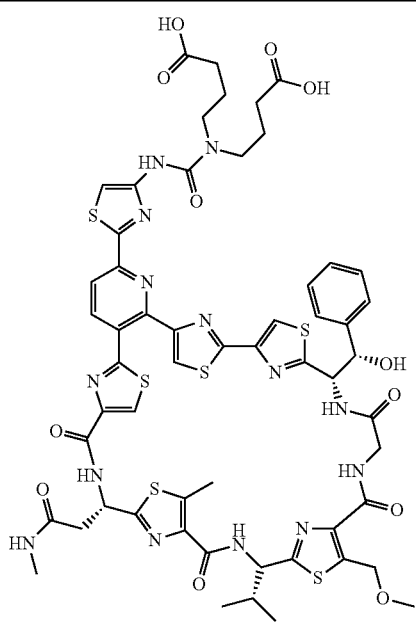
23.

TABLE A-continued
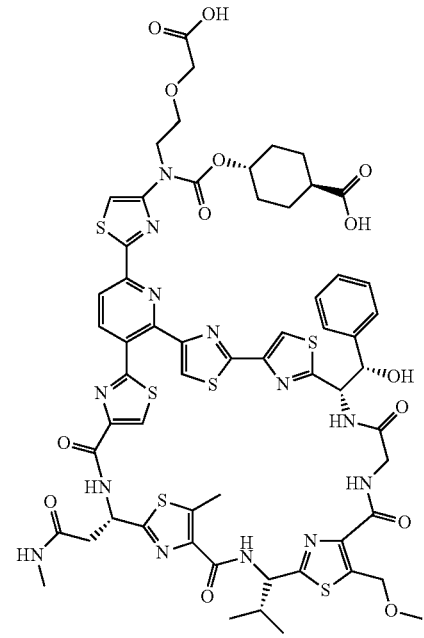
24.
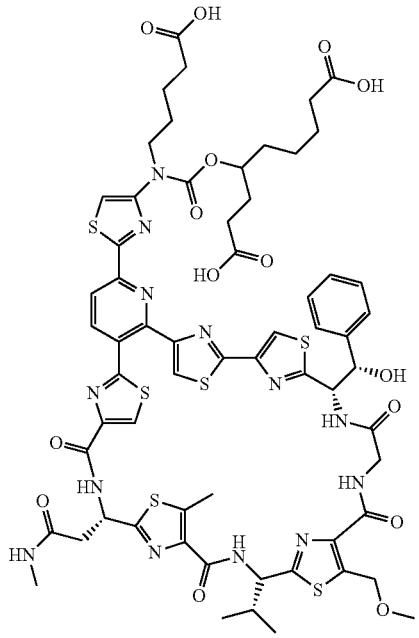
26.
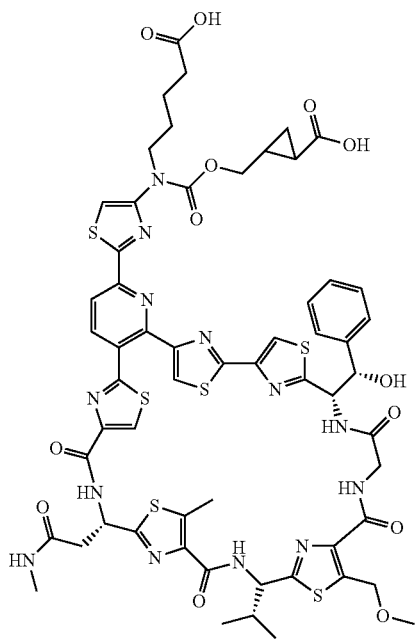
27.
25.
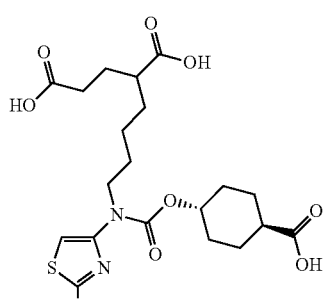
28.

TABLE A-continued
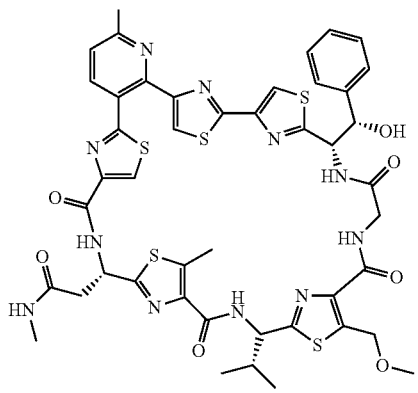
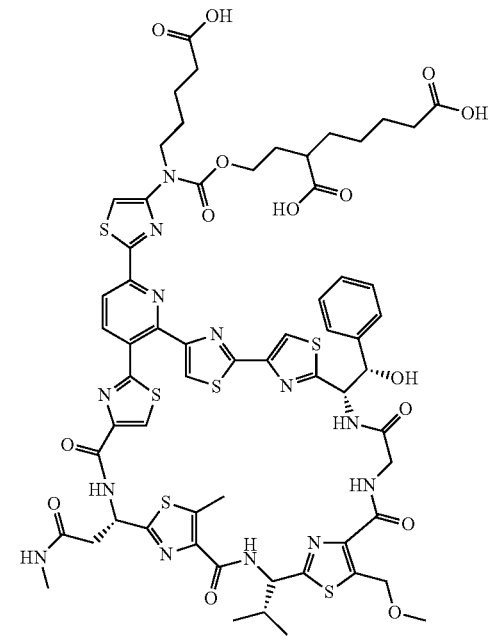
30.
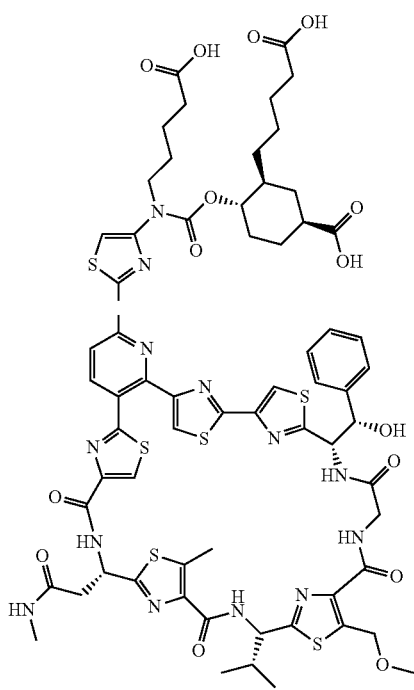
29.
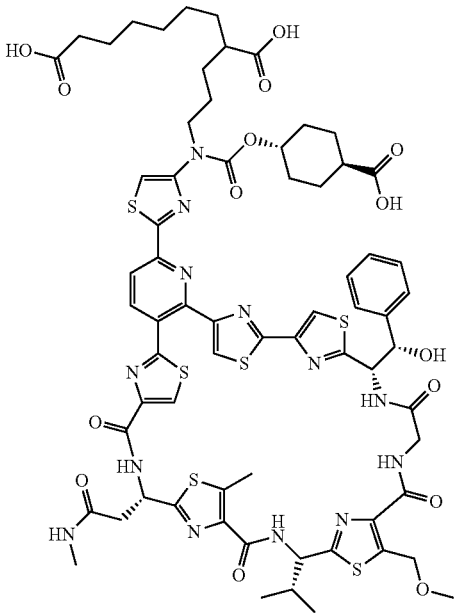
31.

TABLE A-continued
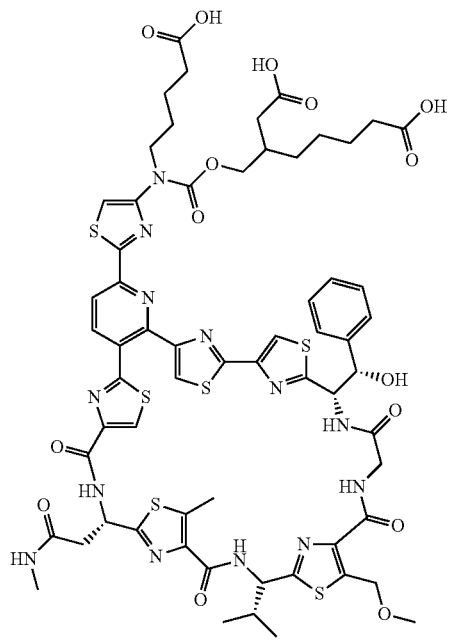
32.
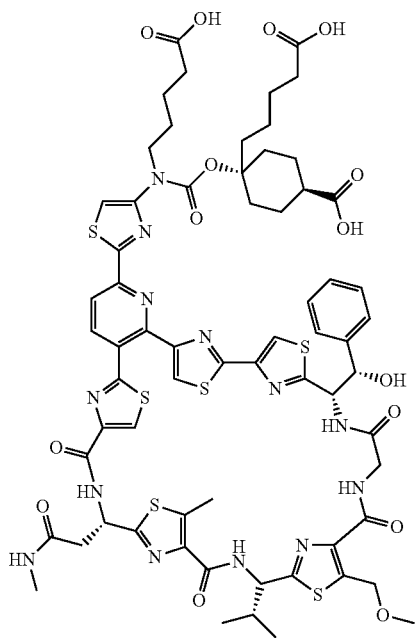
34.
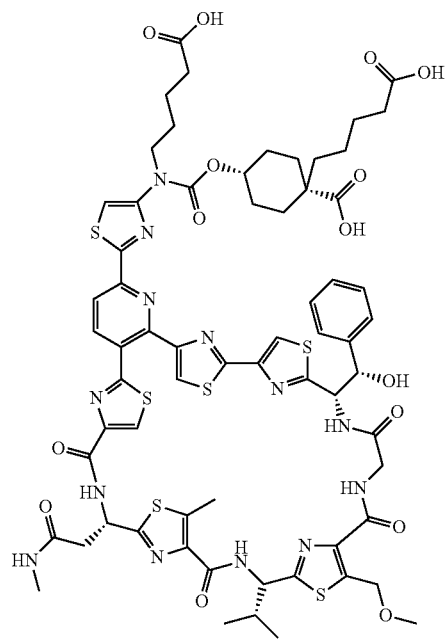
33.
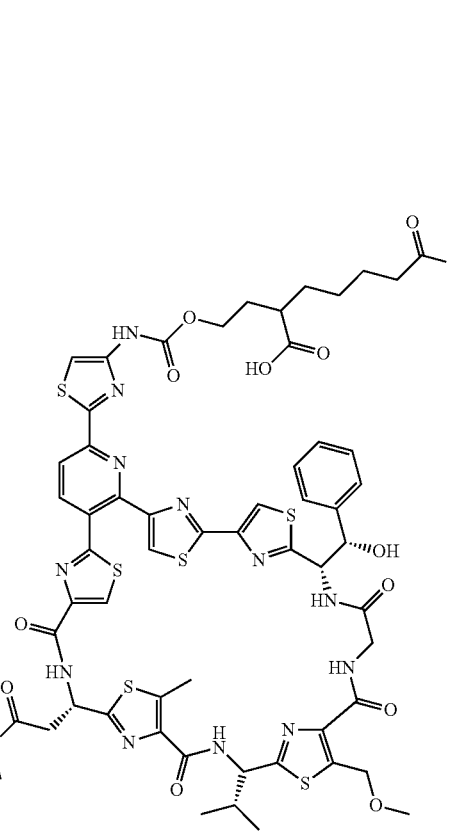
35.

TABLE B
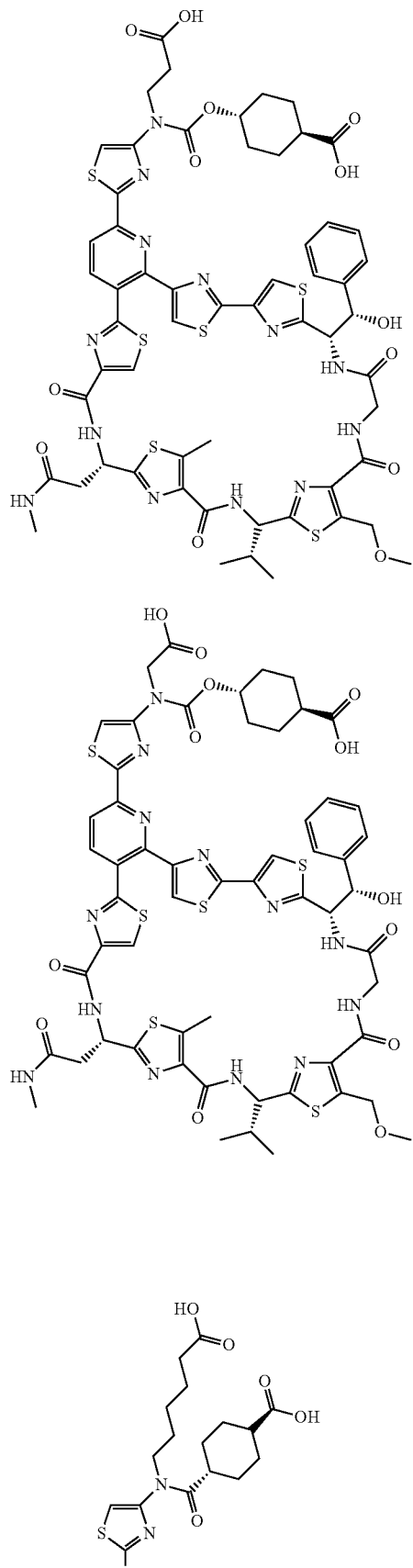
TABLE B-continued
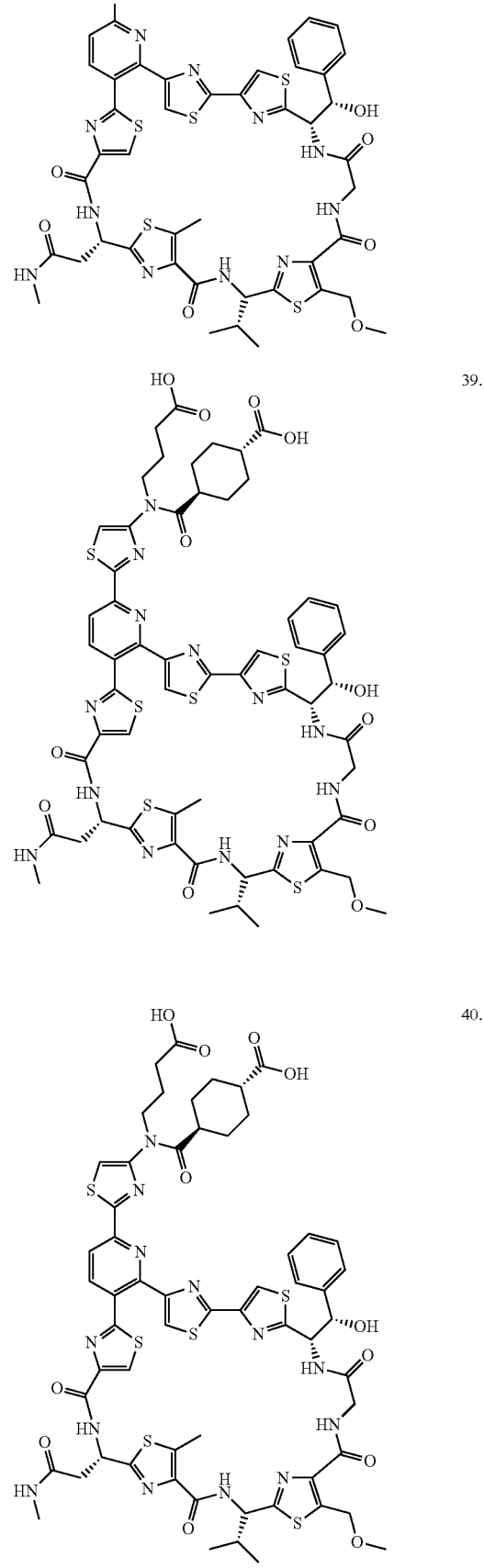

TABLE B-continued
41.
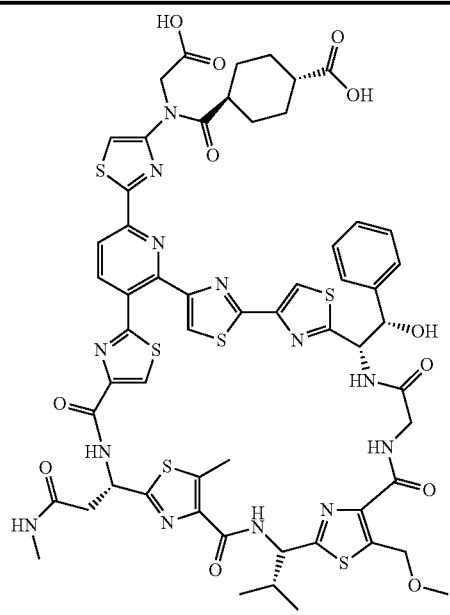
42.
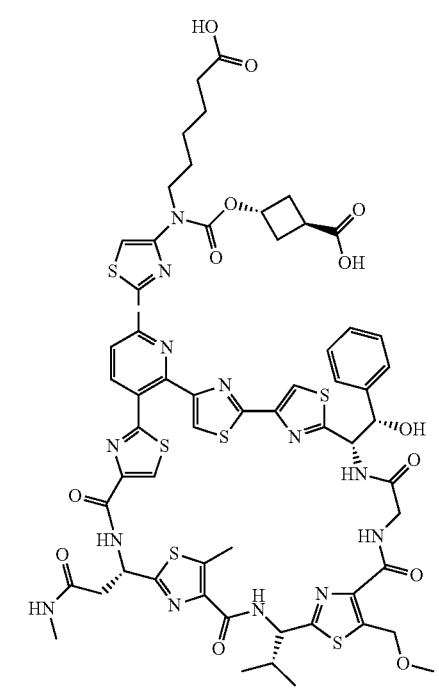
TABLE B-continued
43.
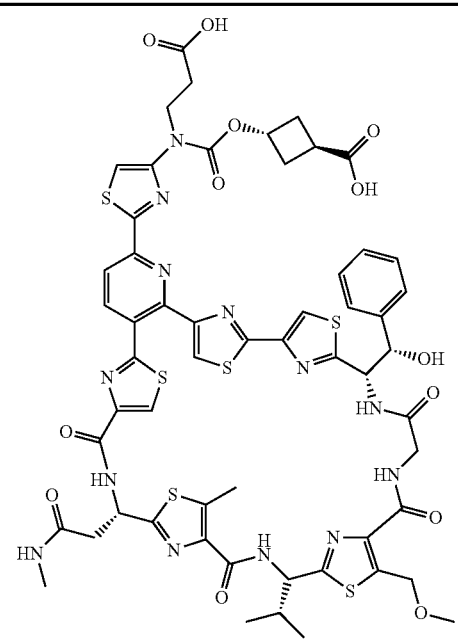
44.
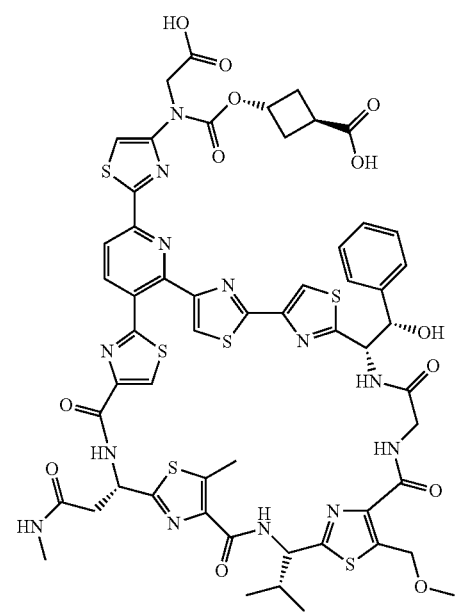
45.
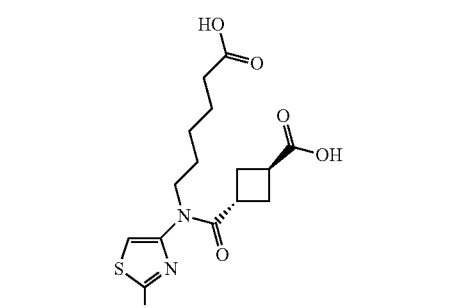

TABLE B-continued
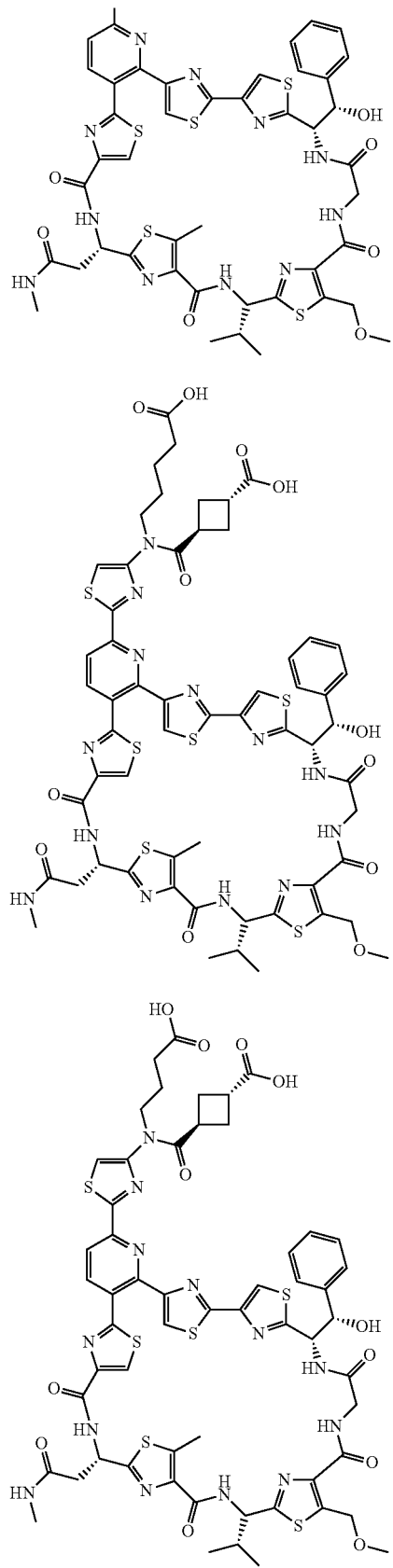
TABLE B-continued
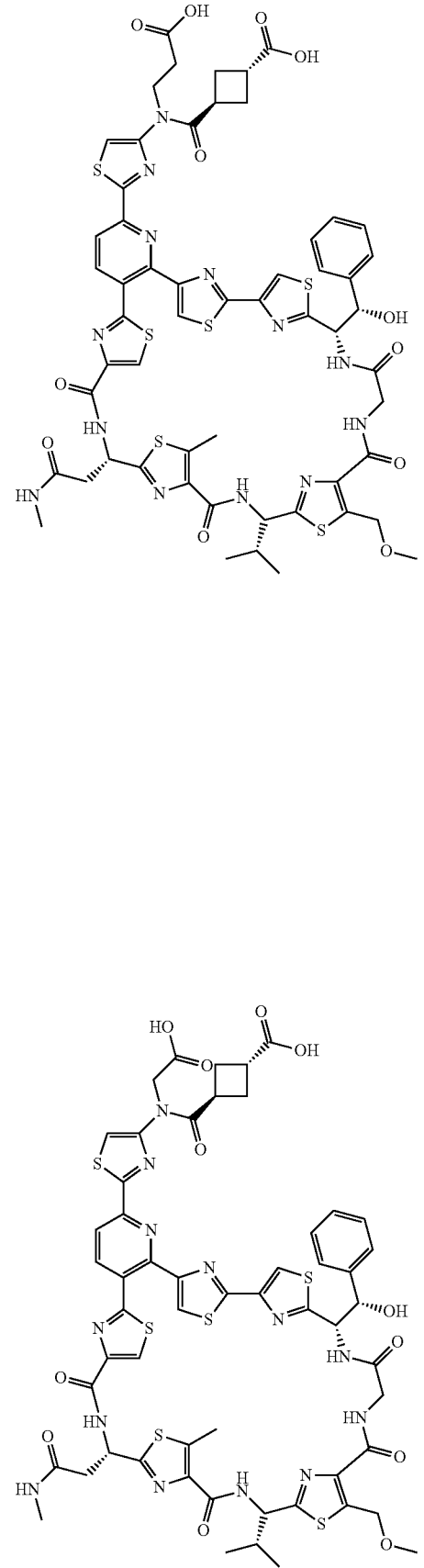

TABLE B-continued
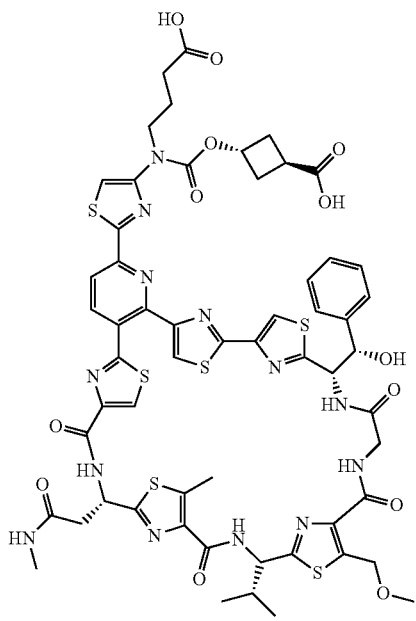
50.
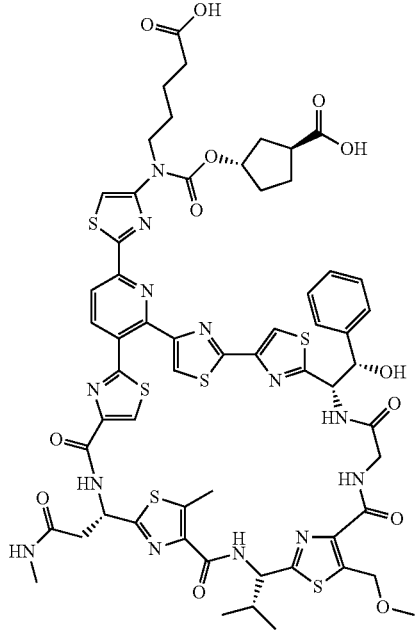
52.
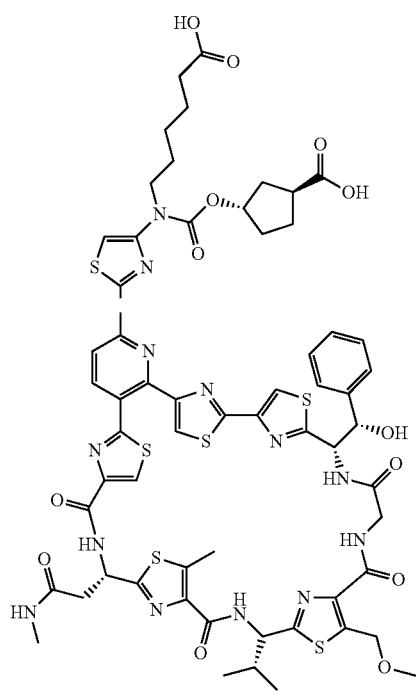
51.
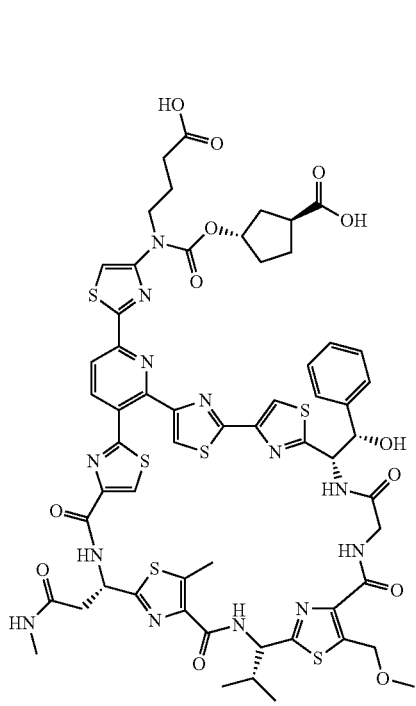
53.

TABLE B-continued
54.
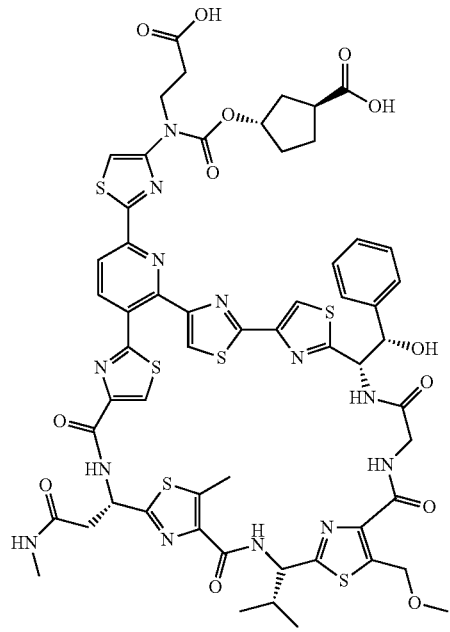
55.
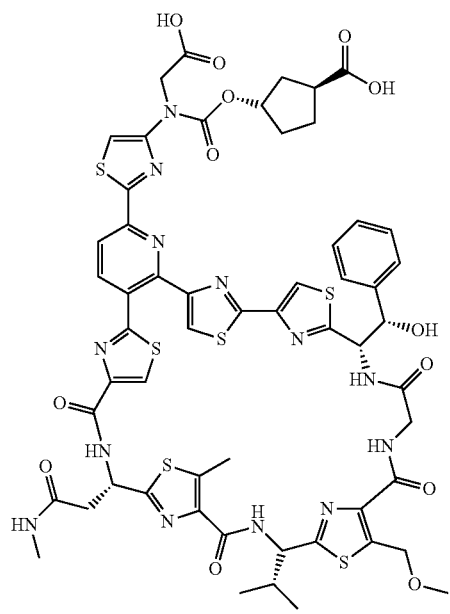
56.
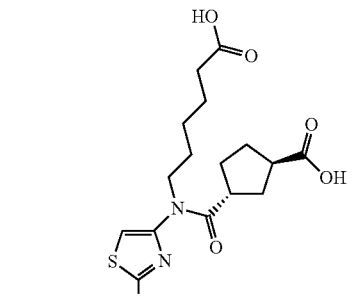
TABLE B-continued
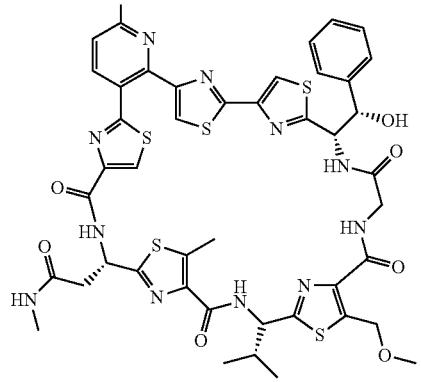
57.
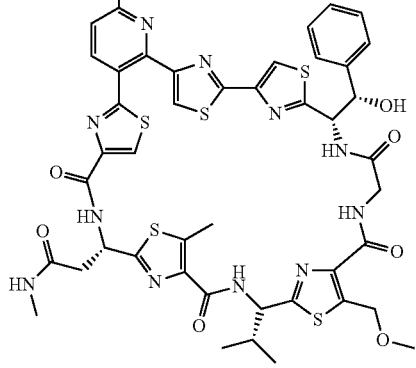
58.
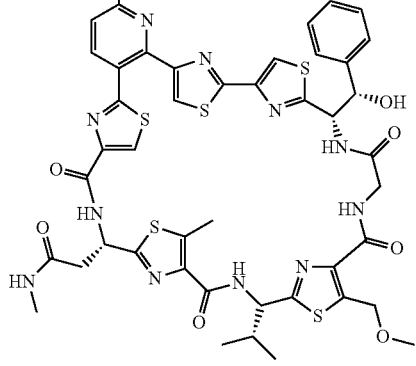

TABLE B-continued
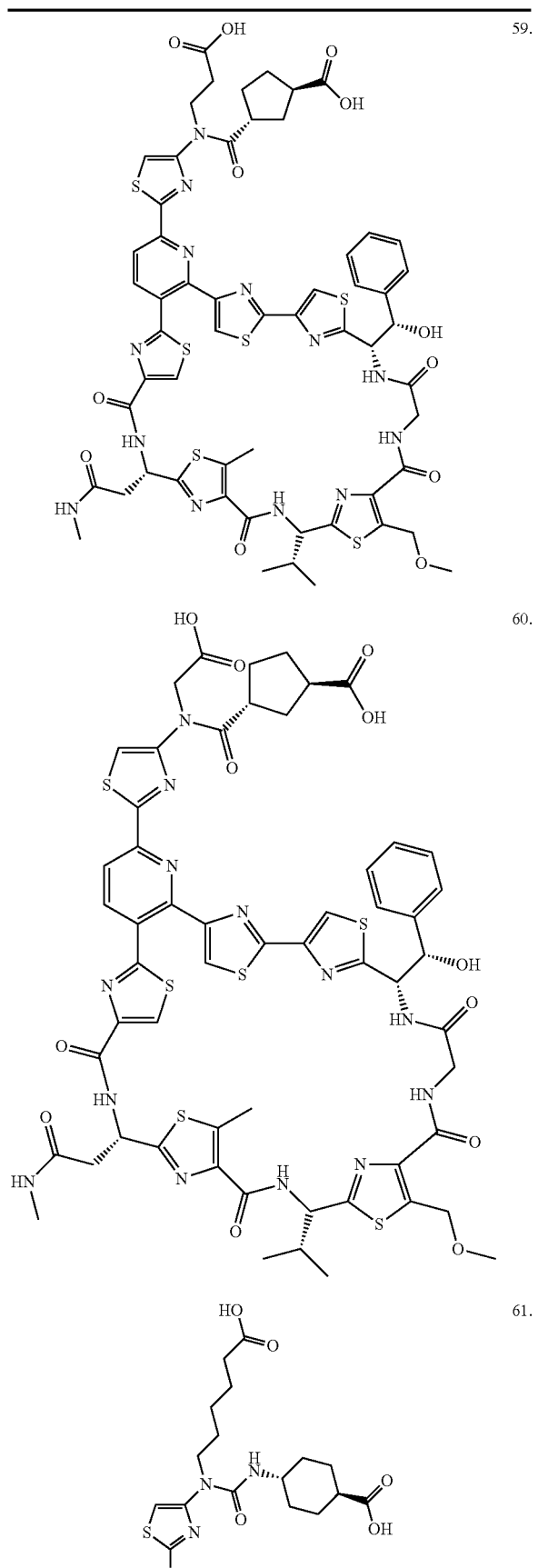
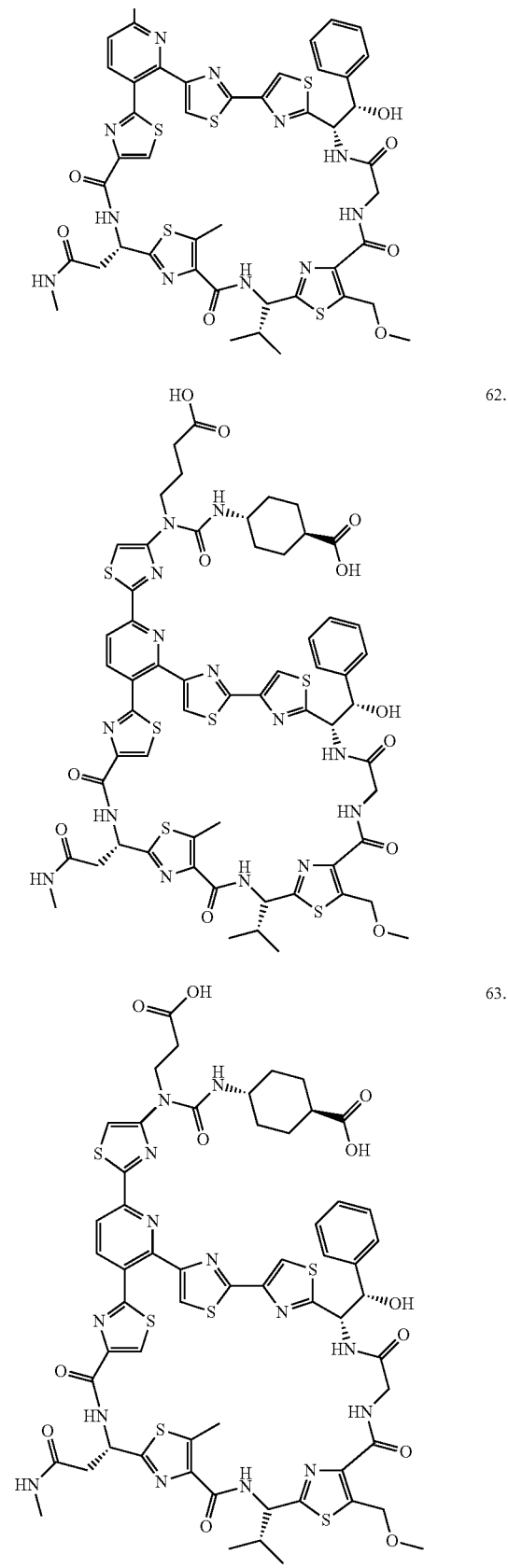

TABLE B-continued
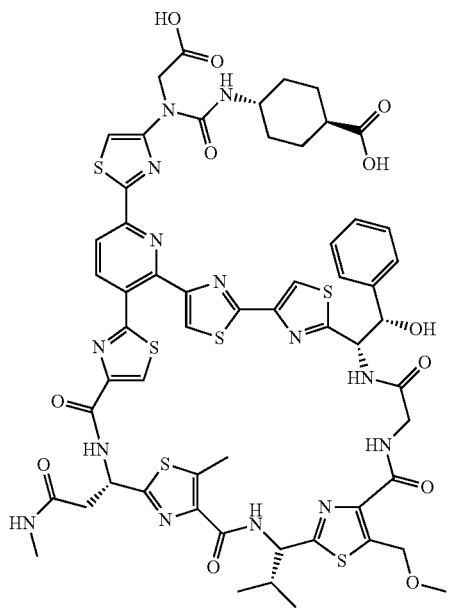
64.
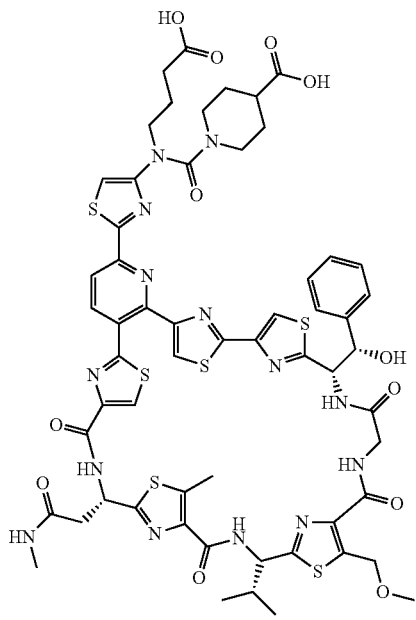
66.
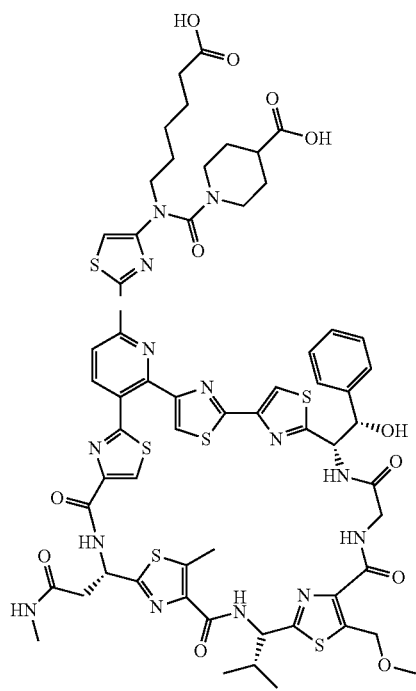
65.
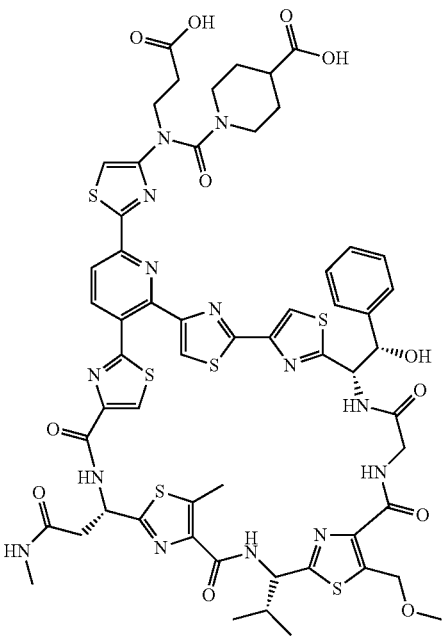
67.

TABLE B-continued
68.
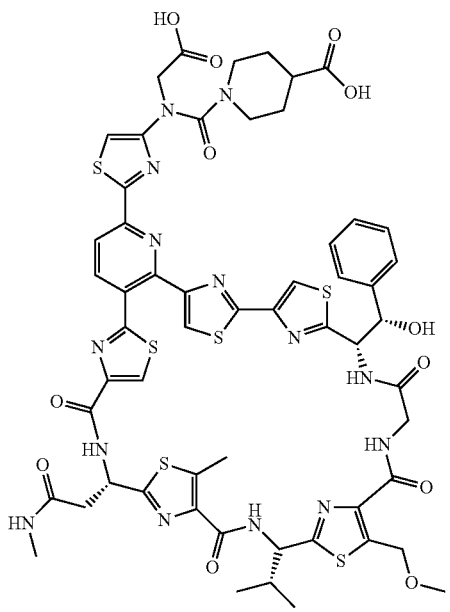
70.
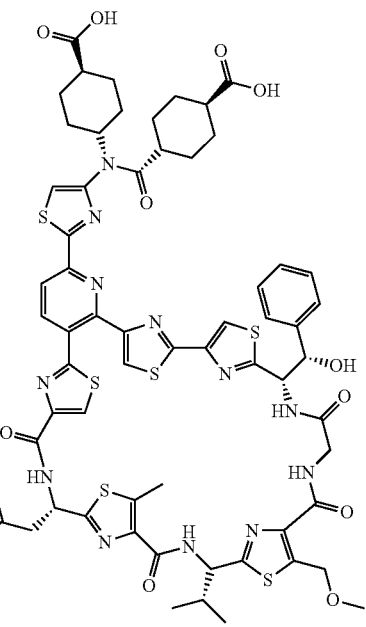
69.
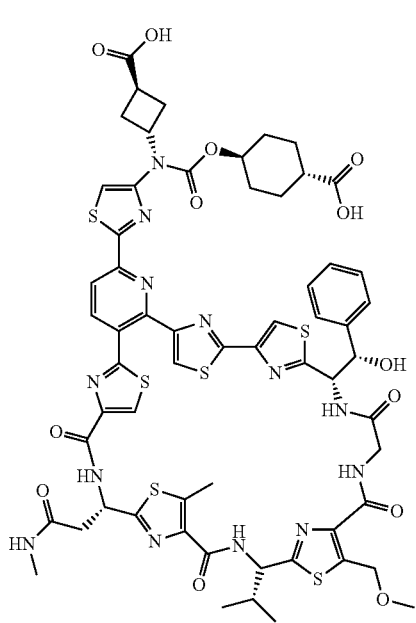
71.

TABLE B-continued
72. 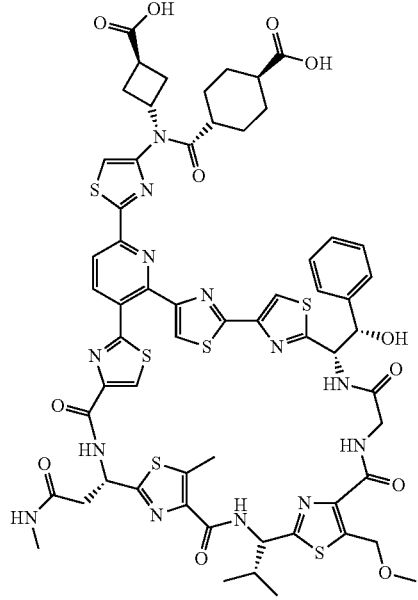
73. 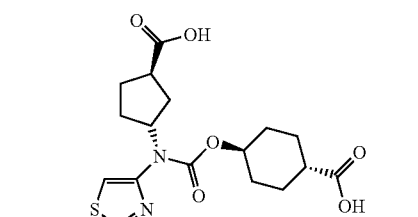
74. 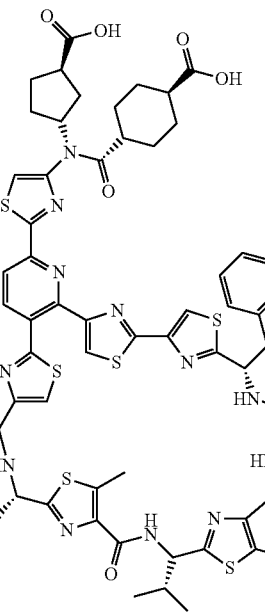
75. 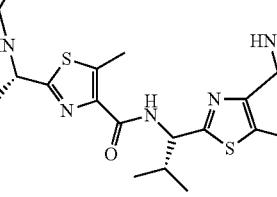

TABLE B-continued
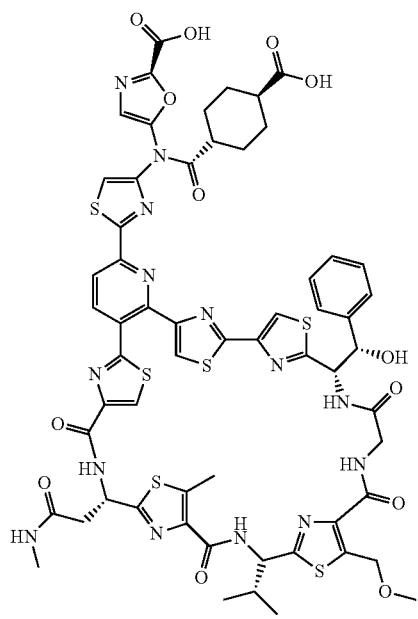
76.
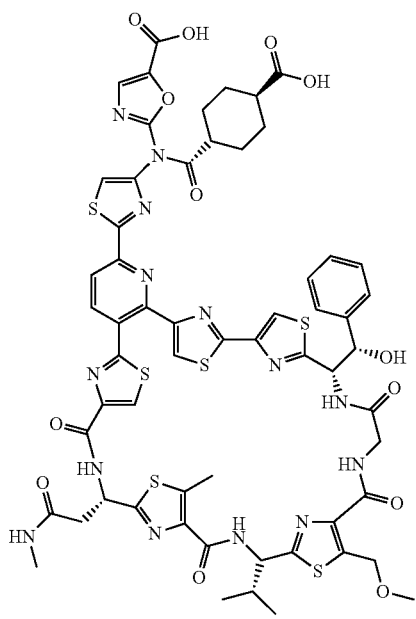
78.
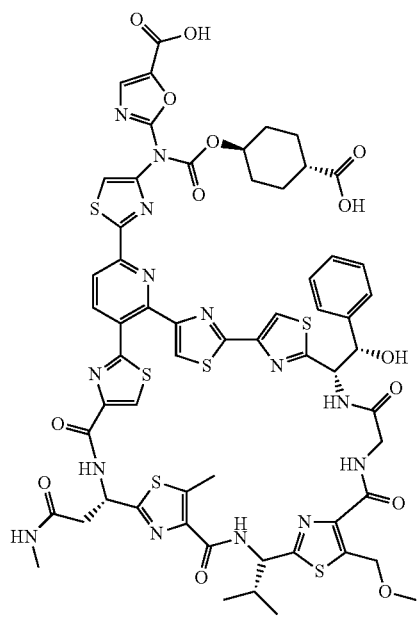
77.

TABLE B-continued
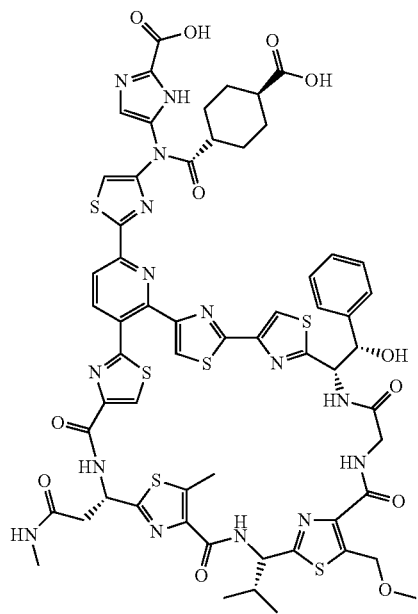
80.
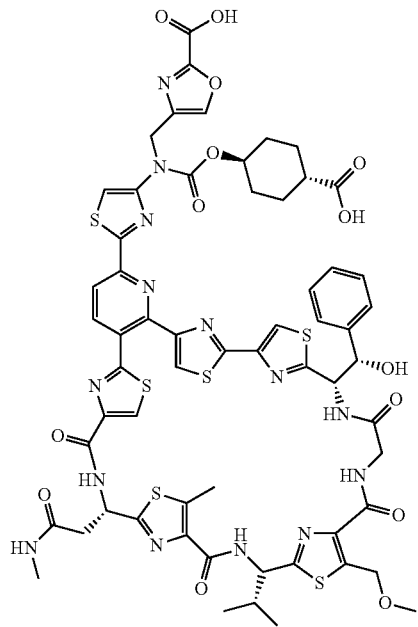
81.
TABLE B-continued
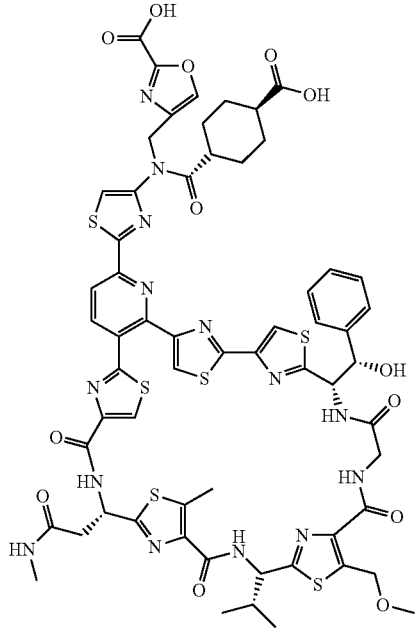
82.
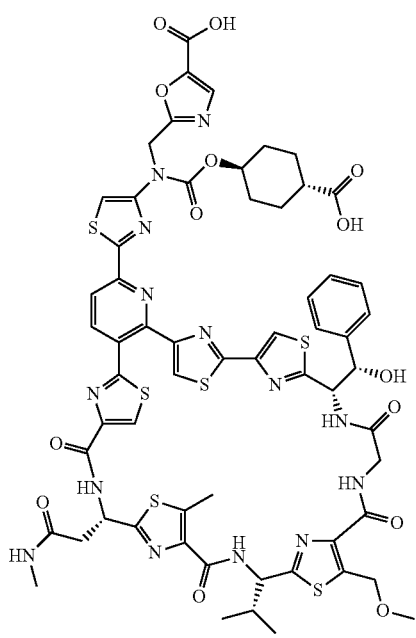
83.

TABLE B-continued
84.
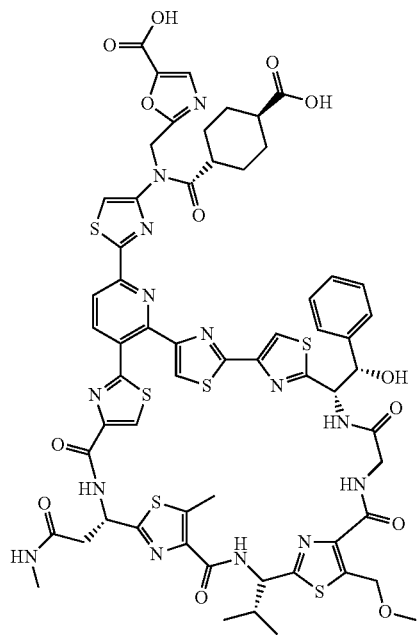
86.
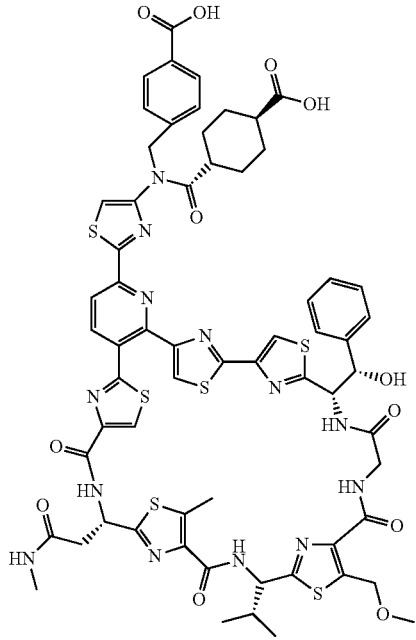
85.
87.

TABLE B-continued
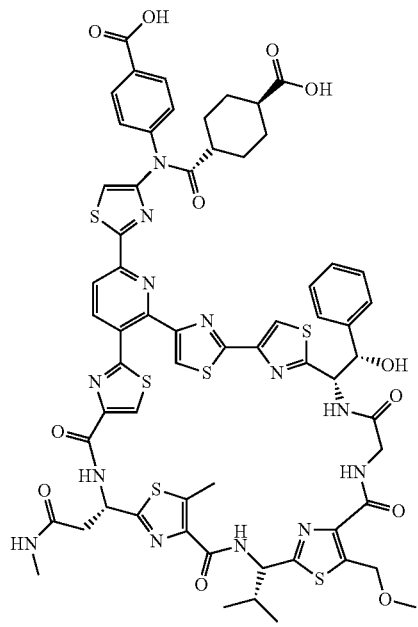
88.
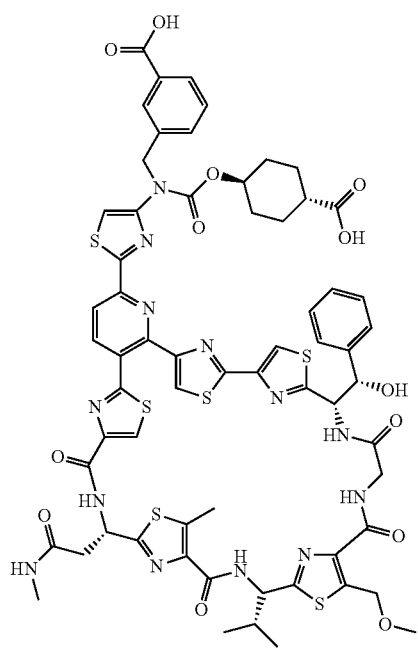
89.
TABLE B-continued
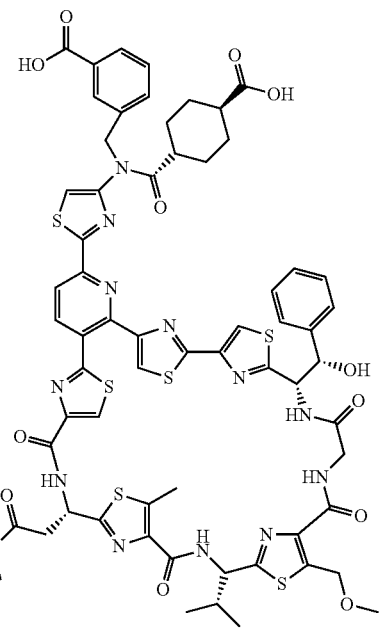
90.
91.

TABLE B-continued
92.
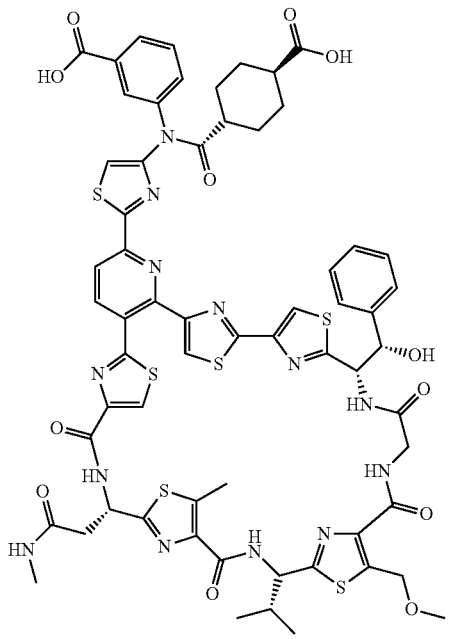
94.
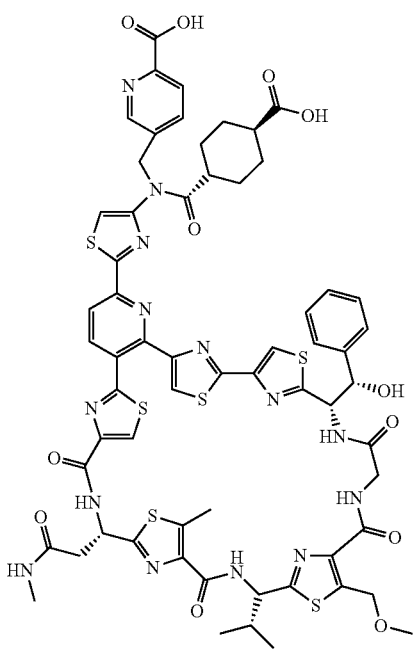
93.
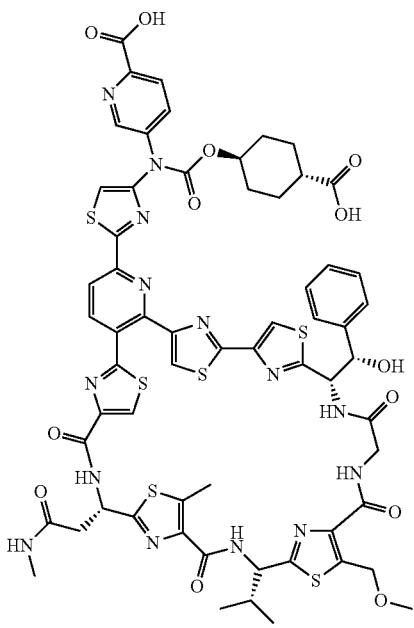
95.

TABLE B-continued
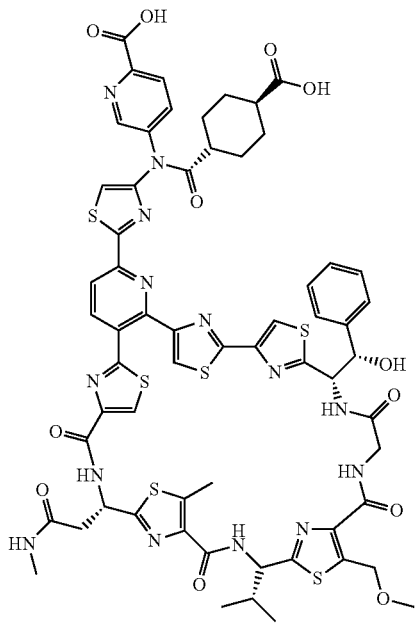
96.
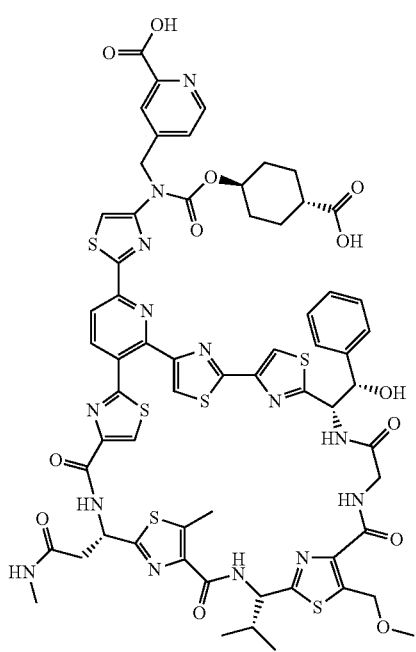
97.
TABLE B-continued
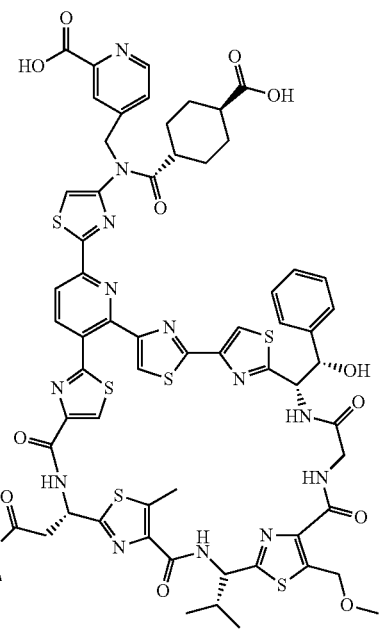
98.
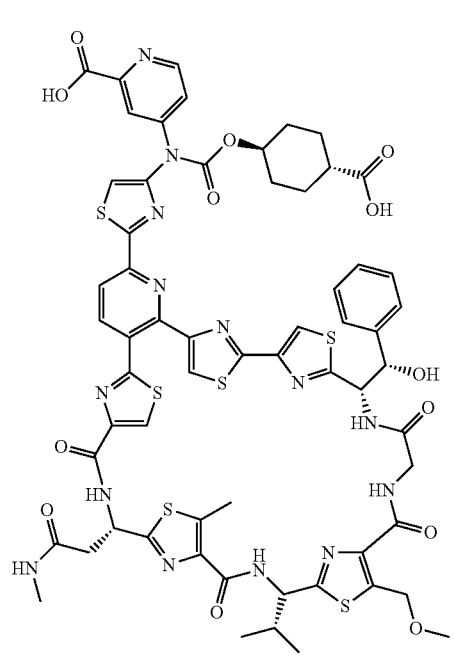
99.

TABLE B-continued
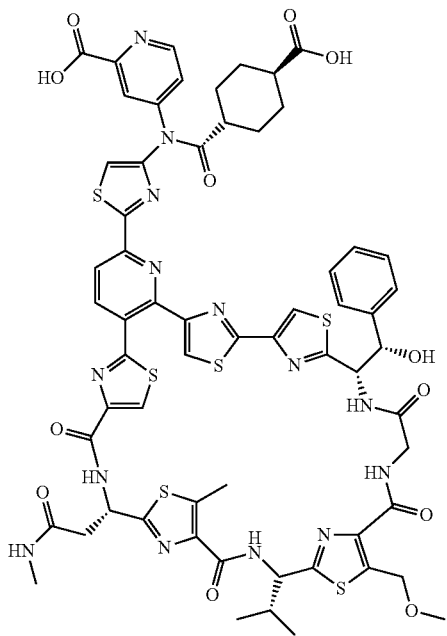
100.
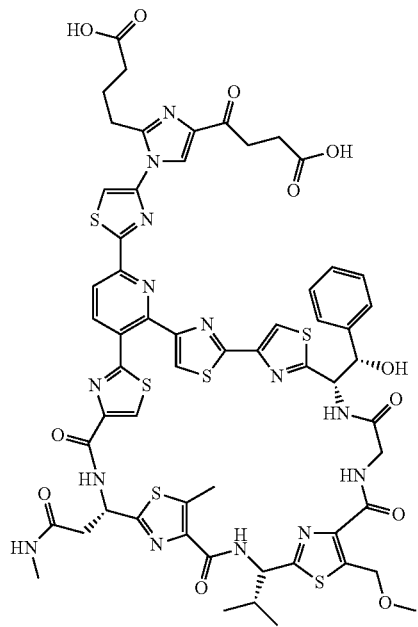
101.
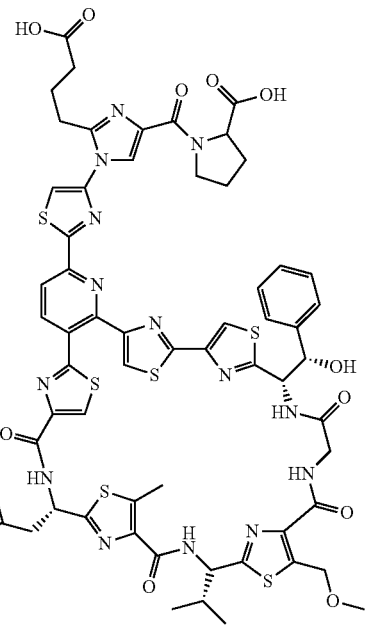
102.
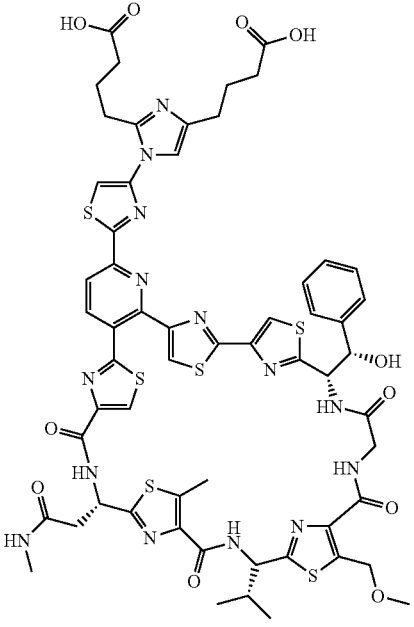
103.

TABLE B-continued

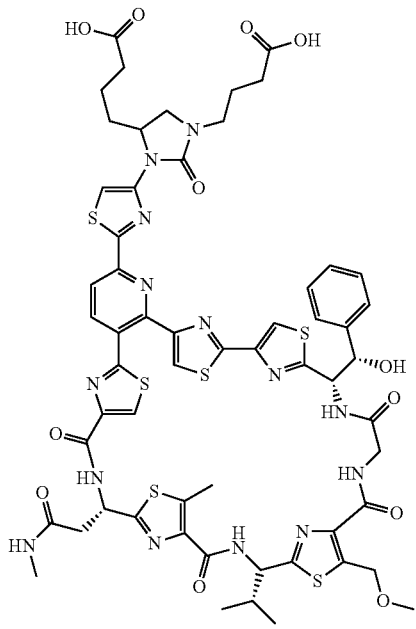

104.

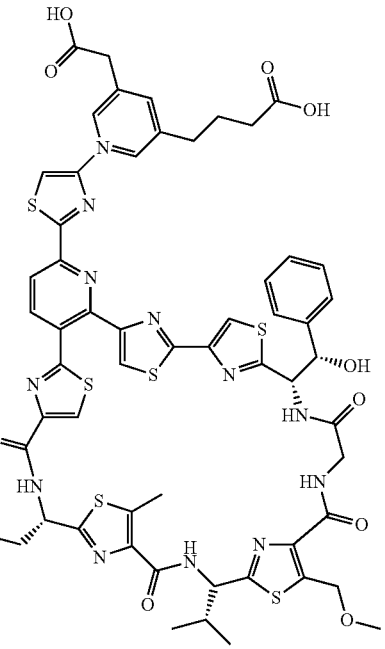

106.

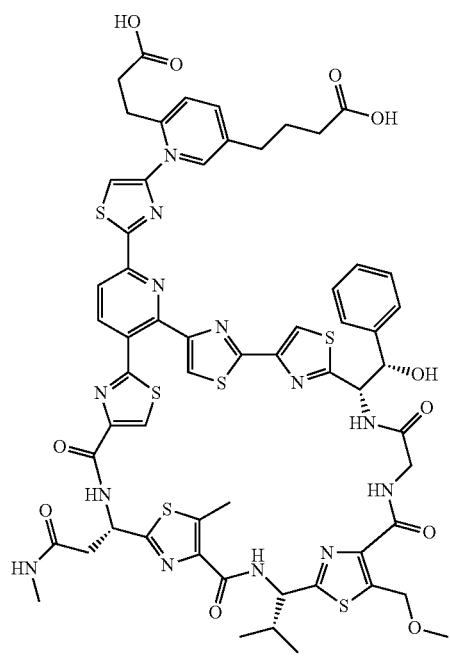

105.

In certain embodiments, the compound of the present invention is further characterized as a modulator of EF-Tu, including a prokaryotic EF-Tu, and especially including a bacterial EF-Tu. In a preferred embodiment, the compound of the invention is an EF-Tu inhibitor.

As used herein, the term "bacterial infection(s)" includes, but is not limited to, bacterial infections that occur in mammals, fish and birds as well as disorders related to bacterial infections that may be treated or prevented by administering antibiotics such as the compounds of the present invention. In addition to treating infections caused by multi-drug resistant strains of *Staphyloccocus aureus, Streptococcus pneumoniae, Mycobacterium tuberculosis* and Enterococci, the compounds of the present invention are useful in treating infections caused by other bacteria including, but not limited to, *Clostridium difficile, Propionibacterium acnes, Bacteroides fagiles, Neisseria gonorrhoeae, Branhamella catarrhalis, Haemophilus influenzae, E. coli, Pseudomonas aeruginosa, Proteus vulgaris, Klebsiella pneumonia,* and *Chlamydia trachomatis*.

Such bacterial infections and disorders related to such infections include, but are not limited to, the following: acne, rosacea, skin infection, pneumonia, otitis media, sinusitus, bronchitis, tonsillitis, and mastoiditis related to infection by *Streptococcus pneumoniae, Haemophilus influenzae, Moraxella catarrhalis, Staphylococcus aureus, Peptostreptococcus* spp. or *Pseudomonas* spp.; pharynigitis, rheumatic fever, and glomerulonephritis related to infection by *Streptococcus pyogenes,* Groups C and G streptococci, *Clostridium diptheriae,* or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; uncomplicated skin and soft tissue infections, abscesses and osteomyelitis, and puerperal fever related to infection by *Staphylococcus aureus,* coagulase-positive staphylococci (i.e., *S. epidermidis, S. hemolyticus,* etc.), *S. pyogenes, S. agalactiae,* Streptococcal groups C—F (minute-colony streptococci), viridans streptococci, *Corynebac-*

*terium* spp., *Clostridium* spp., or *Bartonella henselae*; uncomplicated acute urinary tract infections related to infection by *S. saprophyticus* or *Enterococcus* spp.; urethritis and cervicitis; sexually transmitted diseases related to infection by *Chlamydia trachomatis, Haemophilus ducreyi, Treponema pallidum, Ureaplasma urealyticum,* or *Nesseria gonorrheae*; toxin diseases related to infection by *S. aureus* (food poisoning and Toxic shock syndrome), or Groups A, S, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *C. trachomatis, N. gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium,* or *Mycobacterium intracellulare*; gastroenteritis related to infection by *Campylobacter jejuni*; intestinal protozoa related to infection by *Cryptosporidium* spp., odontogenic infection related to infection by viridans streptococci; persistent cough related to infection by *Bordetella pertussis*; gas gangrene related to infection by *Clostridium perfringens* or *Bacteroides* spp.; Skin infection by *S. aureus, Propionibacterium* acne; atherosclerosis related to infection by *Helicobacter pylori* or *Chlamydia pneumoniae*; or the like.

Further bacterial infections and disorders related to such infections that may be treated or prevented in animals include, but are not limited to, the following: bovine respiratory disease related to infection by *P. haemolytica., P. multocida, Mycoplasma bovis,* or *Bordetella* spp.; cow enteric disease related to infection by *E. coli* or protozoa (i.e., coccidia, cryptosporidia, etc.), dairy cow mastitis related to infection by *S. aureus, S. uberis, S. agalactiae, S. dysgalactiae, Klebsiella* spp., *Corynebacterium,* or *Enterococcus* spp.; swine respiratory disease related to infection by *A. pleuropneumoniae., P. multocida,* or *Mycoplasma* spp.; swine enteric disease related to infection by *E. coli, Lawsonia intracellularis, Salmonella* spp., or *Serpulina hyodyisinteriae*; cow footrot related to infection by *Fusobacterium* spp.; cow metritis related to infection by *E. coli*; cow hairy warts related to infection by *Fusobacterium necrophorum* or *Bacteroides nodosus*; cow pink-eye related to infection by *Moraxella bovis,* cow premature abortion related to infection by protozoa (i.e., neosporium); urinary tract infection in dogs and cats related to infection by *E. coli*; skin and soft tissue infections in dogs and cats related to infection by *S. epidermidis, S. intermedius,* coagulase neg. *Staphylococcus* or *P. multocida*; dental or mouth infections in dogs and goats related to infection by *Alcaligenes* spp., *Bacteroides* spp., *Clostridium* spp., *Enterobacter* spp., *Eubacterium* spp., *Peptostreptococcus* spp., *Porphfyromonas* spp., *Campylobacter* spp., *Actinomyces* spp., *Erysipelothrix* spp., *Rhodococcus* spp., *Trypanosoma* spp., *Plasmodium* spp., *Babesia* spp., *Toxoplasma* spp., *Pneumocystis* spp., *Leishmania* spp., *Trichomonas* spp. or *Prevotella* spp. Other bacterial infections and disorders related to such infections that may be treated or prevented in accord with the method of the present invention are referred to in J. P. Sanford at al., "The Sanford Guide To Antimicrobial Therapy," 26th Edition, (Antimicrobial Therapy, Inc., 1996).

Further bacterial infections and disorders related to such infections that may be treated or prevented in animals include, but are not limited to, central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, antibacterial prophylaxis in immunosuppressed patients, such as patients receiving cancer chemotherapy, or organ transplant patients and chronic diseases caused by infectious organisms, e.g., arteriosclerosis.

Bacterial protein synthesis requires EF-Tu chaperone proteins. EF-Tu is one of the most abundant proteins in bacteria, as well as one of the most highly conserved, and in a number of species the gene is duplicated with identical function. When bound to GTP, EF-Tu can form a complex with most aminoacylated tRNAs, loading the tRNA onto the ribosome. In one embodiment, the bacterial infection is associated with the activity of EF-Tu. Without being bound by theory, it is believed that the disruption of EF-Tu protein activity by the compounds of the invention will interfere with protein synthesis and thus bacterial function and/or proliferation. Because EF-Tu is highly conserved across Gram-positive and Gram-negative bacteria, the compounds of the present invention are useful for treating infections of both classes of bacteria.

As used herein, the term "EF-Tu-associated state" or "EF-Tu-associated disorder" include disorders and states (e.g., a disease state) that are associated with the activity of EF-Tu. A non-limiting example of an EF-Tu associated disorder is a bacterial infection in a subject.

The present invention includes treatment of bacterial infections, as well as EF-Tu-associated disorders, as described above, but the invention is not intended to be limited to the manner by which the compound performs its intended function of treatment of a disease. The present invention includes treatment of diseases described herein in any manner that allows treatment to occur, e.g., bacterial infection.

In certain embodiments, the invention provides a pharmaceutical composition of any of the compounds of the present invention. In a related embodiment, the invention provides a pharmaceutical composition of any of the compounds of the present invention and a pharmaceutically acceptable carrier or excipient of any of these compounds. In certain embodiments, the invention includes the compounds as novel chemical entities.

In one embodiment, the invention includes a packaged bacterial infection treatment. The packaged treatment includes a compound of the invention packaged with instructions for using an effective amount of the compound of the invention for an intended use.

The compounds of the present invention are suitable as active agents in pharmaceutical compositions that are efficacious particularly for treating bacterial infections. The pharmaceutical composition in various embodiments has a pharmaceutically effective amount of the present active agent along with other pharmaceutically acceptable excipients, carriers, fillers, diluents and the like. The phrase, "pharmaceutically effective amount" as used herein indicates an amount necessary to administer to a host, or to a cell, issue, or organ of a host, to achieve a therapeutic result, especially an anti-bacterial infection effect, e.g., inhibition of proliferation of a bacterium, or of any other bacterial infection.

In other embodiments, the present invention provides a method for inhibiting the activity of an EF-Tu protein. The method includes contacting a cell with any of the compounds of the present invention. In a related embodiment, the method further provides that the compound is present in an amount effective to selectively inhibit the activity of an EF-Tu protein.

In other embodiments, the present invention provides a use of any of the compounds of the invention for manufacture of a medicament to treat a bacterial infection in a subject.

In other embodiments, the invention provides a method of manufacture of a medicament, including formulating any of the compounds of the present invention for treatment of a subject.

DEFINITIONS

The term "treat," "treated," "treating" or "treatment" includes the diminishment or alleviation of at least one symptom associated or caused by the state, disorder or disease being treated. In certain embodiments, the treatment comprises the induction of a bacterial infection, followed by the activation of the compound of the invention, which would in turn diminish or alleviate at least one symptom associated or caused by the bacterial infection being treated. For example, treatment can be diminishment of one or several symptoms of a disorder or complete eradication of a disorder.

The term "subject" is intended to include organisms, e.g., prokaryotes and eukaryotes, which are capable of suffering from or afflicted with a bacterial infection. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from a bacterial infection, and for diseases or conditions described herein. In another embodiment, the subject is a cell.

The language "EF-Tu-modulating compound," "modulator of EF-Tu" or "EF-Tu inhibitor" refers to compounds that modulate, e.g., inhibit, or otherwise alter, the activity of EF-Tu. Examples of EF-Tu-modulating compounds include compounds of formula I, II, III, IV and V, as well as Table A and Table B (including pharmaceutically acceptable salts thereof, as well as enantiomers, stereoisomers, rotamers, tautomers, diastereomers, atropisomers or racemates thereof).

Additionally, a method of the invention includes administering to a subject an effective amount of an EF-Tu-modulating compound of the invention, e.g., EF-Tu-modulating compounds of Formula I, II, III, IV and V, as well as Table A and Table B (including pharmaceutically acceptable salts thereof, as well as enantiomers, stereoisomers, rotamers, tautomers, diastereomers, atropisomers or racemates thereof).

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term "alkyl" also includes alkenyl groups and alkynyl groups. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl, isobutyl and sec-butyl. Moreover, the term $C_{3-6}$-cycloalkyl includes, but is not limited to, cyclopropyl, cyclopentyl, and cyclohexyl. As discussed below, these alkyl groups, as well as cycloalkyl groups, may be further substituted. "$C_0$-$C_n$alkyl" refers to a single covalent bond ($C_0$) or an alkyl group having from 1 to n carbon atoms; for example "$C_0$-$C_4$alkyl" refers to a single covalent bond or a $C_1$-$C_4$alkyl group; "$C_0$-$C_8$alkyl" refers to a single covalent bond or a $C_1$-$C_8$alkyl group. In some instances, a substituent of an alkyl group is specifically indicated. For example, "$C_1$-$C_4$hydroxyalkyl" refers to a $C_1$-$C_4$alkyl group that has at least one hydroxy substituent.

"Alkylene" refers to a divalent alkyl group, as defined above. $C_0$-$C_4$alkylene is a single covalent bond or an alkylene group having from 1 to 4 carbon atoms; and $C_0$-$C_6$alkylene is a single covalent bond or an alkylene group having from 1 to 6 carbon atoms. "Alkenylene" and "Alkynylene" refer to divalent alkenyl and alkynyl groups respectively, as defined above.

A "cycloalkyl" is a group that comprises one or more saturated and/or partially saturated rings in which all ring members are carbon, such as cyclopropyl, cyclobutyl, cyclopentyl, cyclohexyl, cycloheptyl, cyclooctyl, adamantyl, decahydro-naphthalenyl, octahydro-indenyl, and partially saturated variants of the foregoing, such as cyclohexenyl. Cycloalkyl groups do not comprise an aromatic ring or a heterocyclic ring. Certain cycloalkyl groups are $C_3$-$C_8$cycloalkyl, in which the group contains a single ring with from 3 to 8 ring members. A "($C_3$-$C_8$cycloalkyl)$C_0$-$C_4$alkyl" is a $C_3$-$C_8$cycloalkyl group linked via a single covalent bond or a $C_1$-$C_4$alkylene group. In certain aspects, $C_{3-6}$-cycloalkyl groups are substituted one or more times (or preferably between one and five times) with substitutents independently selected from a halogen atom, aryl, heteroaryl, trihalomethyl, $C_{1-4}$-alkoxy or $C_{1-4}$-alkyl.

Moreover, alkyl (e.g., methyl, ethyl, propyl, butyl, pentyl, hexyl, etc.) include both "unsubstituted alkyl" and "substituted alkyl", the latter of which refers to alkyl moieties having substituents replacing a hydrogen on one or more carbons of the hydrocarbon backbone, which allow the molecule to perform its intended function.

The term "substituted" is intended to describe moieties having substituents replacing a hydrogen on one or more atoms, e.g. C, O or N, of a molecule. Such substituents can include, for example, oxo, alkyl, alkoxy, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, morpholino, phenol, benzyl, phenyl, piperizine, cyclopentane, cyclohexane, pyridine, 5H-tetrazole, triazole, piperidine, or an aromatic or heteroaromatic moiety, and any combination thereof.

Further examples of substituents of the invention, which are not intended to be limiting, include moieties selected from straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}NR'R''$ (e.g., $-NH_2$), $(CR'R'')_{0-3}CN$ (e.g., —CN), —NO$_2$, halogen (e.g., —F, —Cl, —Br, or —I), $(CR'R'')_{0-3}C(halogen)_3$ (e.g., —CF$_3$), $(CR'R'')_{0-3}CH(halogen)_2$, $(CR'R'')_{0-3}CH_2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., –SO$_3$H, —OSO$_3$H), $(CR'R'')_{0-3}O(CR'R'')_{0-3}H$ (e.g., —CH$_2$OCH$_3$ and —OCH$_3$), $(CR'R'')_{0-3}S(CR'R'')_{0-3}H$ (e.g., —SH and —SCH$_3$), $(CR'R'')_{0-3}OH$ (e.g., —OH), $(CR'R'')_{0-3}COR'$, $(CR'R'')_{0-3}$ (substituted or unsubstituted phenyl), $(CR'R'')_{0-3}(C_3-C_8$ cycloalkyl), $(CR'R'')_{0-3}CO_2R'$ (e.g., —CO$_2$H), or $(CR'R'')_{0-3}OR'$ group, or the side chain of any naturally occurring amino acid; wherein R' and R" are each independently hydrogen, a $C_1$-$C_5$ alkyl, $C_2$-$C_5$ alkenyl, $C_2$-$C_5$ alkynyl, or aryl group. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, oxime, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety, and any combination thereof. In certain embodiments, a carbonyl moiety (C=O) may be further derivatized with an oxime moiety, e.g., an aldehyde moiety may be derivatized as its oxime (—C=N—OH) analog. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (i.e., benzyl)).

The term "alkenyl" includes unsaturated aliphatic groups analogous in length and possible substitution to the alkyls described above, but which contain at least one double bond.

For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups that include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "amine" or "amino" should be understood as being broadly applied to both a molecule, or a moiety or functional group, as generally understood in the art, and may be primary, secondary, or tertiary. The term "amine" or "amino" includes compounds where a nitrogen atom is covalently bonded to at least one carbon, hydrogen or heteroatom. The terms include, for example, but are not limited to, "alkylamino," "arylamino," "diarylamino," "alkylarylamino," "alkylaminoaryl," "arylaminoalkyl," "alkaminoalkyl," "amide," "amido," and "aminocarbonyl." The term "alkyl amino" comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino)

The term "aryl" includes groups, including 5- and 6-membered single-ring aromatic groups that may include from zero to four heteroatoms, for example, phenyl, pyrrole, furan, thiophene, thiazole, isothiaozole, imidazole, triazole, tetrazole, pyrazole, oxazole, isoxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, anthryl, phenanthryl, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics." The aromatic ring can be substituted at one or more ring positions with such substituents as described above, as for example, alkyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrathydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

The term "acyl" includes compounds and moieties which contain the acyl radical ($CH_3CO-$) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups and may include cyclic groups such as cyclopentoxy. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "carbonyl" or "carboxy" includes compounds and moieties which contain a carbon connected with a double bond to an oxygen atom, and tautomeric forms thereof. Examples of moieties that contain a carbonyl include aldehydes, ketones, carboxylic acids, amides, esters, anhydrides, etc. The term "carboxy moiety" or "carbonyl moiety" refers to groups such as "alkylcarbonyl" groups wherein an alkyl group is covalently bound to a carbonyl group, "alkenylcarbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl moiety. For example, the term includes moieties such as, for example, aminocarbonyl moieties, (wherein a nitrogen atom is bound to the carbon of the carbonyl group, e.g., an amide), aminocarbonyloxy moieties, wherein an oxygen and a nitrogen atom are both bond to the carbon of the carbonyl group (e.g., also referred to as a "carbamate"). Furthermore, aminocarbonylamino groups (e.g., ureas) are also include as well as other combinations of carbonyl groups bound to heteroatoms (e.g., nitrogen, oxygen, sulfur, etc. as well as carbon atoms). Furthermore, the heteroatom can be further substituted with one or more alkyl, alkenyl, alkynyl, aryl, aralkyl, acyl, etc. moieties.

The term "thiocarbonyl" or "thiocarboxy" includes compounds and moieties which contain a carbon connected with a double bond to a sulfur atom. The term "thiocarbonyl moiety" includes moieties that are analogous to carbonyl moieties. For example, "thiocarbonyl" moieties include aminothiocarbonyl, wherein an amino group is bound to the carbon atom of the thiocarbonyl group, furthermore other thiocarbonyl moieties include, oxythiocarbonyls (oxygen bound to the carbon atom), aminothiocarbonylamino groups, etc.

The term "ether" includes compounds or moieties that contain an oxygen bonded to two different carbon atoms or heteroatoms. For example, the term includes "alkoxyalkyl" which refers to an alkyl, alkenyl, or alkynyl group covalently bonded to an oxygen atom that is covalently bonded to another alkyl group.

The term "ester" includes compounds and moieties that contain a carbon or a heteroatom bound to an oxygen atom that is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom that is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O$^-$.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" include moieties with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

Additionally, the phrase "any combination thereof" implies that any number of the listed functional groups and molecules may be combined to create a larger molecular architecture. For example, the terms "phenyl," "carbonyl" (or "=O"), "—O—," "—OH," and $C_{1-6}$ (i.e., —CH$_3$ and —CH$_2$CH$_2$CH$_2$—) can be combined to form a 3-methoxy-4-propoxybenzoic acid substituent. It is to be understood that when combining functional groups and molecules to create a larger molecular architecture, hydrogens can be removed or added, as required to satisfy the valence of each atom.

It is to be understood that all of the compounds of the invention described above will further include bonds between adjacent atoms and/or hydrogens as required to satisfy the valence of each atom. That is, bonds and/or hydrogen atoms are added to provide the following number of total bonds to each of the following types of atoms: carbon: four bonds; nitrogen: three bonds; oxygen: two bonds; and sulfur: two-six bonds.

It will be noted that the structures of some of the compounds of this invention include asymmetric carbon atoms. It is to be understood accordingly that the isomers arising from such asymmetry (e.g., all enantiomers, stereoisomers, rotamers, tautomers, diastereomers, or racemates) are included within the scope of this invention. Such isomers can be obtained in substantially pure form by classical separation techniques and by stereochemically controlled synthesis. Furthermore, the structures and other compounds and moieties discussed in this application also include all tautomers thereof. Compounds described herein may be obtained through art recognized synthesis strategies.

It will also be noted that the substituents of some of the compounds of this invention include isomeric cyclic structures. It is to be understood accordingly that constitutional isomers of particular substituents are included within the scope of this invention, unless indicated otherwise. For example, the term "tetrazole" includes tetrazole, 2H-tetrazole, 3H-tetrazole, 4H-tetrazole and 5H-tetrazole.

Use in Bacterial Infection

The compounds of the present invention have valuable pharmacological properties and are useful in the treatment of diseases. In certain embodiments, compounds of the invention are useful in the treatment of bacterial infections.

The term "use" includes any one or more of the following embodiments of the invention, respectively: the use in the treatment of bacterial infections; the use for the manufacture of pharmaceutical compositions for use in the treatment of these diseases, e.g., in the manufacture of a medicament; methods of use of compounds of the invention in the treatment of these diseases; pharmaceutical preparations having compounds of the invention for the treatment of these diseases; and compounds of the invention for use in the treatment of these diseases; as appropriate and expedient, if not stated otherwise. In particular, diseases to be treated and are thus preferred for use of a compound of the present invention are selected from bacterial infections, as well as those diseases that depend on the activity of EF-Tu. The term "use" further includes embodiments of compositions herein which bind to an EF-Tu protein sufficiently to serve as tracers or labels, so that when coupled to a fluor or tag, or made radioactive, can be used as a research reagent or as a diagnostic or an imaging agent.

In certain embodiments, a compound of the present invention is used for treating EF-Tu-associated diseases, and use of the compound of the present invention as an inhibitor of any one or more EF-Tu proteins. It is envisioned that a use can be a treatment of inhibiting one or more isoforms of EF-Tu.

Assays

The inhibition of antibacterial activity by the compounds of the invention may be measured using a number of assays available in the art. An example of such an assay is the standard minimum inhibitory concentration (MIC) test conducted according to CSLI guidelines.

Pharmaceutical Compositions

The language "effective amount" of the compound is that amount necessary or sufficient to treat or prevent a bacterial infection, e.g. prevent the various morphological and somatic symptoms of a bacterial infection, and/or a disease or condition described herein. In an example, an effective amount of the compound of the invention is the amount sufficient to treat a bacterial infection in a subject. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of a bacterial infection. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

Compounds of the invention may be used in the treatment of states, disorders or diseases as described herein, or for the manufacture of pharmaceutical compositions for use in the treatment of these diseases. Methods of use of compounds of the present invention in the treatment of these diseases, or pharmaceutical preparations having compounds of the present invention for the treatment of these diseases.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories. Oral and/or IV administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount treats a bacterial infection.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

Synthetic Procedure

Compounds of the present invention are prepared from commonly available compounds using procedures known to those skilled in the art, including any one or more of the following conditions without limitation:

Within the scope of this text, only a readily removable group that is not a constituent of the particular desired end product of the compounds of the present invention is designated a "protecting group," unless the context indicates otherwise. The protection of functional groups by such protecting groups, the protecting groups themselves, and their cleavage reactions are described for example in standard reference works, such as e.g., Science of Synthesis: Houben-Weyl Methods of Molecular Transformation. Georg Thieme Verlag, Stuttgart, Germany. 2005. 41627 pp. (URL: http://www.science-of-synthesis.com (Electronic Version, 48 Volumes)); J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide and Derivate" (*Chemistry of Carbohydrates: Monosaccharides and Derivatives*), Georg Thieme Verlag, Stuttgart 1974. A characteristic of protecting groups is that they can be removed readily (i.e., without the occurrence of undesired secondary reactions) for example by solvolysis, reduction, photolysis or alternatively under physiological conditions (e.g., by enzymatic cleavage).

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g., the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g., by treating the compounds with an acid or a suitable anion exchange reagent. Internal salts of compounds of the present invention containing acid and basic salt-forming groups, e.g., a free carboxy group and a free amino group, may be formed, e.g., by the neutralisation of salts, such as acid addition salts, to the isoelectric point, e.g., with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g., using chromatographic methods, distribution methods, (re-) crystallization, and the like.

General Process Conditions

The following applies in general to all processes mentioned throughout this disclosure.

The process steps to synthesize the compounds of the invention can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g., in the $H^+$ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described in Science of Synthesis: Houben-Weyl Methods of Molecular Transformation. Georg Thieme Verlag, Stuttgart, Germany. 2005.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or f- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

Prodrugs

This invention also encompasses pharmaceutical compositions containing, and methods of treating bacterial infections through administering, pharmaceutically acceptable prodrugs of compounds of the compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

Any reference to a compound of the present invention is therefore to be understood as referring also to the corresponding pro-drugs of the compound of the present invention, as appropriate and expedient.

Combinations

A compound of the present invention may also be used in combination with other agents, e.g., an additional antibacterial compound that is or is not a compound of the invention, for treatment of a bacterial infection in a subject.

By the term "combination" is meant either a fixed combination in one dosage unit form, or a kit of parts for the combined administration where a compound of the present invention and a combination partner may be administered independently at the same time or separately within time intervals that especially allow that the combination partners show a cooperative, e.g., synergistic, effect, or any combination thereof A compound of the present invention may be used in combination with another antibacterial agent. The term "antibacterial agent" refers to any substance that is either bactericidal or bacteriostatic, i.e., capable of killing or inhibiting the growth of bacterial cells. Antibacterial agents include antibiotics, biocides, antimicrobials, and bacteriostatic agents. The known types of antibiotics include, e.g., cell wall synthesis inhibitors, cell membrane inhibitors, protein synthesis inhibitors and inhibitors that bind to or affect the synthesis of DNA or RNA. Numerous antibiotic agents suitable for use in the treatment of bacteria-related diseases and disorders, are known and disclosed, e.g. in The Physician's Desk Reference (PDR), Medical Economics Company (Montvale, N.J.), (53.sup.rd Ed.), 1999; Mayo Medical Center Formulary, Unabridged Version, Mayo Clinic (Rochester, Minn.), January 1998; Merck Index: An Encyclopedia of Chemicals, Drugs and Biologicals, (11.sup.th Ed.), Merck & Co., Inc. (Rahway, N.J.), 1989; University of Wisconsin Antimicrobial Use Guide, http://www.medsch.wisc.edu/clinsci/5amcg/amcg.html; Introduction on the Use of the Antibiotics Guideline, of Specific Antibiotic Classes, Thomas Jefferson University, http://jeffiine.tju.edu/CWIS/OAC/antibiotics_guide/intro.html; and references cited therein.

Examples of antibiotics for use in combination with the compounds of the invention include, but are not limited to, quinolone, macrolide, glycopeptide, oxazolidinone, β-lactams (including amoxicillin, ampicillin, bacampicillin, carbenicillin, cloxacillin, dicloxacillin, flucloxacillin, methicillin, mezlocillin, nafcillin, oxacillin, penicillin G, penicillin V, piperacillin, pivampicillin, pivmecillinam, ticarcillin, sulbactam, tazobactam, clavulanate), cephalosporins (cefaclor, cefadroxil, cefamandole, cefazolin, cefdinir, cefditoren, cefepime, cefixime, cefonicid, cefoperazone, cefotaxime, cefotetan, cefoxitin, cefpodoxime, cefprozil, ceftazidime, ceftibuten, ceftizoxime, ceftriaxone, cefuroxime, cephalexin, cephalothin, cephapirin, cephradine), aminoglycosides (including gentamycin, streptomycin, amikacin, kanamycin, viomycin, capreomycin), ethionamide, prothionamide, cycloserine, dapsone, clofazimine, tetracyclines (tetracycline, doxycycline, chlortetracycline, oxytetracycline, minocycline demeclocycline), oxazolidinones (linezolid, eperezolid), metronidazole, rifabutin, isoniazonid, ethambutol, and combinations thereof.

Examples of anti-viral agents for use in combination with the compounds of the invention include, but are not limited to, zidovudine, lamivudine, didanosine, zalcitabine, stavudine, abacavir, nevirapine, delavirdine, emtricitabine, efavirenz, saquinavir, ritonavir, indinavir, nelfinavir, amprenavir, tenofovir, adefovir, atazanavir, fosamprenavir, hydroxyurea, AL-721, ampligen, butylated hydroxytoluene; polymannoacetate, castanospermine; contracan; creme pharmatex, CS-87, penciclovir, famciclovir, acyclovir, cytofovir, ganciclovir, dextran sulfate, D-penicillamine trisodium phosphonoformate, fusidic acid, HPA-23, eflornithine, nonoxynol, pentamidine isethionate, peptide T, phenyloin, isoniazid, ribavirin, rifabutin, ansamycin, trimetrexate, SK-818, suramin, UA001, enfuvirtide, 41-derived peptides, antibodies to CD4, soluble CD4, CD4-containing molecules, CD4-IgG2, and combinations thereof.

Further examples of agents the compounds of the present invention can be used in combination with include, but are not limited to, free radical scavengers, ascorbic acid, Vitamin C, anti-cancer agents, chemotherapeutic agents, nonsteroidal anti-inflammatory drugs, steroidal anti-inflammatory drugs, anti-fungal agents, detoxifying agents, analgesics, bronchodilators, drugs for the treatment of vascular ischemia anti-body monoclonal agent, minoxidil for topical application for hair growth, diuretics, immunosuppressants, lymphokynes, α-and-β-interferon and combinations thereof.

The compound of the invention and any additional agent may be formulated in separate dosage forms. Alternatively, to decrease the number of dosage forms administered to a patient, the compound of the invention and any additional agent may be formulated together in any combination. For example, the compound of the invention inhibitor may be formulated in one dosage form and the additional agent may be formulated together in another dosage form. Any separate dosage forms may be administered at the same time or different times.

Alternatively, a composition of this invention comprises an additional agent as described herein. Each component may be present in individual compositions, combination compositions, or in a single composition.

Exemplification of the Invention

The invention is further illustrated by the following examples, which should not be construed as further limiting. The practice of the present invention will employ, unless otherwise indicated, conventional techniques of cell biology, cell culture, molecular biology, transgenic biology, microbiology and immunology, which are within the skill of the art.

General Synthesis Methods

All starting materials, building blocks, reagents, acids, bases, dehydrating agents, solvents, and catalysts utilized to synthesize the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

EXAMPLES

Definitions

A, Å Ankstrom
ACN acetonitrile
AcOH acetic acid
aq aqueous
bnBr benzylbromide
boc tert-butoxycarbonyl
C Celsius
cat. catalytic
CDI cabonyldiimidazole
CSA camphorsulfonic acid
conc. concentrated
$C_2CO_3$ cesium carbonate
Da Daltons
deg degrees
DIBAL, DIBAL-H diisobutylaluminum hydride
DIPEA diisopropylethylamine
DIPC N,N'-diisopropylcarbodiimide
DMF N, N-dimethylformamide
DMI 1,3 dimethyl-2-imidazolidinone
DMP Dess-Martin periodinane
DCC N,N-dicyclohexylcarbodiimide
DCE dichloroethane
DCM dichloromethane
DMAP 4-dimethylaminopyridine
DMSO dimethylsulfoxide
EtOAc ethyl acetate
EtOH ethanol
eq equivalents
g gas
Grubbs II 1,3-bis(2,4,6-trimethylphenyl)-2-(imidazolidinylidene)(dichlorophenylmethylene)(tricyclohexyl phosphine)ruthenium
h hours
HATU O-(7-azabenzotriazol-1-yl)-N,N,N',N'-tetramethyluronium hexafluorophosphate
HMPA hexamethlphosphoramide
hep heptane
HCl hydrochloric acid
inh. inhibition
imid. Imidazole
K Kelvin
KHMDS potassium hexamethyldisilylazide
$K_2CO_3$ potassium carbonate
LDA lithiumdiisopropylamine
$LiBH_4$ lithium borohydride
LHMDS lithiumhexamethyldisilylazide
LC liquid chromatography
LC/MS liquid chromatography mass spectrum
M molar
MeCN acetonitrile
MeOH methanol
$MgSO_4$ magnesium sulfate
MHz megahertz
min minutes
mol. sieves molecular sieves
$NaBH_4$ sodium borohydride
N normal
NMR nuclear magnetic resonance
Pd/C palladium on carbon
PEG(750) O-(2-aminoethyl)-O'-methyl polyethylene glycol 750; $NH_2(CH_2CH_2O)_nCH_3$; CAS#[80506-64-5]; Fluka 07964; AVERAGE MW=750
PS polystyrene
Py pyridine
PPM parts per million
RP reverse phase
RT room temperature
$R_t$ retention time
s solid
sat. saturated
TBS tert-butyldimethylsilyl
TMS trimethylsilyl
TBAF tetrabutylammonum fluoride
TBTU O-benzotriazol-1-yl-N,N,N,N'-tetramethyluronium tetrafluoroborate
TLC thin-layer chromatography
TEA triethylamine
TFA trifluoroacetic acid
THF tetrahydrofuran
h hours
min minutes
m/z mass to charge
MS mass spectrum
HRMS high resolution mass spectrum
NMR nuclear magnetic resonance

Analytical Methods

NMR:
proton spectra are recorded on a Bruker 400 MHz ultrashield spectrometer unless otherwise noted. Chemical shifts are reported in ppm relative to methanol (δ 3.31), dimethyl sulfoxide (δ 2.50), or chloroform (δ 7.26).

LC/MS:

Method 1: compounds are analyzed on an Inertsil ODS-3 column (C18, 50×4.6 mm, 3 μm) with a 2 min gradient elution (20-80% acetonitrile/H$_2$O/5 mM ammonium formate) and a flow rate of 4 mL/min.

Method 5: GENERAL LC/MS method with acid mobile phase (0.1% formic acid) and fast gradient. Electrospray mass spectra (+) and (−), DAD-UV chromatogram 200-400 nm, scan range 120-1500 Da. Gradient: 20-80% MeCN/H$_2$O in 2 min (2 mL/min), 2 μL injection. Column. Inertsil ODS3 C-18, 3 cm×33 mm×3.0 μm, 40 deg C.

Method 6: GENERAL LC/MS method with neutral mobile phase (5 mM NH$_4^+$HCOO$^−$) and fast (20-80%) gradient. Electrospray mass spectra (+) and (−), DAD-UV chromatogram 200-400 nm, scan range 120-1500 Da. Gradient: 20-80% MeCN/H$_2$O in 2 min (2 mL/min), 2 μL injection. Column: Inertsil ODS3 C-18, 3 cm×33 mm×3.0 μm, 40 deg C.

Method 7: LC/MS method for NON-POLAR (greasy) compounds with acid mobile phase (0.1% formic acid) and fast (40-90%) gradient. Electrospray mass spectra (+) and (−), DAD-UV chromatogram 200-400 nm, scan range 120-1500 Da. Gradient: 40-90% MeCN/H$_2$O in 2 min (2 mL/min), 2 μL injection. Column. Inertsil C8-3, 3 cm×33 mm×3.0 μm, 40 deg C.

Method 8: LC/MS method for NON-POLAR (greasy) compounds with neutral mobile phase (5 mM NH$_4^+$HCOO$^−$) and fast (40-90%) gradient. Electrospray mass spectra (+) and (−), DAD-UV chromatogram 200-400 nm, scan range 120-1500 Da. Gradient: 40-90% MeCN/H$_2$O in 2 min (2 mL/min), 2 μL injection. Column. Inertsil C8-3, 3.0 cm×33 mm×3.0 μm, 40 deg C.

Method 9: LC/MS method with broad range (5-95%) gradient with acid mobile phase (0.1% Formic Acid). Electrospray mass spectra (+) and (−), DAD-UV chromatogram 200-400 nm, scan range 120-1500 Da. Gradient: 5-95% MeCN/H$_2$O in 2 min (2 mL/min), 2 μL injection. Column. Inertsil C8-3, 3.0 cm×33 mm×3.0 μm, 40 deg C.

Method 10: LC/MS method with broad range (5-95%) gradient with neutral mobile phase (5 mM NH$_4^+$HCOO$^−$). Electrospray mass spectra (+) and (−), DAD-UV chromatogram 200-400 nm, scan range 120-1500 Da. Gradient: 5-95% MeCN/H$_2$O in 2 min (2 mL/min), 2 μL injection. Column: Inertsil C8-3, 3 cm×433 mm×3.0 μm, 40 deg C.

Method 11: LC/MS method for POLAR compounds with acid mobile phase (0.1% formic acid) and slow (0-100%) gradient. Electrospray mass spectra (+) and (−), DAD-UV chromatogram 200-400 nm, scan range 120-1500 Da. Gradient: 0-100% MeCN/H$_2$O in 2 min (2 mL/min), 2 μL injection. Column: Inertsil ODS3 (C-18, 3 cm×33 mm×3.0 μm, 40 degree C.)

Method 12: LC/MS method for POLAR compounds with neutral mobile phase (5 mM NH$_4^+$HCOO$^−$) and slow (0-100%) gradient. Electrospray mass spectra (+) and (−), DAD-UV chromatogram 200-400 nm, scan range 120-1500 Da. Gradient: 0-100% MeCN/H$_2$O in 2 min (2 mL/min), 2 μL injection. Column: Inertsil ODS-3 (C-18, 3 cm×33 mm×3.0 μm, 40 deg C.

Method 13: Compounds are analyzed on an Inertsil ODS-3 column (C8, 30 mm×3.0 mm, 3.0 um) with a 2 min gradient elution (5-90% acetonitrile/H$_2$O/5 mM ammonium formate) and a flow rate of 2 mL/min.

Method 14: Compounds are analyzed on an Inertsil ODS-3 column (C8, 30 mm×3.0 mm, 3.0 um) with a 2 min gradient elution (5-90% acetonitrile/H$_2$O/0.1% formic acid) and a flow rate of 2 mL/min.

HPLC purification utilizes a C8 or C18 column (30×100 mm, 5 um, brand: Sunfire or XTerra) and is performed with an appropriate gradient using two methods (unless otherwise noted). Method 1 consists of 0.1% TFA in 5%-95% ACN in H$_2$O. Method 2 consists of 10 mM NH$_4$OH in 5%-95% ACN in H$_2$O.

LC analysis utilizes a liquid chromatography-UV detection (LC-UV) using a Agilent 1100 liquid chromatograph. LC conditions are as follows: column: Atlantis C18 (Waters, Inc.), 15 cm×4.6 mm×5 μm; column temperature: ambient; flow rate: 1.4 mL/min; injection volume: 3.0 μL; gradient: A=0.1% trifluoroacetic acid (TFA) in water, B=0.05% trifluoroacetic Acid (TFA) in acetonitrile, 0-95% B in 19.0 min, 1.8 min hold.

General Scheme 1:

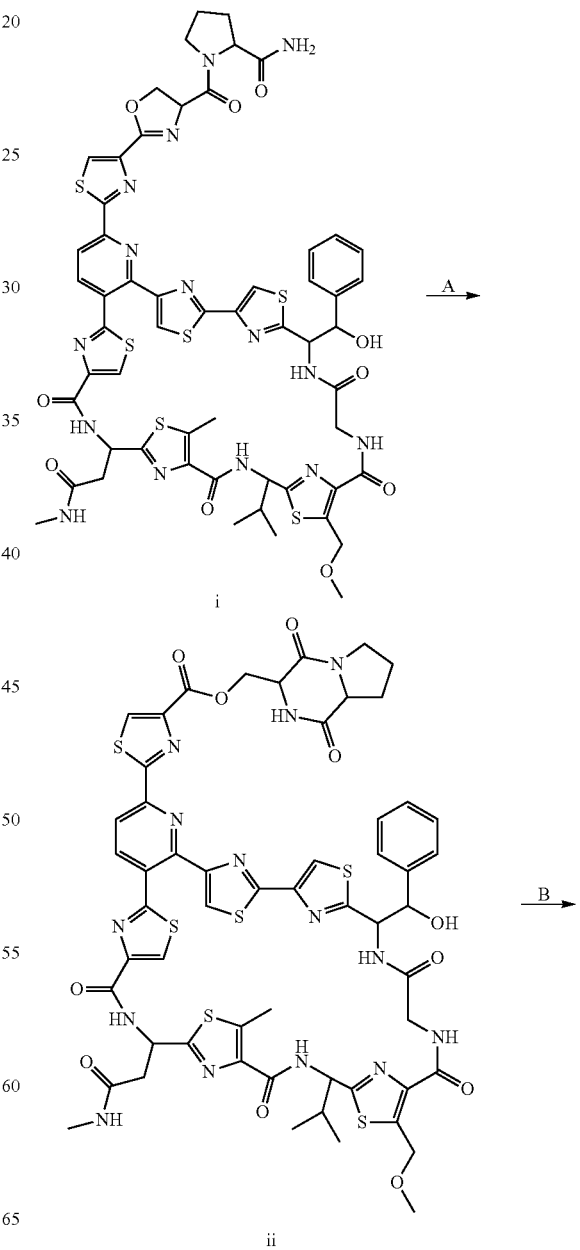

i ii

87
-continued
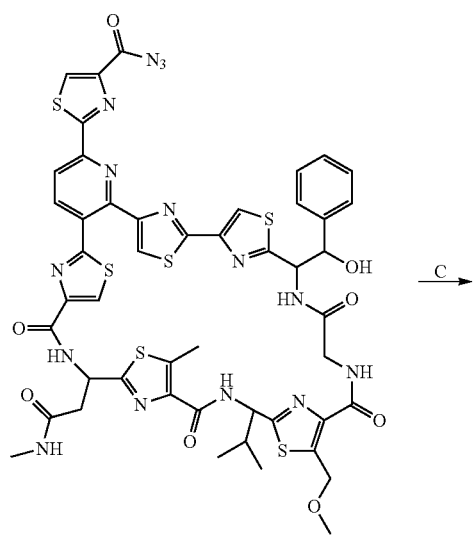
iii
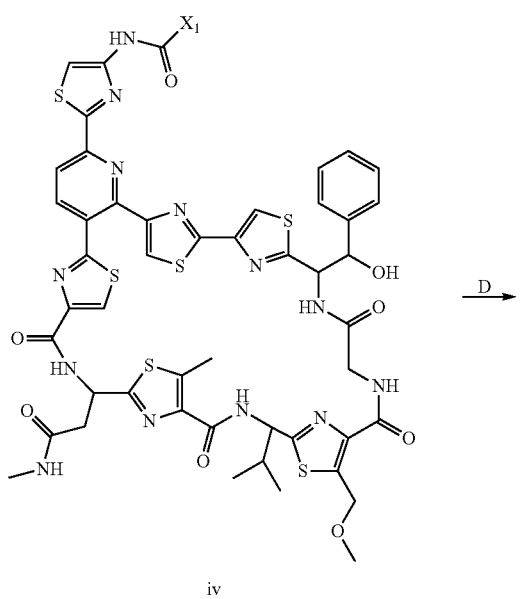
iv
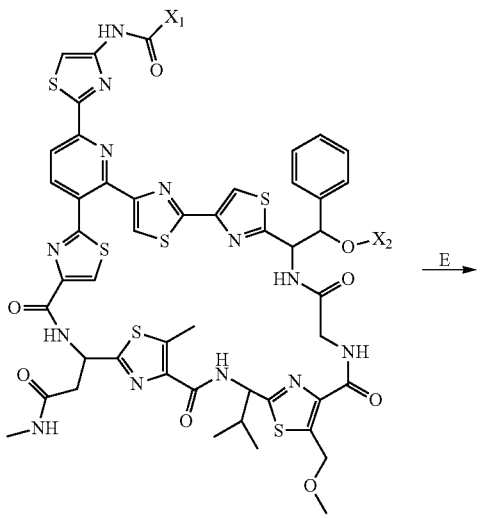
v
88
-continued
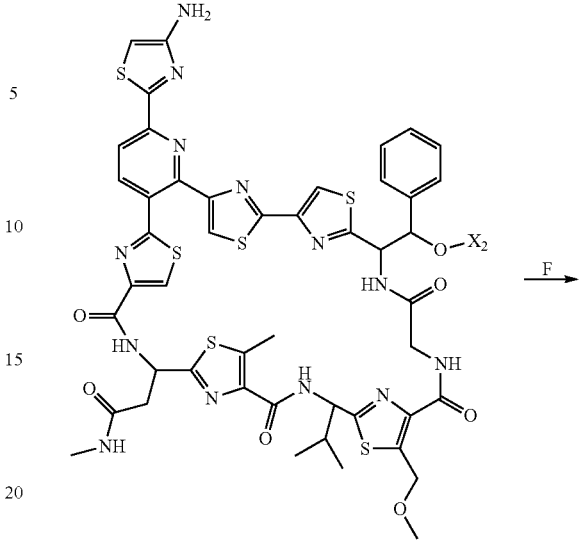
vi
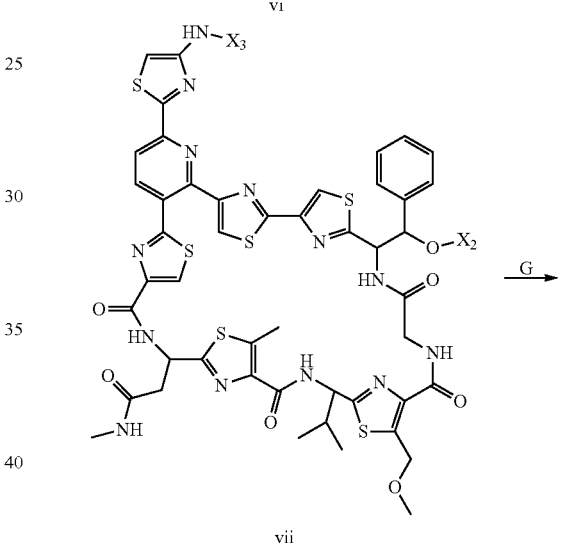
vii
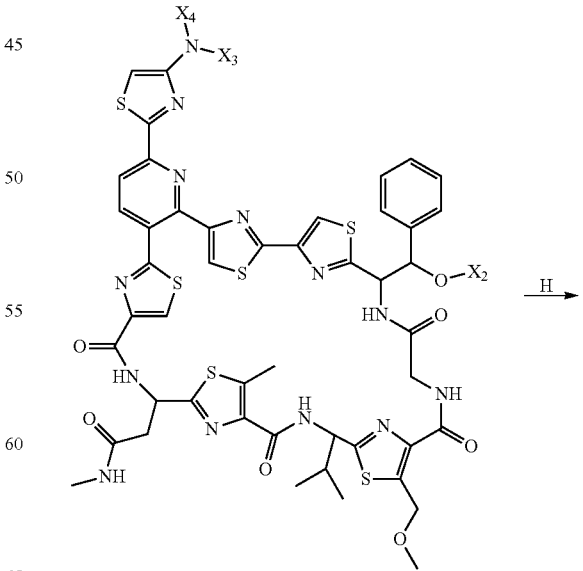
viii -continued

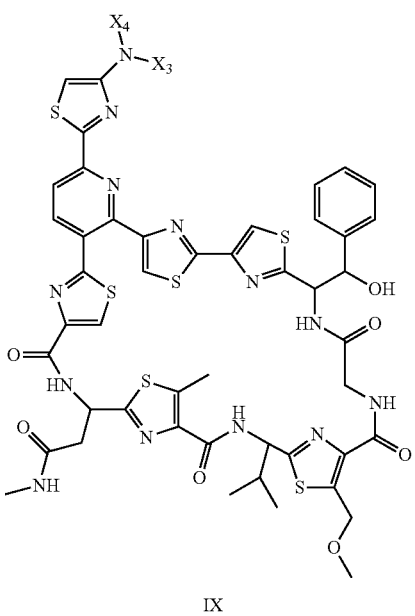

IX

The compound of general formula (i) may be prepared via synthetic methods well known to those skilled in the art, or alternatively isolated from a fermentation broth. See, for example, U.S. Pat. No. 5,202,241. The compound of general structural formula (ii) may be prepared by process A by the acid or base mediated rearrangement of compound (i) in the presence of water and a suitable acid or base. The compound of general formula (iii) may be prepared in process B from (ii) directly via reaction with azide or alternatively through a multi step process which includes removal of the ester functionality through hydrolysis with a suitable base or acid, activation of the carboxylic acid moiety using a suitable activation agent, and reaction with a suitable reagent such as azide. Azides represented by formula (iii) are known in the art and are readily synthesized by standard procedures commonly employed in the art. The compound of general formula (iv) may be prepared by reaction of the azide (iii) with a nucleophile, alcohol, amine, or protecting group ($X_1$). A suitable protecting group can be selected by those skilled in the art. Protecting groups are selected so that they are suitable for the depicted transformations and can be removed following the synthesis with little or no loss of yield. The introduction and selective removal of protecting groups are taught in Greene and Wuts, "Protective Groups in Organic Synthesis", John Wiley & Sons (1991). The compound of general structural formula (v) may be prepared by reacting compound (iv) with a reactive reagent such as an electrophile, alkylating agent, acylating agent, or protecting group ($X_2$) to afford compound (v). The compound of general structure (vi) can be prepared by reacting compound (v) with acid, base, a nucleophile, or electrophile to remove the protecting group ($X_1$). The compound of general structure (vii) can be prepared by reacting compound (vi) with a suitable electrophile, alkylating agent, or acylating agent ($X_3$). The compound of general structure (viii) can be prepared by reacting compound (vii) with a suitable electrophile, alkylating agent, or acylating agent ($X_4$). The compound of general structure (ix) can be prepared by reacting compound (viii) with acid, base, a nucleophile, or electrophile to remove any remaining protecting groups. Alternatively, any of these steps (A-H) may be performed in a different order, or with some steps removed or slightly altered, which is obvious to those skilled in the art.

General Scheme 2:

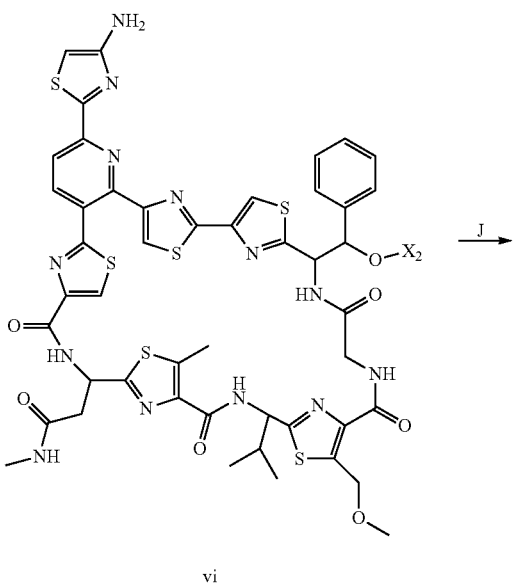

vi

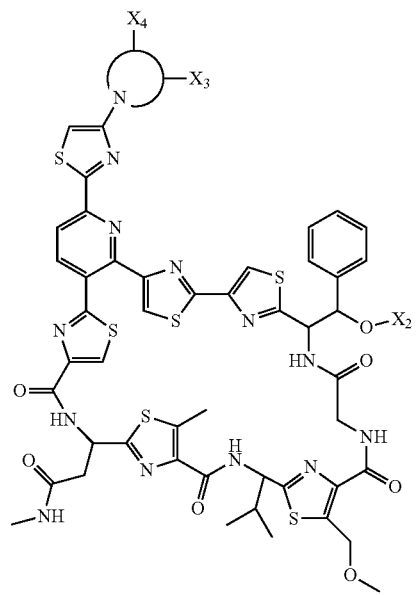

x

91

-continued

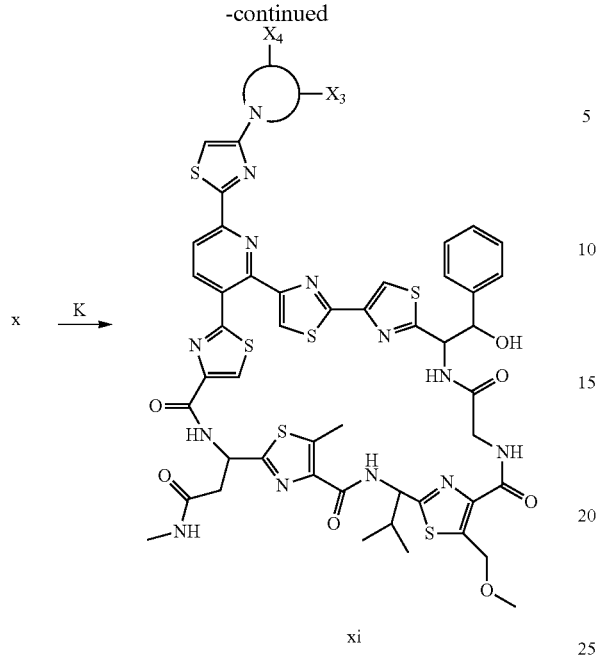

xi

Intermediate vi can also be cyclized to form a heterocycle or heteroaromatic ring according to process J through an alkylation, acyation, cyclization, transition metal-mediated coupling, or condensation which may be acid or base catalyzed to form x. Compound x can be further derivatized through alkylation, acylation, transition metal-mediated coupling, etc. and the protecting groups removed through process K to provide xi.

92

Example 1

Preparation of Diacid 3 of Table A

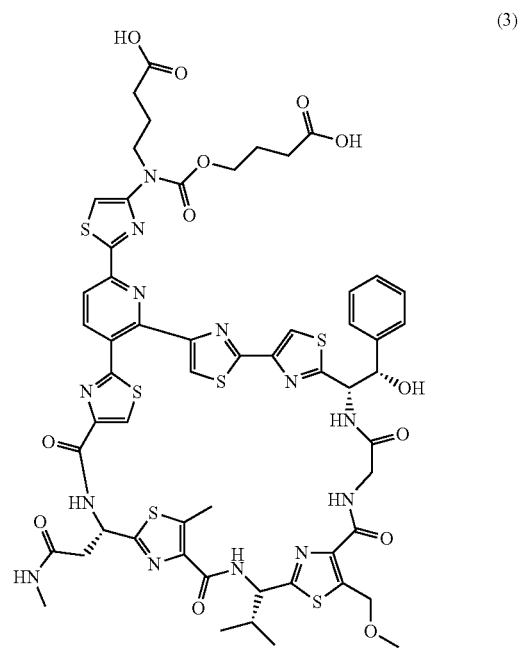

(3)

Scheme 3: Preparation of Diacid Compound 3 of Table A:

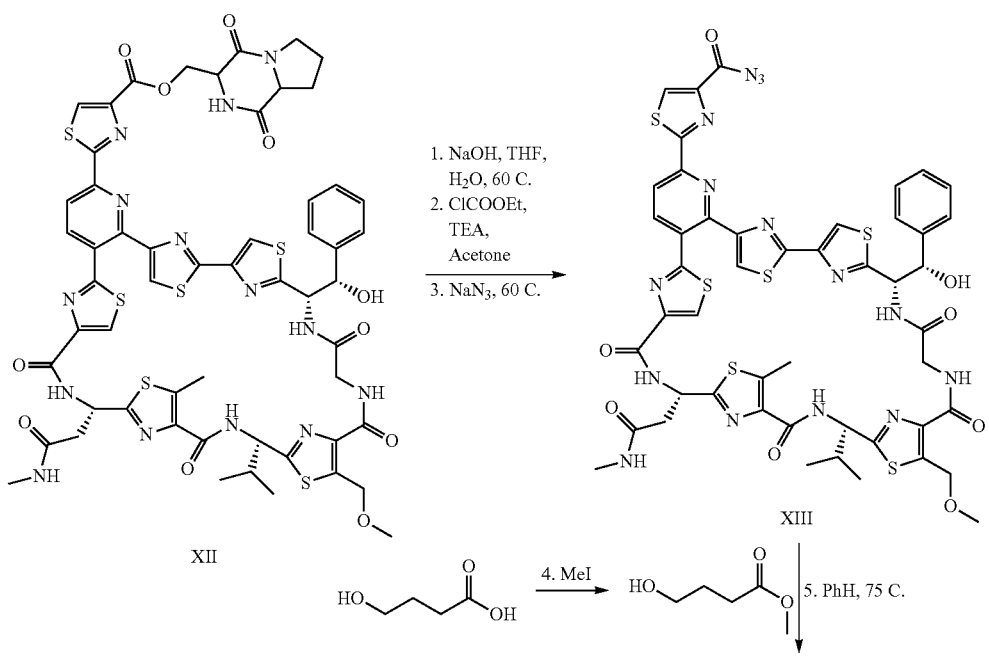

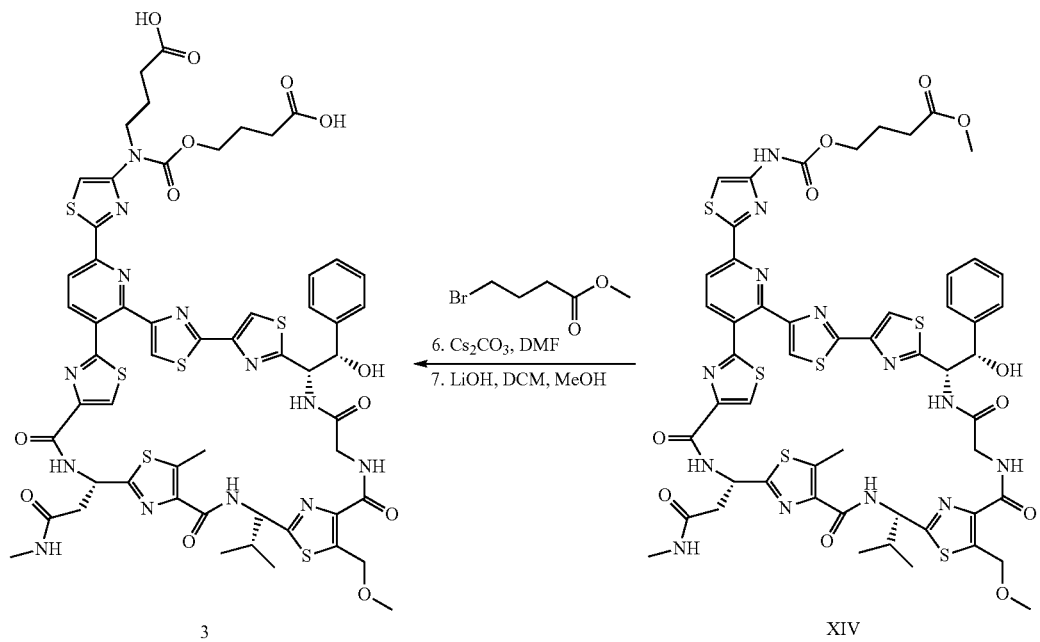

Steps 1-3:

To a solution of XII (3.1 g, 2.4 mmol) in $(CH_3)_2CO$ (350 mL) and $H_2O$ (40 mL), is added NaOH crystals (0.192 g, 4.8 mmol). The reaction mixture is sonicated and stirred at 22° C. for 1 hour (LC/MS: m/z [M+H]$^+$1125, $R_t$=1.12 min, method 1). The reaction mixture is then cooled to 0° C. and EtOCOCl (17.8 mL, 192 mmol) is added via syringe. After stirring reaction mixture at 0° C. for 1.5 hours, the reaction shows the acyl carbonate intermediate (MS m/z 1197 [M+H]$^+$). NaN$_3$ solid (6.3 g, 96 mmol) is added to the reaction mixture and is stirred at 22° C. for 12 hours. 15 g of $SiO_2$ is added and all solvents are evaporated in vacuo. The solid is purified by flash chromatography, eluting with 100% EtOAc to provide 3.4 g (quant yield), of a cream solid, XIII. MS m/z 1167 (M+$H_2O$).

Step 4:

To a solution of the acid sodium salt (8 g, 63 mmol) in DMF (100 mL) is added MeI (7.9 mL, 126 mmol) and reaction mixture is stirred for 5 days at 22° C. The excess solvents are removed under reduced pressure. The residue is diluted with EtOAc and washed with aqueous brine solution. The organic layers are combined and dried over $Na_2SO_4$, filtered and concentrated to provide 6.2 g (83%) of a yellow oil, 4-hydroxy-butyric acid methyl ester.

Step 5:

To a solution of XIII (3 g, 2.6 mmol) in PhMe (100 mL) is added 4-hydroxy-butyric acid methyl ester (1.2 g, 10.4 mmol) and the reaction mixture is stirred at 75° C. for 12 hours. 7 g of $SiO_2$ is added to the mix and the solvents are concentrated under reduced pressure. The solid is purified by flash chromatography, eluting with 100% EtOAc to provide 3.82 g (quant. yield), of a yellow solid, XIV. MS m/z 1240 (M+H)$^+$.

Step 6:

To a solution of XIV (1.8 g, 0.15 mmol) in DMF (50 mL), is added 4-bromo-butyric acid methyl ester (1 g, 0.87 mmol) and $Cs_2CO_3$ (800 mg, 0.48 mmol). The reaction is stirred at 22° C. for 48 hours. 5 g $SiO_2$ is added and all solvents are evaporated in vacuo. The solid is purified by flash chromatography, eluting with MeOH/DCM (0-10%) to provide 1.5 g (75%), of a yellow solid. MS m/z 1357 (M+$H_2O$).

Step 7:

To a solution of the diester (250 mg, 0.187 mmol) in MeOH (10 mL) and $H_2O$ (2 mL) is added NaOH crystals (37 mg, 0.933 mmol) and the reaction mixture is stirred for 72 hours at 22° C. 6 g of $SiO_2$ is added and the solvents are concentrated under reduced pressure. The solid is purified by flash chromatography, eluting with MeOH/DCM (5-10%) then to 10% MeOH/DCM with 1% AcOH to provide 0.2 g of a yellow oil. The yellow oil is purified by Gilson HPLC eluting with ACN/$H_2O$ (5-50%) with 3% n-propanol. Lypholization for 12 h provides 4 mg (16%) of a white solid, 3. LC/MS: m/z 1329 [M+$H_2O$]$^+$, method 1. LC: $R_t$=8.84 min, HRMS (ES$^+$) $C_{56}H_{57}N_{13}O_{13}S_6$: Calc.: 1312.2601 [M+H]$^+$. Found: 1312.2637. $^1$H NMR (DMSO-d6, 600 MHz, 300 K) δ 9.047 (d, 1H), 8.698 (d, 1H), 8.683 (d, 1H), 8.605 (s, 1H), 8.459 (dd, 1H), 8.381 (d, 1H), 8.265 (s, 1H), 8.238 (d, 1H), 7.758 (s, 1H), 7.388 (m, 1H), 7.361 (s, 1H), 7.321 (m, 1H), 7.289 (m, 1H), 7.239 (m, 1H), 6.06 (b, 1H), 5.295 (m, 1H), 5.237 (t, 1H), 5.211 (dd, 1H), 4.998 (d, 1H), 4.979 (s, 2H), 4.272-3.787 (dd, 2H), 4.163 (t, 2H), 4.007 (b, 2H), 3.391 (s, 3H), 2.717-1.298 (dd, 2H), 2.589 (s, 3H), 2.479 (d, 3H), 2.336 (t, 2H), 2.303 (t, 2H), 2.169 (m, 1H), 1.900 (m, 2H), 1.878 (m, 2H), 0.881-0.846 (d, 3H).

Example 2

Preparation of Diacid 4 of Table A

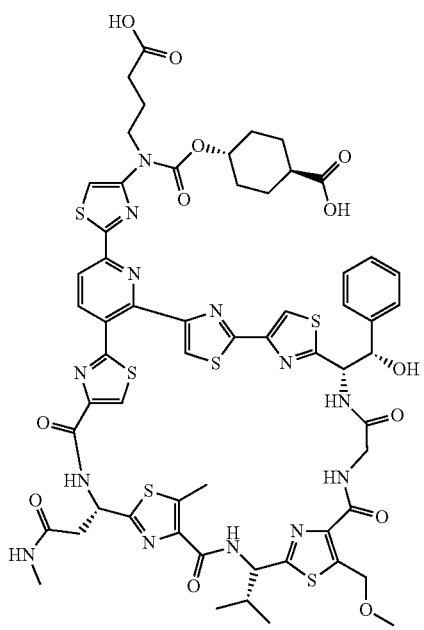

(4)

Step 1:

To a suspension of acylazide (XIII, 0.600 g, 0.522 mmol) in toluene (20 mL) is added trans-4-hydroxy-cyclohexane carboxylic acid ethyl ester (0.134 g, 0.778 mmol) and the mixture is stirred at 80° C. for 5 h. The reaction is concentrated in vacuo and the crude product is purified by flash chromatography (MeOH/DCM) to yield 0.236 g (0.182 mmol, 35%) of the ester.

Step 2:

To a solution of the ester (125 mg, 0.098 mmol) in DMF (0.8 mL), is added methyl 4-bromobutyrate (67 uL, 0.588 mmol) and Cs$_2$CO$_3$ (112 mg, 0.341 mmol). The reaction is stirred at rt for 18 hours. The reaction mixture is concentrated, and the residue is purified by flash chromatography, eluting with MeOH/DCM (0-10%) to provide 100 mg (74.2%), of a yellow solid, the diester. MS, m/z 1381 (M+H)$^+$.

Step 3:

To a solution of the diester (180 mg, 0.130 mmol) in MeOH (3.6 mL) and THF (0.9 mL) is added 3 N NaOH (0.45 mL, 1.30 mmol) and the reaction mixture is stirred for 7 hours at rt. The reaction mixture is neutralized with solid NH$_4$Cl (70 mg, 1.30 mmol). The mixture is then concentrated under reduced pressure. The yellow solid is purified by Gilson HPLC eluting with ACN/H$_2$O with 0.1% TFA (gradient elution: 30-80%). Lyophylization for 12 h provides 54 mg of light yellow solid, 4. LC: R$_t$=11.68 min; HRMS (ES$^+$) C$_{59}$H$_{61}$N$_{13}$O$_{13}$S$_6$: Calc.: 1352.2914 [M+H]$^+$. Found: 1352.2878.

Example 3

Preparation of Diacid 5 of Table A

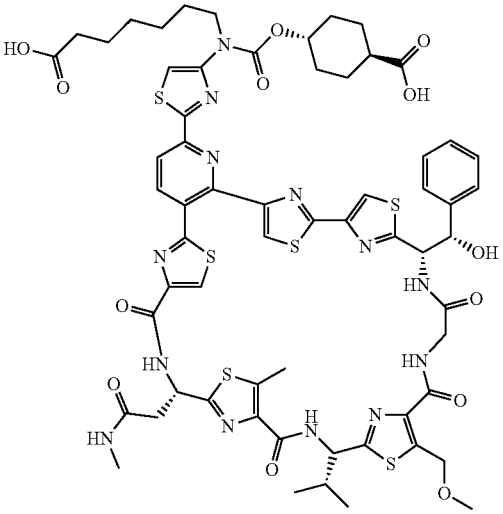

(5)

Step 1:

To a solution of the cyclohexyl ester (Example 2, step 1, 300 mg, 0.234 mmol) in DMF (2.1 mL), is added ethyl 7-bromo-heptanoate (282 uL, 1.40 mmol) and Cs$_2$CO$_3$ (267 mg, 0.819 mmol). The reaction is stirred at rt for 18 hours. The reaction mixture is concentrated, and the residue is purified by flash chromatography, eluting with MeOH/DCM (0-10%) to provide 210 mg of diester. MS m/z 1437 (M+H)$^+$.

Step 2:

To a solution of the diester (210 mg, 0.146 mmol) in MeOH (4.5 mL) and THF (1.5 mL) is added 3N NaOH (0.49 mL, 1.46 mmol) and the reaction mixture is stirred for 18 hours at rt. The reaction mixture is neutralized with solid NH$_4$Cl (81 mg, 1.50 mmol), and is concentrated under reduced pressure. The yellow solid is purified by Gilson HPLC eluting with ACN/H$_2$O with 0.1% TFA (30-80%). Lyophylization for 12 h provides 86 mg of light yellow solid, 5. LC: R$_t$=12.82 min, HRMS (ES$^+$) C$_{62}$H$_{67}$N$_{13}$O$_{13}$S$_6$: Calc.: 1394.3384 [M+H]$^+$. Found: 1394.3356.

Example 4

Preparation of Diacid 6 of Table A

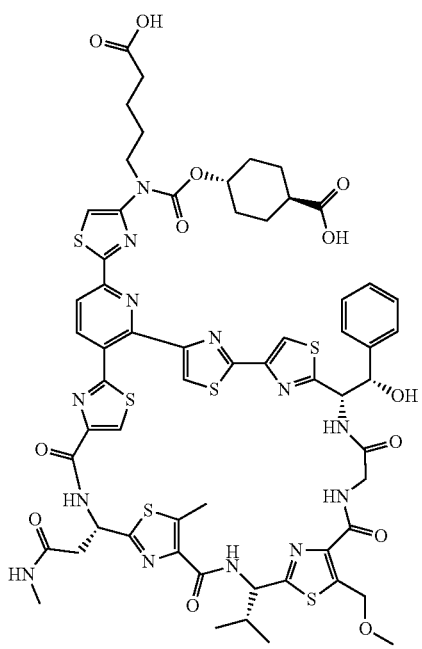

(6)

Compound 6 is prepared according to example 1 and scheme 3.

Step 1:

To a solution of XIII (1 g, 0.87 mmol) in dioxane (80 mL) is added trans-4-hydroxy cyclohexane carboxylic acid methyl ester (0.46 g, 2.9 mmol) and the reaction mixture is stirred at 80° C. for 4 h. SiO$_2$ is added to the mix and the solvents are concentrated under reduced pressure. The solid is purified by flash chromatography, eluting with 10% DCM/MeOH to provide 530 mg (47.7% yield), of a yellow solid, the urethane. MS m/z 1280 (M+H)$^+$.

Step 2:

To a solution of the urethane (300 mg, 0.234 mmol) and Cs$_2$CO$_3$ (267 mg, 0.820 mmol) in DMF (2 mL), is added methyl 5-bromovalerate (0.20 mL, 1.404 mmol). The reaction is stirred at rt for 12 h, filtered and concentrated. The residue is purified by flash chromatography, eluting with MeOH/DCM (gradient: 0-10%) to provide 270 mg (82.5%), of a yellow solid. MS m/z 1395 (M+H)$^+$.

Step 3:

To a solution of the diester (270 mg, 0.194 mmol) in MeOH (6.5 mL) and THF (2.5 mL) is added 3 N NaOH (0.65 mg, 1.94 mmol) and the reaction mixture is stirred for 12 h at rt. The reaction is neutralized with NH$_4$Cl until pH=6-7. The reaction is concentrated under vacuum. The residue is dissolved in DMF/H$_2$O, purified with HPLC (gradient elution MeCN/H$_2$O, 0.1% TFA modifier), and lypholized for 12 h to provide 98.5 mg (37.2%) of a light yellow solid, 6. HRMS (ES$^+$) C$_{60}$H$_{63}$N$_{13}$O$_{13}$S$_6$: Calc.: 1366.3071 [M+H]$^+$. Found: 1366.3009. LC/MS: m/z [M+2H]$^+$1367, R$_t$=1.41 min (method 14). $^1$H NMR: (600 MHz, DMSO-d6) δ 9.132 (d, 1H), 8.707 (d, 1H), 8.681 (d, 1H), 8.604 (s, 1H), 8.465 (dd, 1H), 8.387 (d, 1H), 8.257 (s, 1H), 8.217 (d, 1H), 7.713 (s, 1H), 7.394 (m, 1H), 7.354 (s, 1H), 7.322 (d, 2H), 7.285 (t, 2H), 7.235 (t, 1H), 6.175 (b, 1H), 5.294 (m, 1H), 5.239 (t, 1H), 5.213 (dd, 1H), 5.007 (d, 1H), 4.983 (d, 2H), 4.666 (m, 1H), 4.287-3.796 (dd, 2H), 3.982 (b, 2H), 3.392 (s, 3H), 2.794-1.285 (dd, 2H), 2.592 (s, 3H), 2.479 (d, 3H), 2.277 (t, 2H), 2.256 (m, 1H), 2.170 (m, 1H), 2.010-1.476 (m, 4H), 1.931-1.476 (m, 4H), 1.686 (m, 2H), 1.575 (m, 2H), 0.885 (d, 3H), 0.848 (d, 3H).

Example 5

Preparation of Diacid 7 of Table A

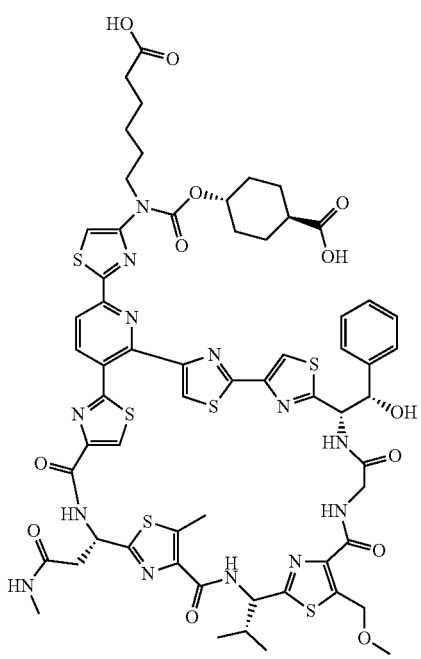

(7)

Compound 7 is prepared according to the procedures described in example 2. LC/MS: m/z [M+2H]$^+$1381, R$_t$=1.43 min (method 14).

Example 6

Preparation of Diacid 8 of Table A

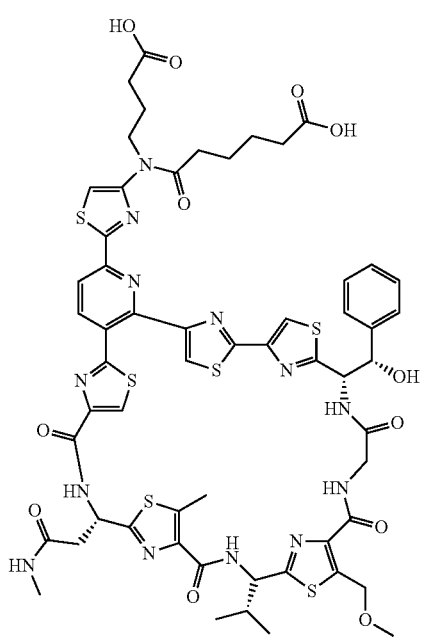
(8)

Compound 8 is prepared according to the procedures described in example 8. LC/MS: m/z [M+H]$^+$ 1310, R$_t$=1.2 min (method 5). $^1$H NMR (DMSO-d6, 400 MHz) δ ppm 0.78-0.94 (m, 6H) 1.22-1.32 (br, 1H), 1.40-1.60 (br, 4H), 1.70-1.85 (br, 2H), 2.10-2.37 (m, 7H), 2.48 (s, 3H), 2.59 (s, 3H), 2.65-2.78 (m, 1H), 3.39 (s, 3H), 3.69-3.85 (m, 3H), 4.21-4.35 (m, 1H), 4.96-5.03 (br, 3H), 5.17-5.35 (m, 3H), 6.00-6.12 (br, 1H), 7.22-7.44 (m, 7H), 7.96 (s, 1H), 8.20-8.31 (m, 2H), 8.36-8.43 (m, 1H), 8.43-8.51 (m, 1H), 8.61 (s, 1H), 8.64-8.76 (m, 2H), 9.05 (d, J=7.71 Hz, 1H), 11.87-12.22 (br, 2H).

Example 7

Preparation of Diacid 9 of Table A

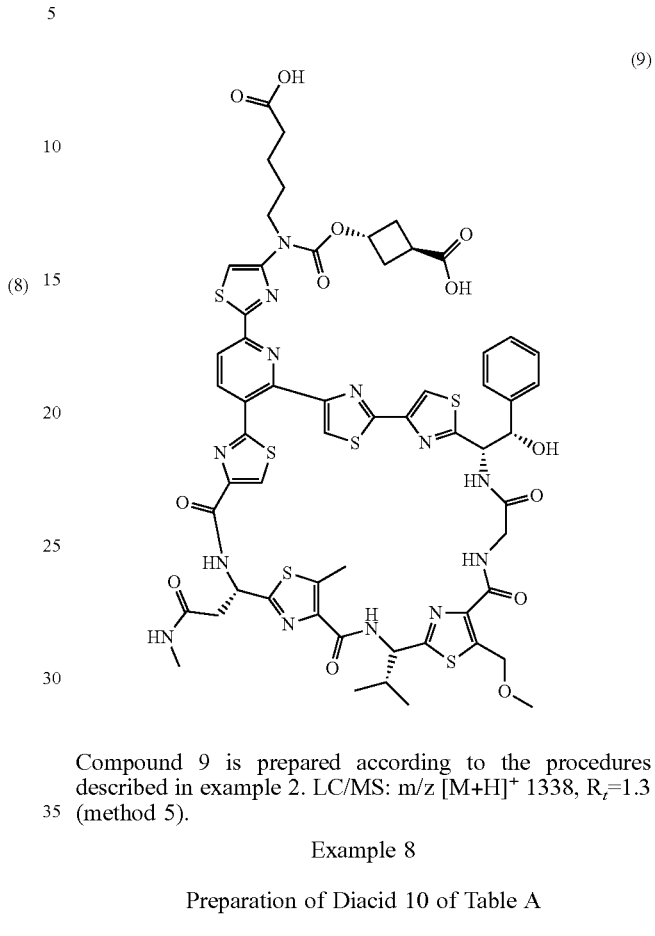
(9)

Compound 9 is prepared according to the procedures described in example 2. LC/MS: m/z [M+H]$^+$ 1338, R$_t$=1.3 (method 5).

Example 8

Preparation of Diacid 10 of Table A

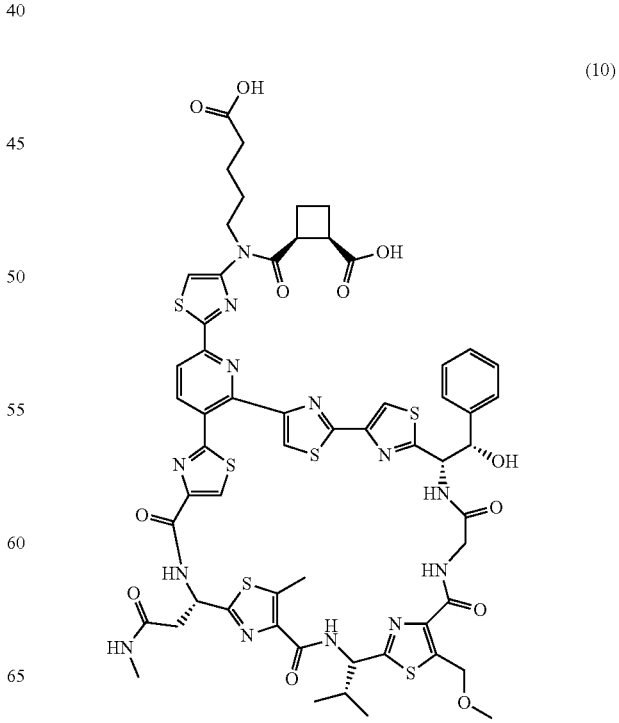
(10)

Scheme 4:
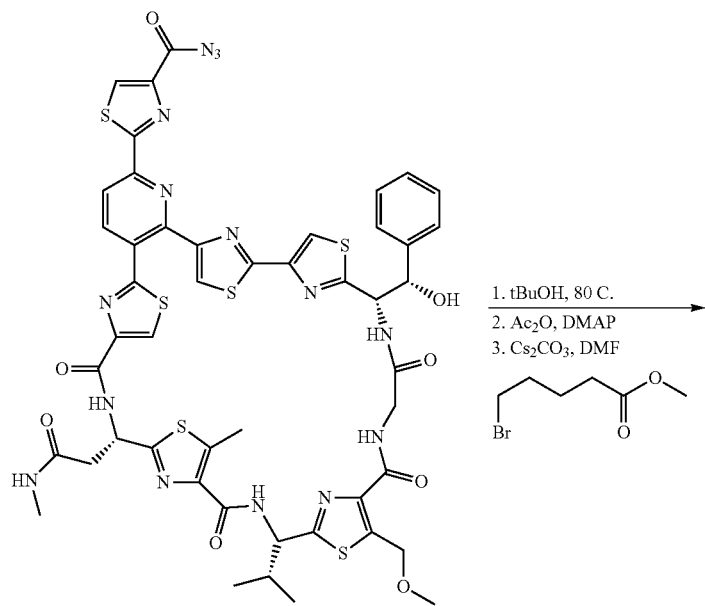
1. tBuOH, 80 C.
2. Ac₂O, DMAP
3. Cs₂CO₃, DMF
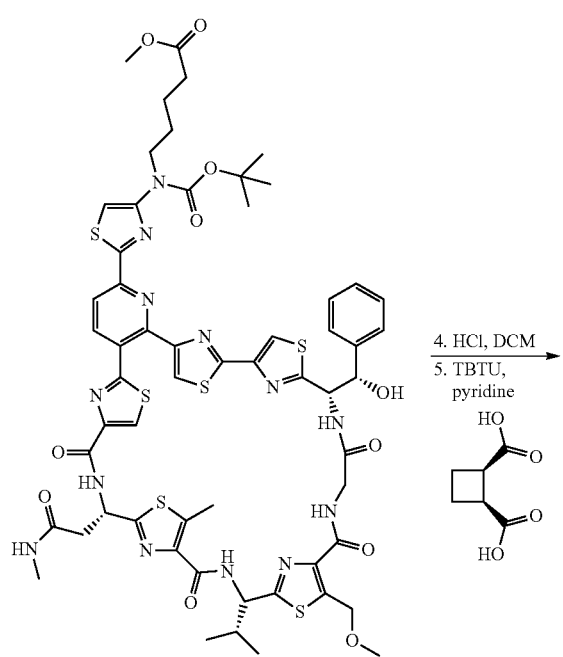
4. HCl, DCM
5. TBTU, pyridine

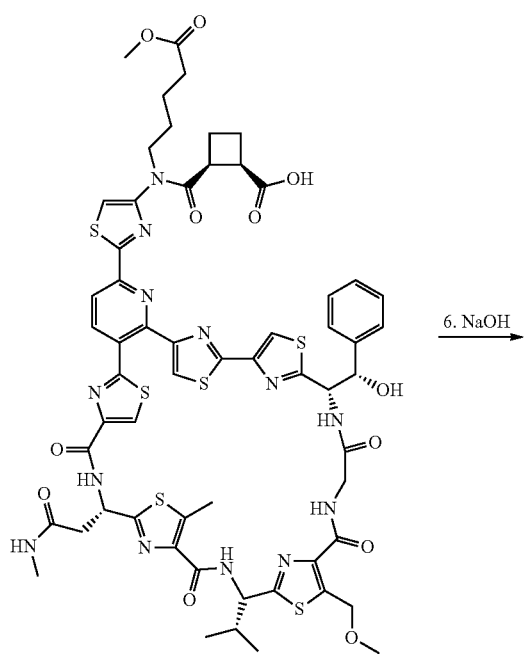
6. NaOH →
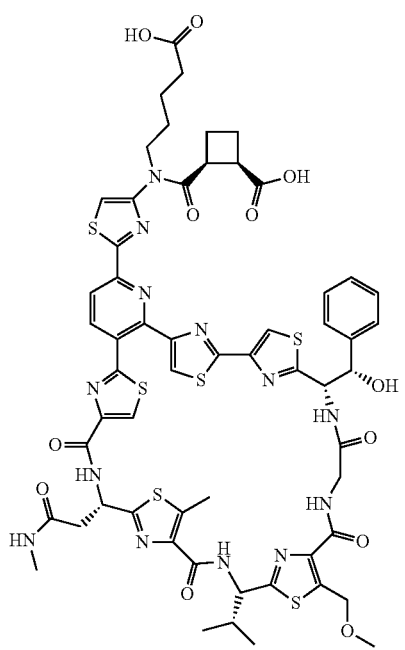

Step 1:

A suspension of acyl-azide (XIII, 920 mg) is heated (80° C.) in t-BuOH (100 g). After 2 h complete dissolution occurs and after 12 h the reaction appears complete by LC/MS. The solution is concentrated directly onto SiO$_2$ and chromatographed (gradient elution: 50-70% EtOAc/hexanes) which affords 600 mg of the boc-amine, a white solid. LC/MS: m/z [M+H]$^+$1196, R$_t$=1.72 min, (method 1).

Step 2:

To a solution of the boc-amine (540 mg, 0.451 mmol) in DCM (250 mL) is added acetic anhydride (0.100 mL, 0.979 mmol), pyridine (1.0 mL, 12.4 mmol) and DMAP (20 mg, 0.169 mmol). The reaction is stirred for 3 h, concentrated directly onto SiO$_2$ and chromatographed (gradient elution: 50-70% EtOAc/hexanes) which provides 465 mg of boc-amine-acetate. LC/MS (method 1): R$_t$=1.81 min, [M+H]$^+$ 1238.

Step 3:

To a solution of the boc-amine-acetate (1 g, 0.836 mmol) in DMF (10 mL) is added cesium carbonate (>10 fold excess). The reaction is stirred for 12 h and concentrated onto SiO$_2$. The crude material is purified by flash column chromatography (gradient elution: 0-10% MeOH in DCM) to afford 700 mg of the alkylated product (with the acetate removed).

Step 4:

To a solution of the alkylated boc-amine (100 mg, 0.076 mmol) in DCM (15 mL) is added HCl (g) via a stream. After 10 min, the reaction appeared complete by LC/MS and the reaction is concentrated 3× from DCM.

Step 5-6:

To a solution of the amine salt in DCM (15 mL) is added excess TBTU (>10 equivalents) 50 uL of pyridine, and 50 uL of the diacid. The reaction is stirred for 12 h and NaOH (100 mg), 10 mL of MeOH, and 1 mL H$_2$O are added. The reaction stirred 24 h and is concentrated and purified by HPLC (gradient elution, 20-40% MeCN in H$_2$O+5% isopropanol). LC/MS: m/z [M+H]$^+$ 1322, R$_t$=1.2 (method 10).

Example 9

Preparation of Diacid 21 of Table A

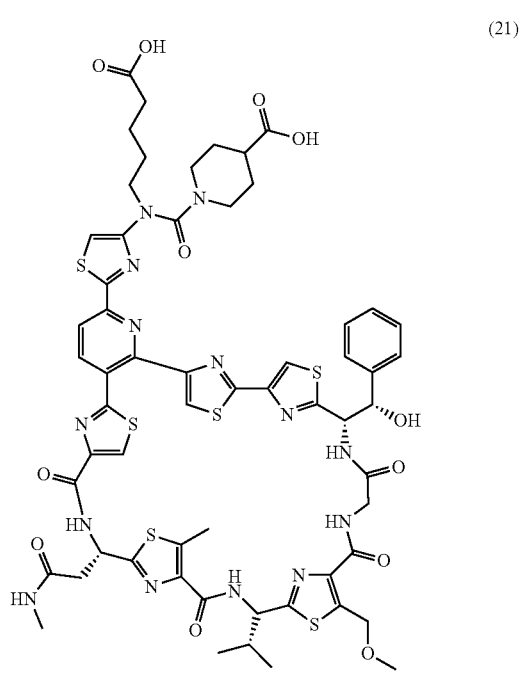

(21)

Scheme 5:

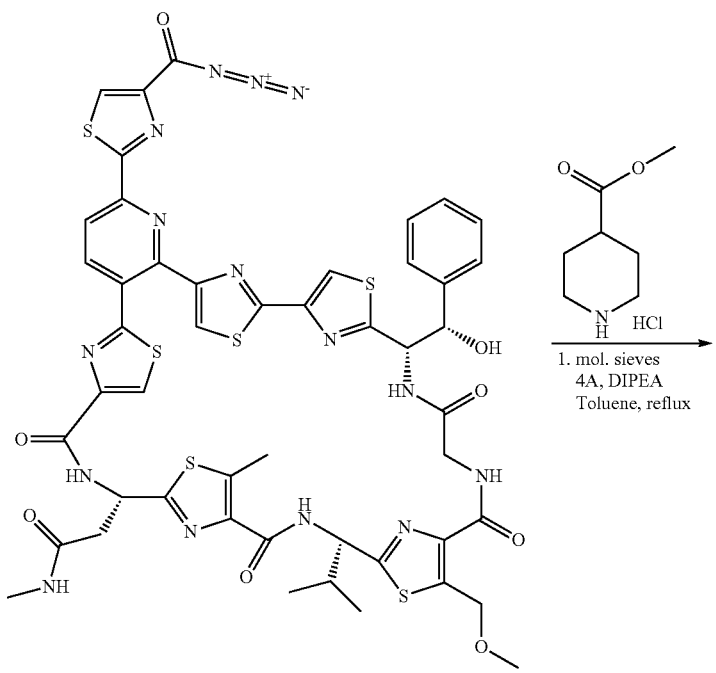

-continued
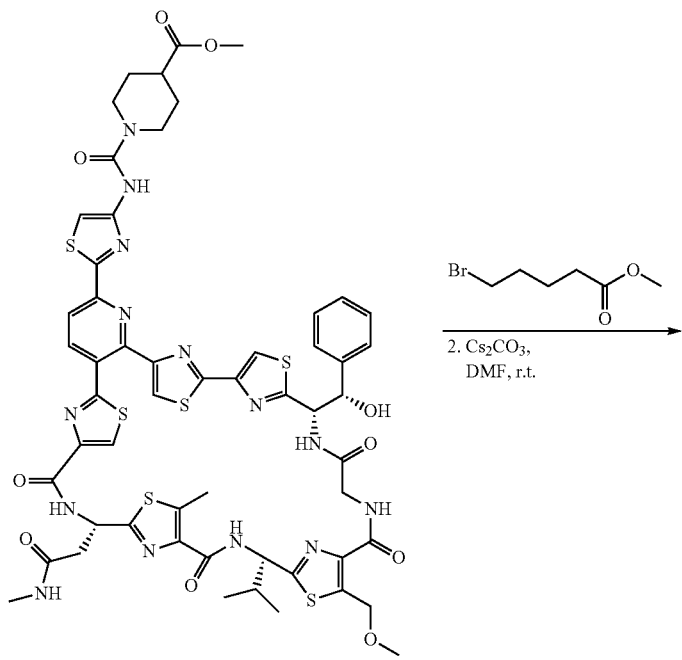
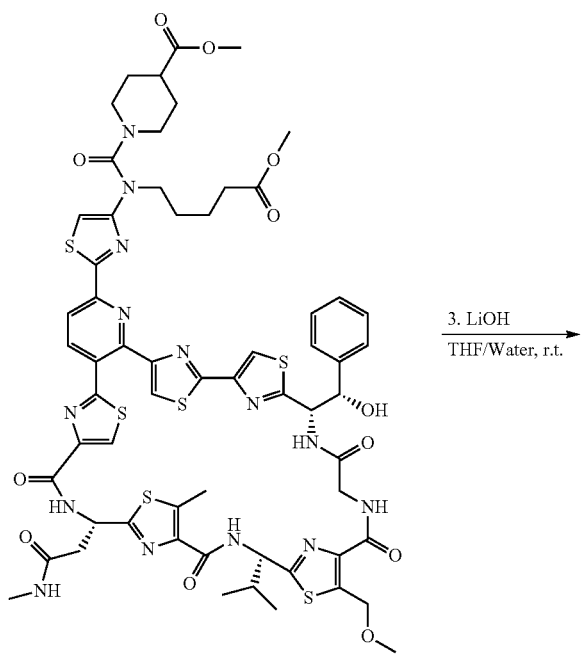

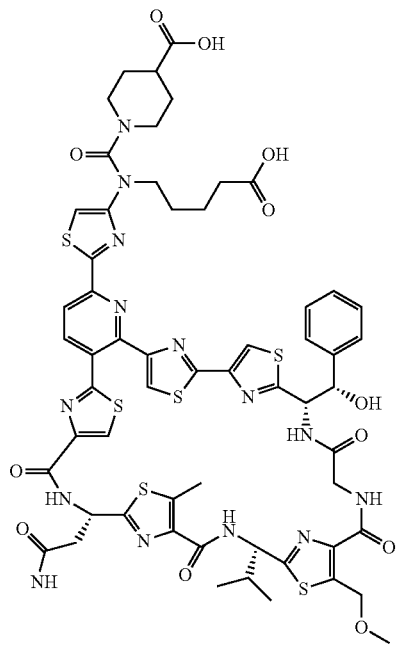

Step 1:

To a solution of azide (100 mg, 0.087 mmol) in toluene (5 mL) is added methyl isonipecotinate hydrochloride (17.2 mg, 0.096 mmol) and molecular sieves at ambient temperature. The mixture is then heated to 70° C. and stirs for 12 h. The reaction is cooled to ambient temperature, concentrated and purified by flash chromatography (gradient elution: 0-10% MeOH/DCM) which affords 90 mg of methyl ester. LC/MS: m/z [M+H]$^+$1265.6, R$_t$=1.49 min (method 10).

Step 2:

To a solution of methyl ester (60 mg, 0.047 mmol) in DMF (2 mL) is added methyl bromovalerate (28 mg, 0.142 mmol) and cesium carbonate (46 mg, 0.142 mmol) at ambient temperature. The mixture stirs at ambient temperature for 4 days. Water is added to quench the reaction, the aqueous phase is extracted with 5% MeOH/DCM three times. Organic phases are combined and dried over sodium sulfate, filtered, concentrated and purified by flash chromatography (gradient elution: 0-10% MeOH/DCM) which affords 20 mg of dimethyl ester. LC/MS: m/z [M+2H]$^{2+}$691, R$_t$=1.58 min (method 10).

Step 3:

To a solution of the dimethyl ester (20 mg, 0.015 mmol) in THF (2 mL)/water (0.4 mL) is added LiOH (0.6 mL, 0.06 mmol, 0.1 M). The reaction is stirred at ambient temperature for 4 h. 0.6 mL 0.1 M HCl is added to quench the reaction, the mixture is concentrated and diluted with MeOH, the residue is purified by HPLC (10-60% acetonitrile in H$_2$O+ 0.1% ammonium hydroxide) furnishing 4.3 mg compound 21. LC/MS: m/z [M+2H]$^{2+}$676, R$_t$=1.35 min (method 10).

Example 10
Preparation of Diacid 11 of Table A (11)

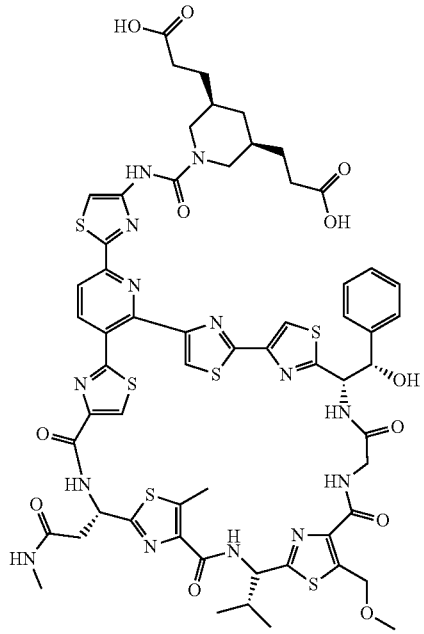

Compound 11 is prepared according to the procedures described in example 9. LC/MS: m/z [M+H]$^+$1353, R$_t$=1.3 min (method 10). $^1$H NMR (400 MHz, DMSO-d$_6$) δ ppm 0.73 (d, J=13.14 Hz, 1H), 0.87 (dd, J=12.38, 6.82 Hz, 6H), 1.28-1.57 (m, 8H), 1.88 (d, J=11.87 Hz, 1H), 2.12-2.23 (m, 1H), 2.24-2.40 (m, 7H), 2.60 (s, 3H), 2.65-2.83 (m, 2H), 3.40 (s, 3H), 3.80 (dd, J=16.80, 3.92 Hz, 1H), 4.17-4.37 (m, 3H), 4.96-5.07 (m, 3H), 5.17-5.35 (m, 3H), 6.11 (brs, 1H), 7.19-7.35 (m, 5H), 7.37 (s, 1H), 7.38-7.47 (m, 1H), 7.59 (s, 1H), 8.20 (d, J=8.08 Hz, 1H), 8.25 (s, 1H), 8.40 (d, J=8.08 Hz, 1H), 8.42-8.49 (m, 1H), 8.60 (s, 1H), 8.69 (d, J=8.34 Hz, 2H), 9.01-9.10 (m, 1H), 9.84 (s, 1H).

Example 11
Preparation of Diacid 12 of Table A

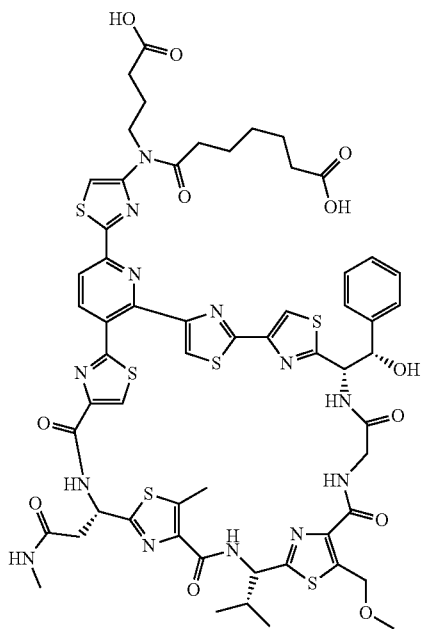

(12)

Compound 12 is prepared according to the procedures described in example 8. LC/MS: m/z [M+2H]$^+$1325, R$_t$=1.3 min (method 10).

Example 12
Preparation of Diacid 13 of Table A

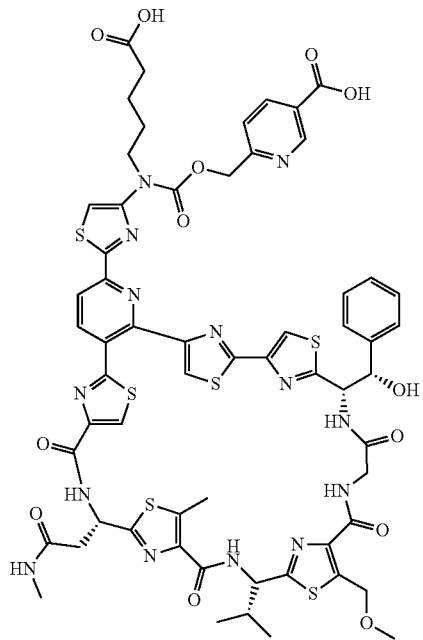

(13)

Compound 13 is prepared according to the procedures described in example 2. LC/MS: m/z [M+H]$^+$1375, R$_t$=0.64 min (method 10).

Example 13
Preparation of Diacid 14 of Table A

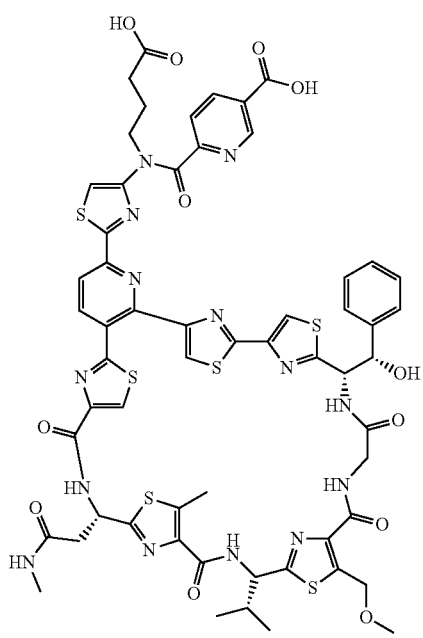

(14)

Compound 14 is prepared according to the procedures described in example 8. LC/MS: m/z [M+2H]$^+$ 1332, R$_t$=1.18 min (method 10).

Example 14
Preparation of Diacid 15 of Table A

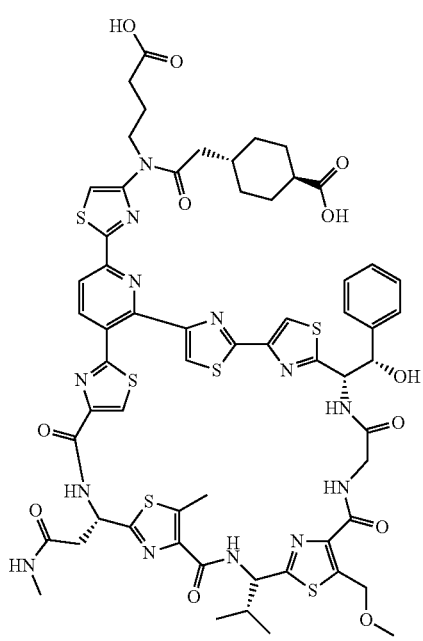

(15)

Compound 15 is prepared according to the procedures described in example 8. LC/MS: [M+2H]$^+$ 1351, R$_t$=1.31 min (method 10).

Example 15
Preparation of Diacid 16 of Table A

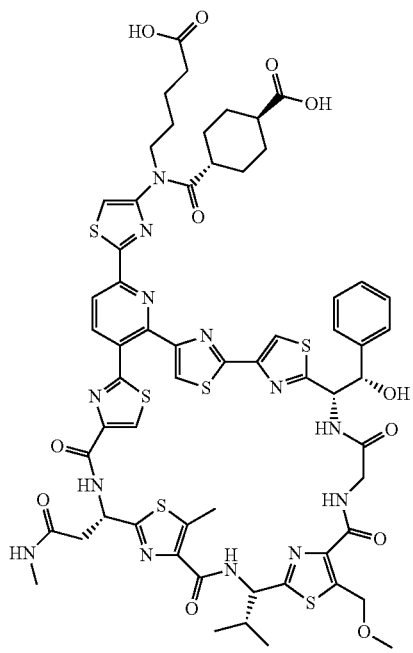

(16)

Compound 16 is prepared according to the procedures described in example 8. LC/MS: m/z [M+2H]$^+$ 1351, R$_t$=1.22 min (method 10).

Example 16
Preparation of Diacid 17 of Table A

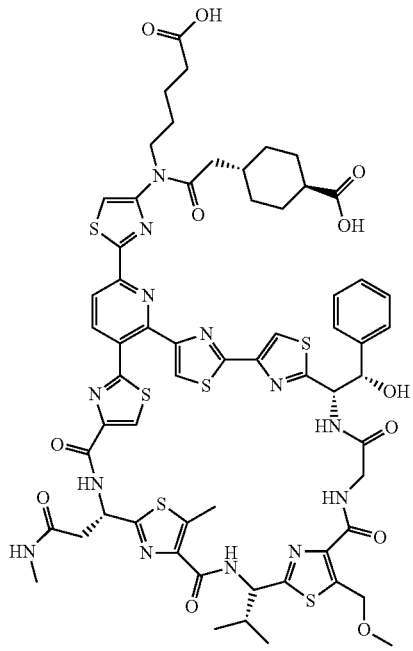

(17)

Compound 17 is prepared according to the procedures described in example 8. LC/MS: m/z [M+2H]$^+$ 1365, R$_t$=1.31 min (method 10).

Example 17
Preparation of Diacid 18 of Table A

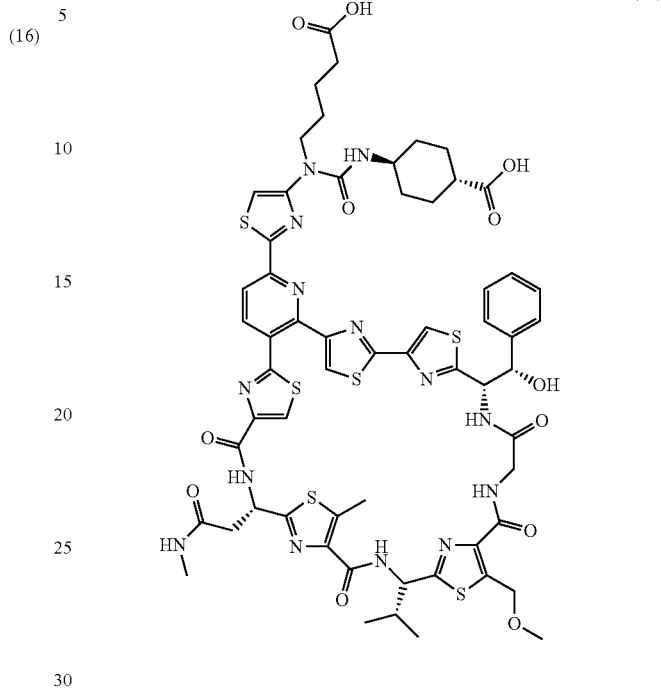

(18)

Compound 18 is prepared according to the procedures described in example 9. LC/MS: m/z [M+2H]$^+$ 1366, R$_t$=1.48 min (method 10).

Example 18
Preparation of Diacid 19 of Table A

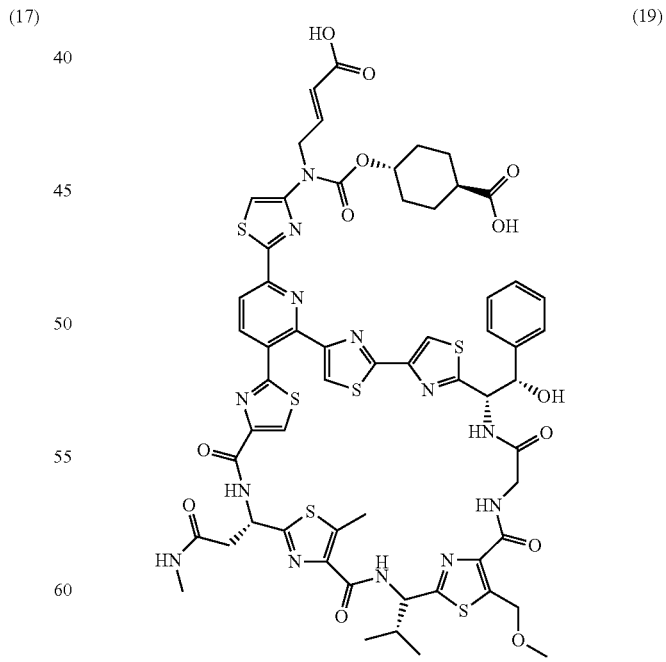

(19)

Compound 19 is prepared according to the procedures described in example 2. LC/MS: m/z [M+H]$^+$ 1350, R$_t$=1.3 min (method 5).

Example 19
Preparation of Diacid 20 of Table A

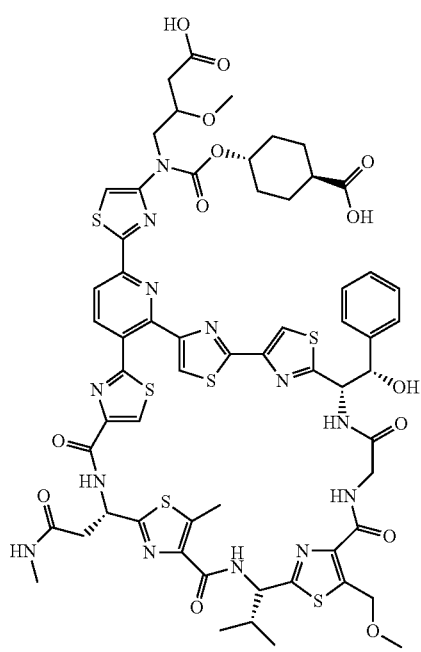
(20)

Compound 20 is prepared according to the procedures described in example 2. LC/MS: m/z [M+H]+ 1382, $R_t$=1.2 min (method 5).

Example 20
Preparation of Diacid 22 of Table A

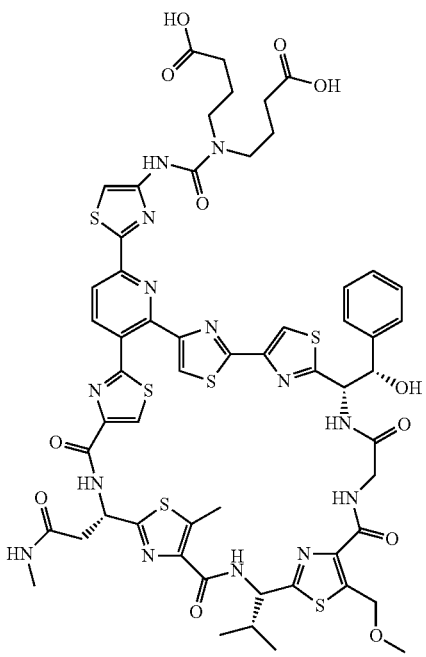
(22)

Compound 22 is prepared according to the procedures described in example 9. LC/MS: m/z [M+2H]$^{2+}$ 656, $R_t$=1.34 min (method 10).

Example 21
Preparation of Diacid 23 of Table A

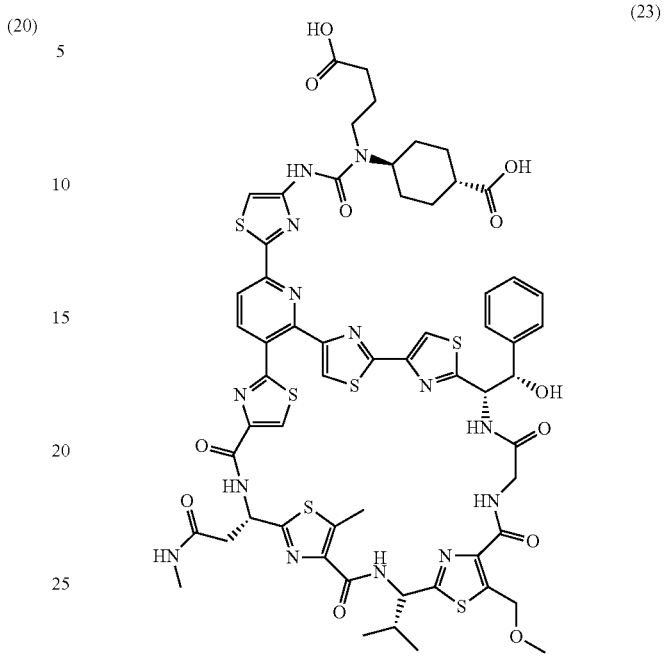
(23)

Compound 23 is prepared according to the procedures described in example 9. LC/MS: m/z [M+2H]+ 1352, $R_t$=1.47 min (method 10).

Example 22
Preparation of Diacid 24 of Table A

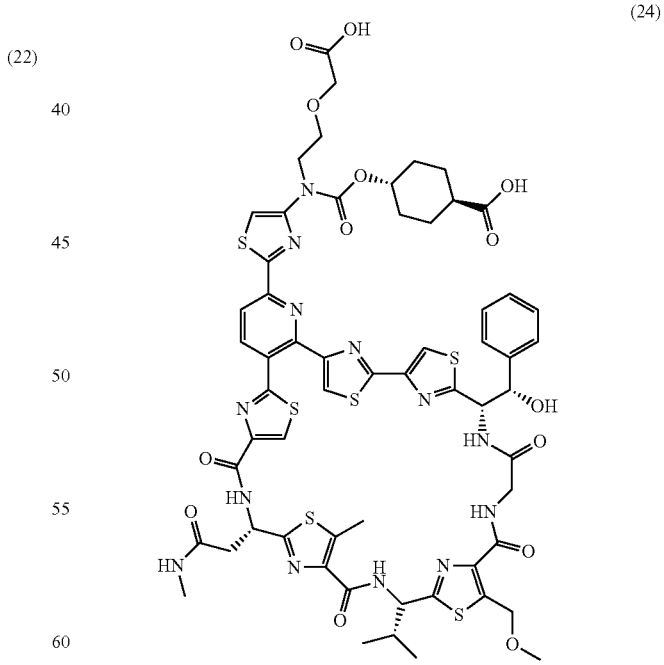
(24)

Compound 24 is prepared according to the procedures described in example 2. LC/MS: m/z [M+2H]+ 1368, $R_t$=1.28 min (method 5). $^1$H NMR (DMSO-d6, 400 MHz) δ ppm 0.78-0.98 (m, 6H), 1.21-1.36 (br, 1H), 1.39-1.55 (br, 4H), 1.85-2.08 (br, 4H), 2.09-2.21 (m, 1H), 2.22-2.30 (br, 1H), 2.47 (s, 3H), 2.60 (s, 3H), 2.68-2.76 (br, 1H), 3.39 (s, 3H), 3.71-3.85 (m, 3H), 4.06 (s, 2H), 4.12-4.20 (br, 2H), 4.22-4.33 (m, 1H), 4.61-4.71 (br, 1H), 4.94-5.03 (m, 3H), 5.17-5.34 (m, 3H), 5.96-6.10 (br, 1H), 7.18-7.43 (m, 7H), 7.72 (s, 1H), 8.19-8.29 (m, 2H), 8.36-8.41 (m, 1H), 8.42-8.48 (m, 1H), 8.60 (s, 1H), 8.69 (t, J=7.8, 7.8 Hz, 2H), 9.04 (d, J=7.70 Hz, 1H), 12.04-12.81 (br, 2H).
Example 23
Preparation of Diacid 25 of Table A
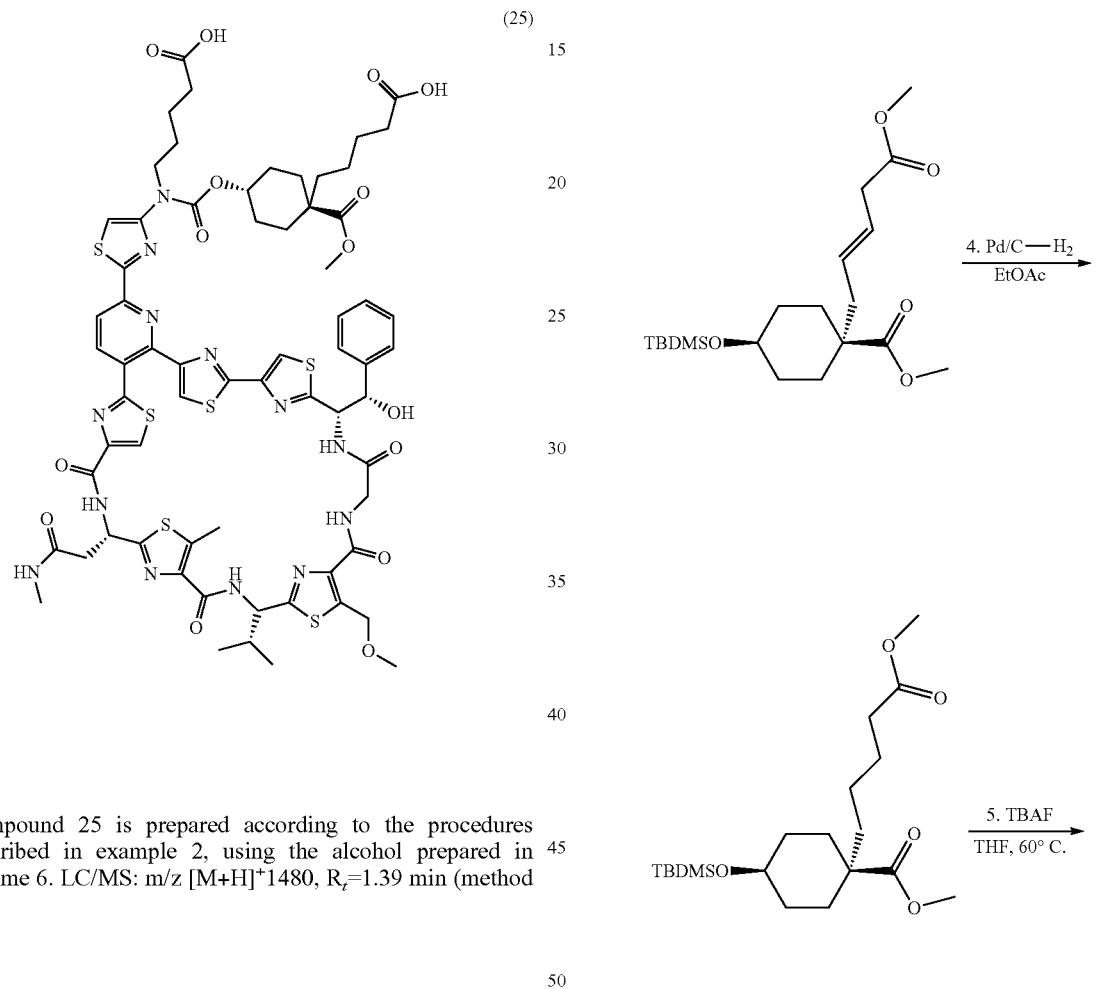
Compound 25 is prepared according to the procedures described in example 2, using the alcohol prepared in scheme 6. LC/MS: m/z [M+H]$^+$1480, R$_t$=1.39 min (method 6).
Scheme 6:
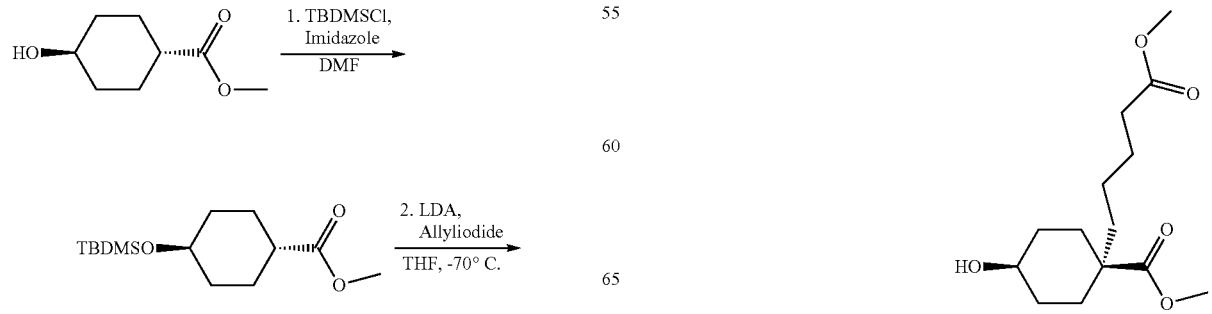

Step 1:

Chloro (1,1-dimethylethyl)dimethylsilane (1.10 g, 7.1 mmol) is added in portions over 5 min. to a solution of the alcohol (1.0 g, 6.30 mmol), imidazole (959 mg, 14.08 mmol) and DMF (4.2 mL) and the mixture is stirred under an atmosphere of $N_2$ for 3 h. The reaction mixture is then poured into 10% citric acid (18 mL) and extracted with ethyl acetate. The organic extracts are washed with water, brine, and then dried ($Na_2SO_4$) and purified by flash chromatography (eluent: ethyl acetate/heptane, gradient) to afford the TBS ether (quant.). $^1$H NMR (400 MHz, $CDCl_3$) δ 3.61 (s, 3H), 2.20 (m, 1H), 1.85 (m, 4H), 1.50-1.20 (m, 4H), 0.83 (s, 9H), 0.00 (s, 6H).

Step 2:

To a solution of LDA (367 uL, 0.734 mmol, 2 M in heptane/THF/ethyl benzene) in THF (1 mL) cooled to −70° C., the TBS ether (100 mg, 0.367 mmol) is added in THF (1 mL). After 1 h at −70° C., allyl iodide (101 uL, 1.10 mmol) is added and the solution is allowed to warm to room temperature and stirred for 2 h. It is then partitioned between ammonium chloride and ethyl acetate. The organic layer is dried ($Na_2SO_4$) and purified by flash chromatography (eluent: ethyl acetate/heptane, gradient) to afford the olefin (100 mg, 87%). $^1$H NMR (400 MHz, $CDCl_3$) δ 5.70 (m, 1H), 4.98 (m, 2H), 3.63 (s, 3H), 3.45 (m, 1H), 2.17 (m, 2H), 1.58-1.10 (m, 7H), 0.84 (s, 9H), 0.00 (s, 6H).

Step 3:

To a solution of Grubbs II (11 mg, 0.013 mmol) in DCM (1.5 mL) are added simultaneously via syringe methyl-3-butenoate (139 uL, 1.29 mmol) and the olefin (81 mg, 0.26 mmol). The reaction mixture is heated to 40° C. and is stirred for 12 h. The solvent is concentrated and purified by flash chromatography (eluent: ethyl acetate/heptane, gradient) to afford the diester (75 mg, 75%). $^1$H NMR (400 MHz, $CDCl_3$) δ 5.50-5.35 (m, 2H), 3.64 (s, 6H), 3.50 (m, 1H), 3.00 (d, 2H), 2.15 (br, 4H), 1.80-1.10 (m, 6H), 0.85 (s, 9H), 0.00 (s, 6H).

Step 4:

To a solution of the diester (200 mg, 0.52 mmol) in ethyl acetate (2.5 mL) is added Pd/C (80 mg) under $N_2$ atmosphere. The reaction mixture is charged with $H_2$ (balloon) and stirred for 2 h after which the reaction mixture is filtered through celite and concentrated to afford saturated diester (172 mg, 86%). $^1$H NMR (400 MHz, $CDCl_3$) δ 3.63 (d, 6H), 3.50 (m, 1H), 3.50 (m, 1H), 2.24 (t, 2H), 2.15 (d, 2H), 1.70-1.10 (m, 8H), 0.85 (s, 9H), 0.00 (s, 6H).

Step 5:

To a solution of saturated diester (172 mg, 0.45 mmol) in THF (2 mL) is added TBAF (890 mL, 0.89 mmol, 1 M solution in THF) and heated to 60° C. for 5 h. The reaction mixture is then concentrated and purified by flash chromatography (eluent: ethyl acetate/heptane, gradient) to afford the alcohol (90 mg). $^1$H NMR (400 MHz, $CDCl_3$) δ 3.62 (s, 3H), 3.60 (s, 3H), 3.50 (m, 1H), 2.18 (m, 4H), 1.8 (br, 2H), 1.80-1.10 (m, 10H).

Example 24

Preparation of Triacid 26 of Table A

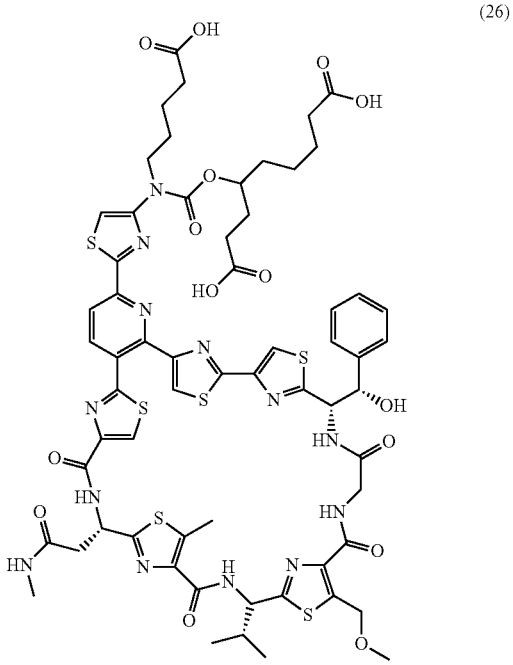

(26)

Compound 26 is prepared according to the procedures described in example 2, using the alcohol prepared in scheme 7. LC/MS: m/z $[M+H_2O]^+$ 1443, $R_t$=1.14 min (method 6).

Scheme 7:

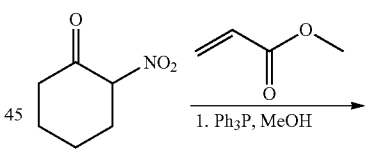

1. $Ph_3P$, MeOH

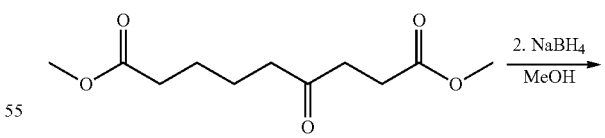

2. $NaBH_4$
MeOH

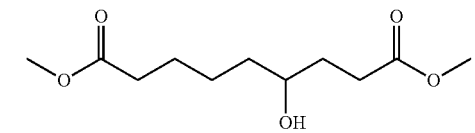

121

Step 1:

To a solution of 2-nitrocyclohexanone (2.0 g, 18.97 mmol) in MeOH (28 mL) is added methyl acrylate (1.4 mL, 15.37 mmol) and a catalytic amount of $Ph_3P$ (10%). After stirring at room temperature for 12 h, an alcoholic solution (209 mL) of KOH (20.9 mmol) is added and the solution is heated at reflux for 8 h. After cooling to 0° C., an aqueous solution (209 mL) of $KMnO_4$ (16.70 mmol) and $MgSO_4$ (20.95 mmol) is slowly added, and after the complete addition, the reaction mixture is stirred for 18 h at room temperature, and then filtered through celite. After extraction with ethyl acetate, the organic phase is dried, evaporated and the crude product is purified by flash chromatography (eluent: ethyl acetate/heptane, gradient) to afford 1.37 g of the ketone: $^1$H NMR (400 MHz, $CDCl_3$) δ 3.69 (s, 3H), 3.67 (s, 3H), 2.72 (m, 2H), 2.59 (m, 2H), 2.48 (br, 2H), 2.33 (br, 2H), 1.63 (m, 4H).

Step 2:

To a solution of the ketone dimethylester (500 mg, 2.17 mmol) in MeOH (11 mL) is added $NaBH_4$ (41 mg, 1.08 mmol) at 0° C. The reaction temperature is warmed to room temperature and stirred for 30 min. TLC (EtOAc/heptane, 6:4) showed complete conversion. The reaction mixture is concentrated and purified by flash chromatography (eluent: EtOAc/heptane, gradient) to afford the alcohol (444 mg, 88%). $^1$H NMR (400 MHz, $CDCl_3$) δ 4.42 (m, 1H), 3.60 (s, 6H), 1.81 (m, 4H), 1.75-1.43 (m, 8H).

Example 25

Preparation of Diacid 27 of Table A

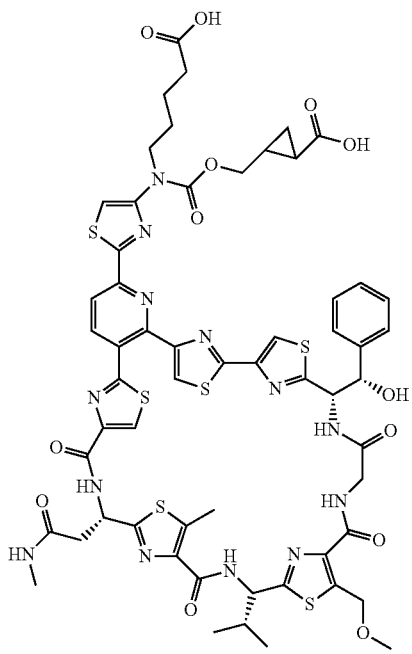

(27)

Compound 27 is prepared according to the procedures described in example 2. LC/MS: m/z [M+2H]$^+$ 1339, $R_t$=1.28 min (method 5).

122

Example 26

Preparation of Triacid 28 of Table A

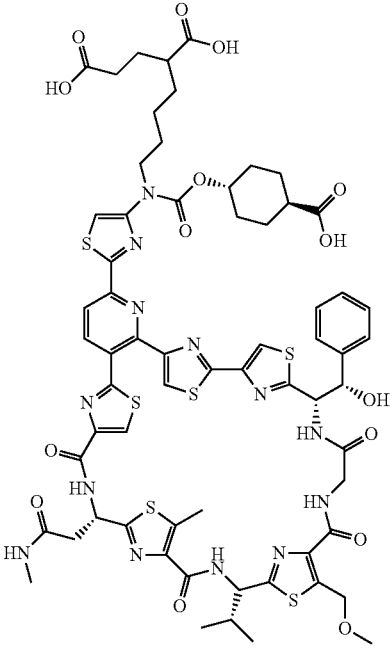

(28)

Scheme 8

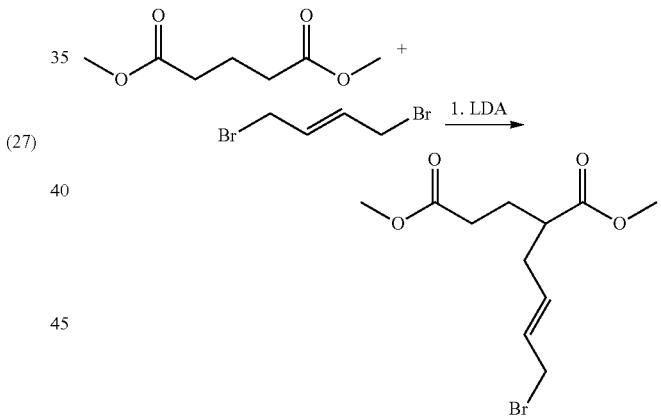

Step 1:

To a solution of diisopropylamine (3.46 mL, 24.54 mmol) in THF (110 mL), is added n-BuLi (15.22 mL, 24.35 mmol) at 0° C. under nitrogen. The resulting mixture is stirred for 15 mins at 0° C. To this solution at −78° C. is added dropwise a solution of dimethyl glutarate in THF (9 mL), and the resulting mixture is stirred for 5 min. A solution of 1,4-dibromobutene in THF (9 mL) and HMPA (9 mL) is then added at −78° C., and the stirring is continued for 2 h at −78° C. The reaction is quenched with 30 mL saturated aq $NH_4Cl$ aqueous solution. The THF is removed, and the material extracted with DCM (3×50 mL). The combined organic layers are concentrated, and the residue is purified by flash chromatography, eluting with hepatane/EtOAc to afford 600 mg of the bromide. LC/MS: m/z [M+H]$^+$293, $R_t$=1.12 min (method 5).

Scheme 9:
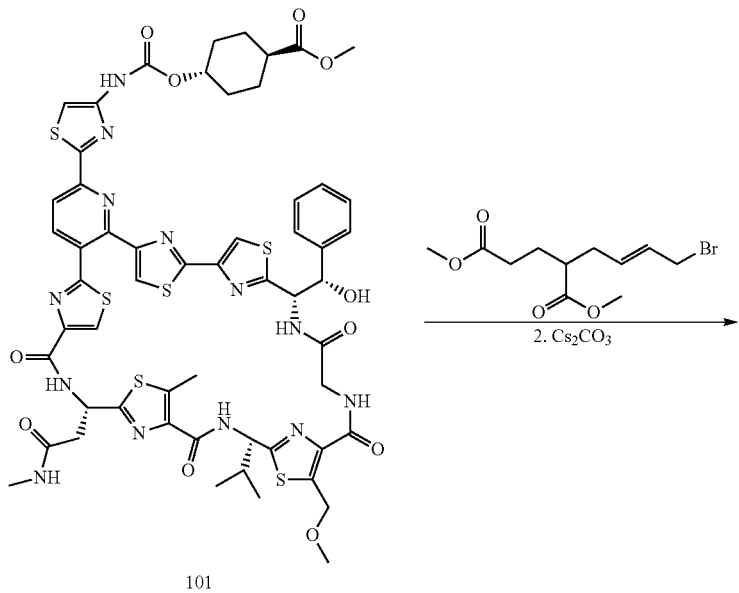
101
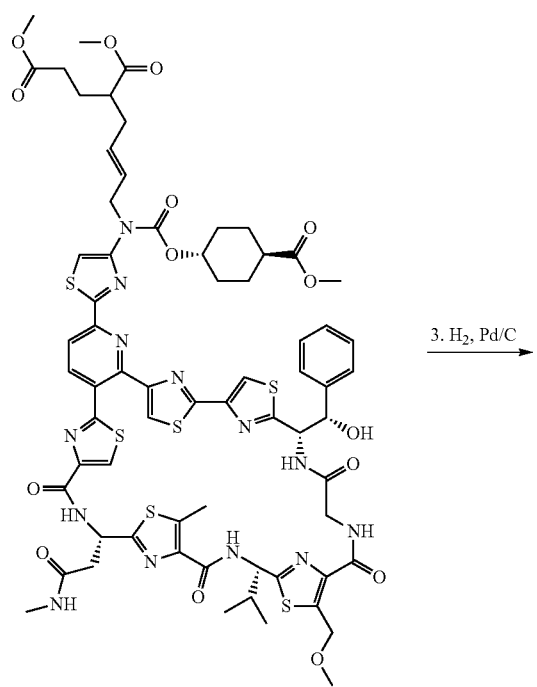
102

-continued

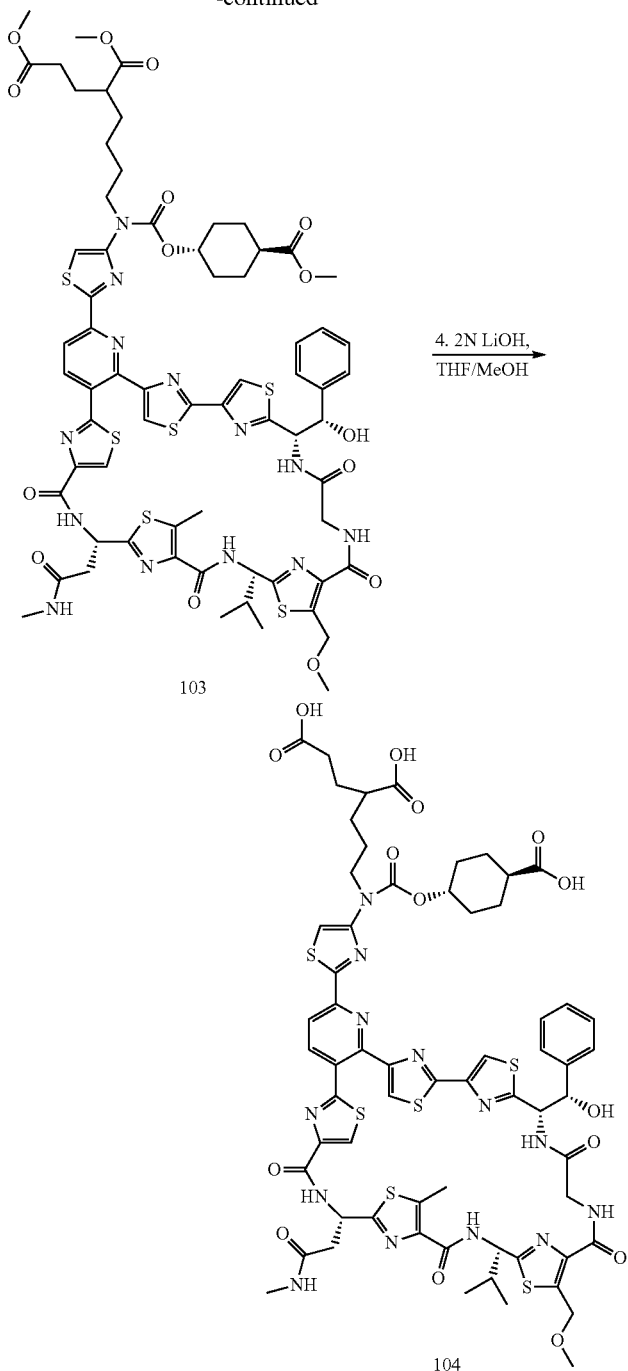

4. 2N LiOH,
THF/MeOH →

Step 2:

To a solution of 101 (416 mg, 0.325 mmol) and $Cs_2CO_3$ (371 mg, 1.137 mmol) in DMF (4.2 mL), is added the bromide (616 mg, 2.094 mmol). The reaction is stirred at rt for 12 h, filtered ($Cs_2CO_3$), and concentrated. The residue is purified by flash chromatography, eluting with DCM/MeOH (gradient: 0-10%) to provide 290 mg (60%) of 102 as a yellow solid. LC/MS: m/z [M+H]$^+$1492, $R_t$=1.73 min (method 5).

Step 3:

To a solution of 102 (290 mg, 0.194 mmol) in DCM (5 mL) and MeOH (16 mL), is added 10% Pd/C (82 mg, 0.078 mmol), degassed and hydrogenated at 50 psi for 12 h. The reaction is filtered, and additional 10% Pd/C (82 mg, 0.078 mmol) and ammonium formate (240 mg, 3.82 mmol) are added. The reaction stirred at reflux for two days and is filtered and purified by flash chromatography, then purified by HPLC (gradient elution, MeCN/H$_2$O, 0.1% TFA) to afford 50 mg of 103. LC/MS: m/z [M+H]$^+$1494, $R_t$=1.75 min (method 5).

Step 4:

To a solution of 103 (50 mg, 0.033 mmol) in THF (0.5 mL) and H$_2$O (0.3 mL) is added 2 N LiOH (0.188 mL, 0.377 mmol) and the reaction mixture is stirred at rt for 25 h. The reaction is neutralized with NH₄Cl until pH=6-7. The reaction mixture is concentrated under vacuum. The residue is dissolved in DMF/H₂O, purified with HPLC (0.1% TFA modified), and lyophilized for 12 h to provide 15 mg (30%) of 104, a light yellow solid. LC/MS: m/z [M+2H]⁺1453, R$_t$=1.29 min (method 5).

Example 27

Preparation of Triacid 29 of Table A

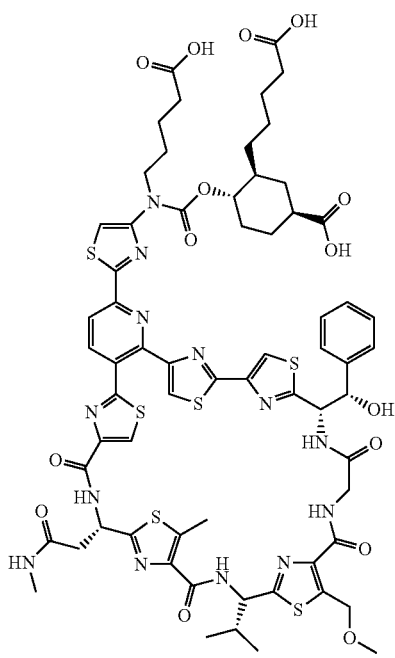

(29)

Compound 29 is prepared according to the procedures described in example 2, using the alcohol prepared in scheme 10. LC/MS: m/z [M+H]⁺1466, R$_t$=1.18 min (method 6).

Step 1:

To a solution of oxalyl chloride (2.92 mL, 33.4 mmol) in DCM (139 mL) at −78° C. is added DMSO (4.74 mL, 66.8 mmol) and the mixture is stirred for 30 minutes. A solution of alcohol (4.4 g, 27.8 mmol) in DCM (5 mL) is then added and the mixture is stirred for an additional 45 minutes. Finally, Et₃N (18.61 mL, 134 mmol) is added and the white solution is allowed to stir at −78° C. for 30 minutes before being warmed to 0° C. over 30 minutes. Saturated aqueous NH₄Cl is added to quench the reaction and the resulting mixture is extracted with DCM (3×100 mL). The combined organic extracts are dried (MgSO₄), filtered, and concentrated and the residue is purified by flash chromatography (gradient elution: 0-50% EtOAc/heptane) furnishing 4.1 g of the ketone. ¹H NMR (400 MHz; CDCl₃) δ 3.85 (s, 3H), 2.90 (m, 1H), 2.64-2.57 (m, 2H), 2.52-2.44 (m, 2H), 2.37-2.32 (m, 2H), 2.20-2.10 (m, 2H).

Step 2:

To a solution of ketone (3.8 g, 24.3 mmol) in THF (57.9 mL) at −78° C. is added HMPA (23.2 mL), followed by KHMDS (51.1 mL, 25.5 mmol, 0.5 M solution in toluene) and the resulting yellow solution is stirred for 30 minutes. Allyl iodide (2.45 mL, 26.8 mmol) is added dropwise and the reaction mixture is allowed to stir at −78° C. for 30 minutes before being warmed to room temperature over 10 minutes. Saturated aqueous NaHCO₃ is added to quench the reaction and the resulting mixture is extracted with EtOAc (3×100 mL). The combined organic extracts are washed with brine, dried (MgSO₄), filtered and concentrated and the residue is purified by flash chromatography (gradient elution: 0-50% EtOAc/heptane) furnishing 3.3 g of the olefin, ¹H NMR (400 MHz; CDCl₃) δ 5.81-5.70 (m, 1H), 5.11-5.02 (m, 2H), 3.76 (s, 3H), 2.84 (t, 4.8 Hz, 1H), 2.61-2.30 (m, 6H), 2.07-1.93 (m, 2H), 1.73-1.66 (ddd, 13.8, 10.4, 4.7 Hz, 1H), followed by 985 mg of the isomer: ¹H NMR (400 MHz; CDCl₃) δ 5.81-5.73 (m, 1H), 5.07-5.02 (m, 2H), 3.71 (s, 3H), 2.82 (t, 4.8 Hz, 1H), 2.61-2.30 (m, 6H), 2.09-1.81 (m, 2H), 1.61-1.50 (m, 1H).

Scheme 10:

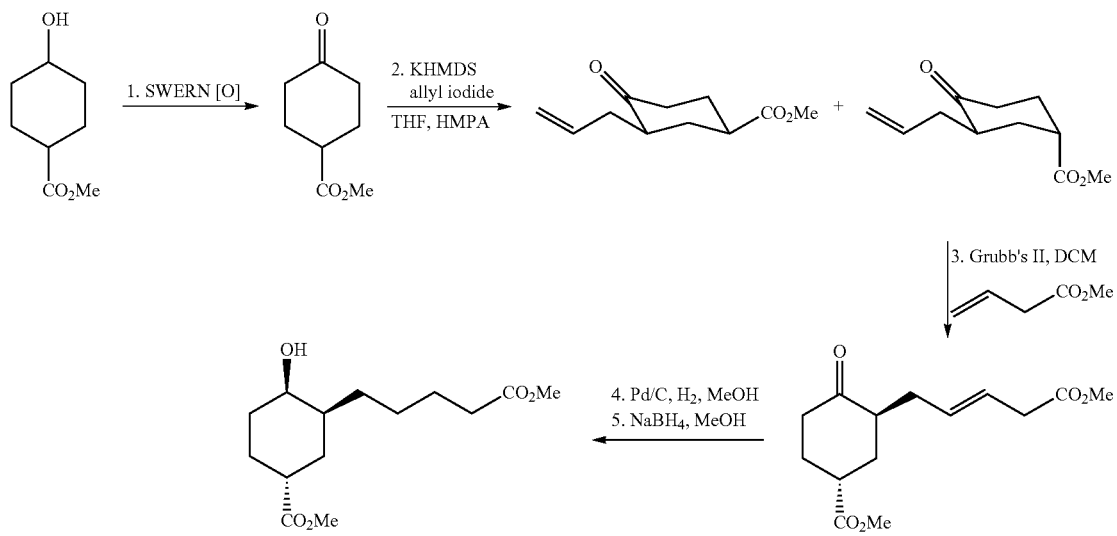

Step 3:

To a solution of the olefin (310 mg, 1.58 mmol) and methyl-3-butenoate (843 μL, 7.90 mmol) in DCM (10 mL) at reflux is added a solution of Grubb's II (67 mg, 5 mol %) and the resulting red mixture is stirred for 3 hours. The solvent is evaporated and the residue is purified by flash chromatography (gradient elution: 0-50% EtOAc/heptane) furnishing 315 mg of the diester. $^1$H NMR (400 MHz; CDCl$_3$) δ 5.66-5.47 (m, 2H), 3.75 (s, 3H), 3.68 (s, 3H), 3.04 (d, 5.8 Hz, 2H), 2.86 (qd, 4.6 Hz, 1H), 2.60-2.30 (m, 6H), 2.13-1.88 (m, 2H), 1.74-1.60 (m, 1H).

Step 4:

A solution of the diester (260 mg, 0.97 mmol) in EtOH (10 mL) is purged with N$_2$, and 10% Pd/C (26 mg, 10% w/w) is added. The mixture is again purged with N$_2$, followed by H$_2$ and then maintained under an atmosphere of H$_2$ (balloon) for 1 hour. The reaction mixture is purged with N$_2$, filtered through a pad of celite and the filtrate concentrated to furnish 261 mg of the saturated diester, which is used without further purification.

Step 5:

To a solution of the saturated diester (261 mg, 0.97 mmol) in MeOH (10 mL) at 0° C. is added NaBH$_4$ (18 mg, 0.49 mmol) and the resulting mixture is allowed to stir for 30 minutes. Saturated aqueous NH$_4$Cl is added to quench the reaction and the resulting mixture is extracted with EtOAc (3×100 mL). The combined organic extracts are washed with brine, dried (MgSO$_4$), filtered and concentrated and the residue is purified by flash chromatography (gradient elution: 0-50% EtOAc/heptane) furnishing 200 mg of the alcohol. $^1$H NMR (400 MHz; CDCl$_3$) δ 3.86-3.80 (m, 1H), 3.67 (s, 3H), 3.66 (s, 3H), 2.58 (t, 4.8 Hz, 1H), 2.37-2.28 (m, 2H), 1.96-1.83 (m, 1H), 1.76-1.22 (m, 13H).

Example 28

Preparation of Triacid 30 of Table A

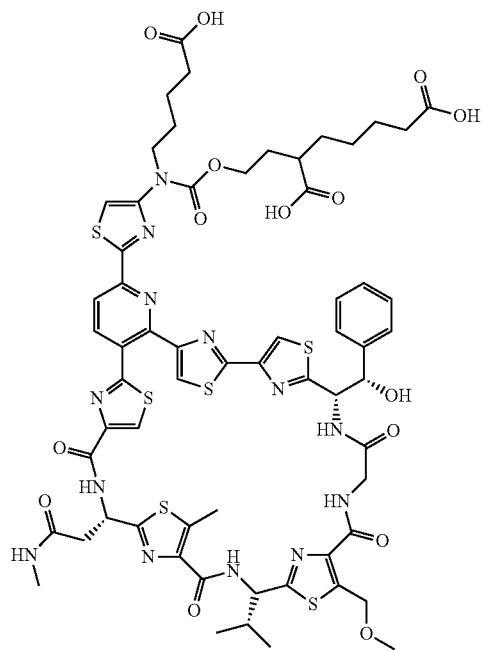

(30)

Compound 30 is prepared according to the procedures described in example 2, using the alcohol prepared in scheme 11. LC/MS: m/z [M+H]$^{2+}$714, R$_t$=1.18 min (method 6). $^1$H NMR (400 MHz, DMSO-d6) δ 9.05 (d, J=7.8 Hz, 1H), 8.69 (t, J=7.8 Hz, 2H), 8.61 (s, 1H), 8.50-8.44 (m, 1H), 8.39 (d, 8.0 Hz, 1H), 8.27 (s, 1H), 8.22 (d, J=8.0 Hz, 1H), 7.73 (s, 1H), 7.43-7.24 (m, 7H), 5.35-5.20 (m, 3H), 4.98 (br s, 3H), 4.33-3.75 (br m, 8H), 3.39 (s, 3H), 2.79-2.66 (m, 1H), 2.59 (s, 3H), 2.28 (t, J=7.0 Hz, 3H), 2.19 (t, J=7.0 Hz, 3H), 2.19-2.12 (m, 1H), 1.94-1.85 (m, 1H), 1.83-1.73 (m, 1H), 1.73-1.62 (m, 3H), 1.62-1.40 (m, 8H), 1.34-1.11 (m, 4H), 0.89 (d, J=6.6 Hz, 3H), 0.85 (d, J=6.6 Hz, 3H).

Scheme 11:

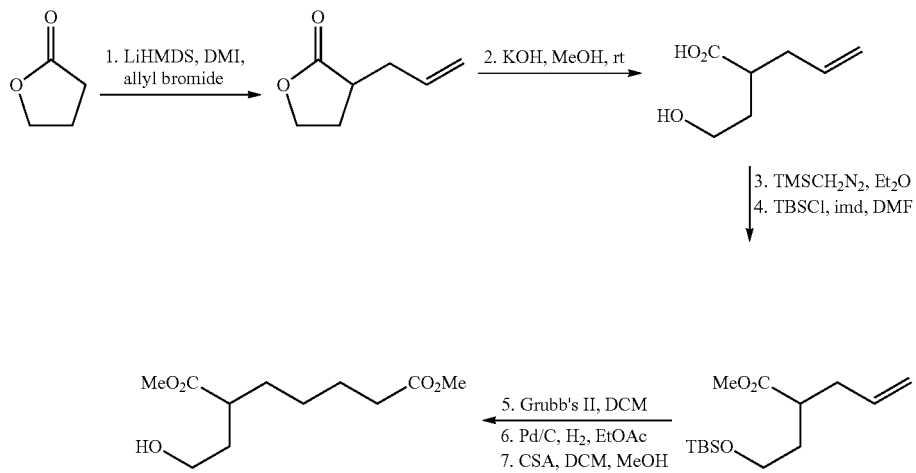

Step 1:
To a solution of γ-butyrolactone (10 g, 116 mmol) in THF (200 mL) at −78° C. is added LiHMDS (122 mL, 122 mmol, 1.0 M solution in THF). After stirring for 30 minutes 1,3-dimethyl-2-imidazolidinone (15.1 mL, 139 mmol), followed by allyl bromide (11.1 mL, 128 mmol) are added and the resulting mixture is allowed to stir for 1 hour. Saturated aqueous NH$_4$Cl is added to quench the reaction and the resulting mixture is extracted with EtOAc (3×100 mL). The combined organic extracts are washed with brine, dried (MgSO$_4$), filtered and concentrated and the residue is purified by flash chromatography (gradient elution: 0-50% EtOAc/heptane) furnishing 14.6 g of the olefin.

Step 2:
To a solution of the olefin (14.6 g, 116 mmol) in MeOH (100 mL) at room temperature is added KOH (13.0 g, 232 mmol) and the resulting mixture is stirred for 3 hours. The solvent is removed from the reaction and the residue is partitioned between H$_2$O and Et$_2$O. The layers are separated and the aqueous phase is extracted with Et$_2$O (2×50 mL). The aqueous phase is then acidified to pH 3 with HCl (1 M) and extracted with EtOAc (3×100 mL). The combined organic extracts are washed with brine, dried (MgSO$_4$), filtered and concentrated furnishing 16.6 g of the acid which is used without further purification.

Step 3:
To a solution of the acid (16.6 g, 116 mmol) in MeOH (200 mL) and Et$_2$O (500 mL) at 0° C. is added (trimethylsilyl)diazomethane (76 mL, 151 mmol, 2.0 M solution in Et$_2$O, enough to maintain a yellow color in the reaction mixture). The solvent is removed from the reaction mixture and the residue is purified by flash chromatography (gradient elution: 0-60% EtOAc/heptane) furnishing 18.3 g of the ester.

Step 4:
To a solution of the ester (18.3 g, 116 mmol) in DMF (150 mL) at room temperature is added imidazole (9.49 g, 139 mmol), followed by TBSCl (19.3 g, 128 mmol) and the resulting mixture is stirred for 8 hours. The reaction mixture is diluted with H$_2$O, extracted with Et$_2$O (3×100 mL) and the combined extracts are washed with H$_2$O (2×100 mL), saturated aqueous NaHCO$_3$ and brine, then dried (MgSO$_4$), filtered and concentrated. The residue is purified by flash chromatography (gradient elution: 0-30% EtOAc/heptane) furnishing 30.6 g of the TBS ether. $^1$H NMR (400 MHz; CDCl$_3$) δ 5.82-5.63 (m, 1H), 5.14-4.94 (m, 2H), 3.67 (s, 3H), 3.67-3.58 (m, 2H), 2.73-2.57 (m, 1H), 2.38-2.18 (m, 2H), 1.96-1.79 (m, 1H), 1.79-1.58 (m, 1H), 0.89 (s, 9H), −0.04 (s, 6H).

Step 5:
The olefin is prepared in an identical manner to that described previously for example 27 and purified by flash chromatography (gradient elution: 0-30% EtOAc/heptane) furnishing 420 mg. $^1$H NMR (400 MHz; CDCl$_3$) δ 5.65-5.43 (m, 2H), 3.68 (s, 3H), 3.66 (s, 3H), 3.66-3.54 (m, 2H), 3.04 (d, 6.6 Hz, 2H), 2.68-2.57 (m, 1H), 2.41-2.21 (m, 2H), 1.94-1.81 (m, 1H), 1.74-1.51 (m, 1H), 0.89 (s, 9H), −0.03 (s, 6H).

Step 6:
The saturated diester is prepared in an identical manner to that described previously for example 27 and purified by flash chromatography (gradient elution: 0-30% EtOAc/heptane) furnishing 340 mg. $^1$H NMR (400 MHz; CDCl$_3$) δ 3.67 (s, 6H), 3.65-3.54 (m, 2H), 2.59-2.48 (m, 1H), 2.30 (t, 7.5 Hz, 2H), 1.92-1.80 (m, 1H), 1.71-1.43 (m, 3H), 1.39-1.19 (m, 4H), 0.89 (s, 9H), −0.04 (s, 6H).

Step 7:
To a solution of the saturated diester (289 mg, 0.83 mmol) in DCM (8 mL) and MeOH (8 mL) at −10° C. is added CSA (213 mg, 0.92 mmol) and the resulting mixture is stirred for 1 hour. Saturated aqueous NaHCO$_3$ is added to quench the reaction and the resulting mixture is extracted with DCM (3×20 mL). The combined organic extracts are washed with saturated aqueous NaHCO$_3$, brine, dried (MgSO$_4$), filtered and concentrated and the residue is purified by flash chromatography (gradient elution: 0-80% EtOAc/heptane) furnishing 190 mg of the alcohol. $^1$H NMR (400 MHz; CDCl$_3$) δ 3.69 (s, 3H), 3.69-3.63 (m, 2H), 3.66 (s, 3H), 2.61-2.48 (m, 1H), 2.30 (t, 7.5 Hz, 2H), 1.95-1.80 (m, 1H), 1.80-1.56 (m, 4H), 1.56-1.39 (m, 1H), 1.39-1.17 (m, 2H).

Example 29

Preparation of Triacid 31 of Table A

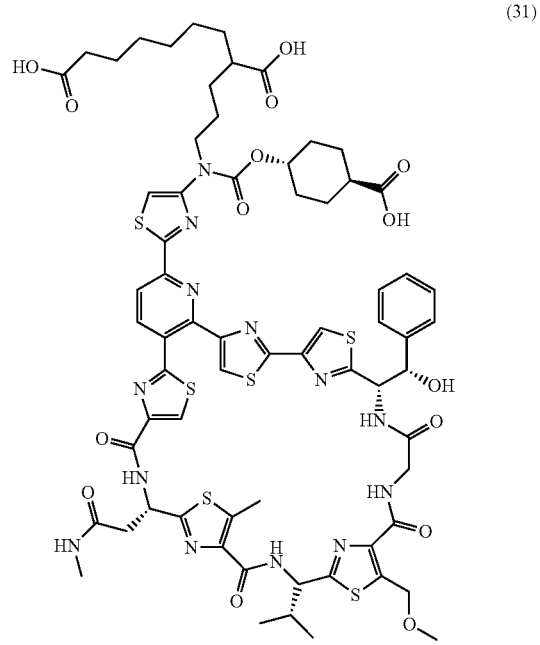

(31)

Compound 31 is prepared according to the procedures described in example 2, using the alcohol prepared in scheme 12. LC/MS: m/z [M+2H]$^+$1495, R$_t$=1.44 (method 5).

Scheme 12:

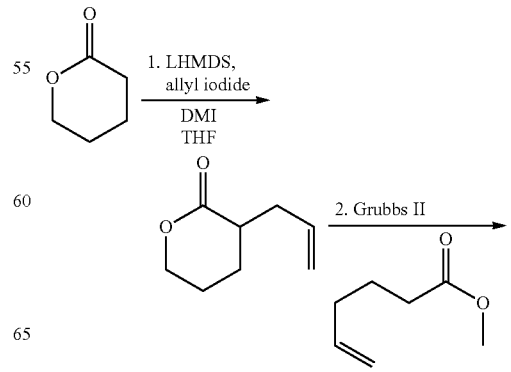

-continued

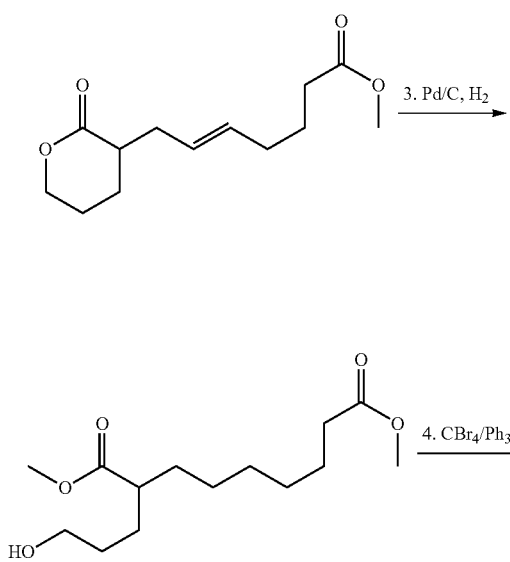

Step 3:

The lactone (1.227 g, 5.11 mmol) and 10% Pd/C (0.893 g, 0.842 mmol) are mixed in MeOH (60 mL). The reaction is degassed and hydrogenated for 2 h. TLC showed disappearance of starting material. The reaction is filtered and concentrated to afford 1.2 g of crude diester-alcohol.

Step 4:

The diester-alcohol (300 mg, 1.093 mmol) and $Ph_3P$ (315 mg, 1.203 mmol) are dissolved in $CH_2Cl_2$ (13 mL), and cooled in an ice bath. $CBr_4$ (363 mg, 1.083 mmol) is added with stirring. The mixture is allowed to warm to rt and is stirred for 12 h. The reaction mixture is concentrated and purified with flash chromatography, eluting by heptane/EtOAc to afford 220 mg (60% yield) of the bromide. $^1$H NMR ($CDCl_3$, 400 MHz) δ 1.30 (broad, 6H) 1.45 (broad, 1H) 1.63 (broad, 5H) 1.85 (m, 2H) 2.30 (t, 2H) 2.35 (m, 1H) 3.40 (t, 2H) 3.67 (s, 6H).

Example 30

Preparation of Triacid 32 of Table A

Step 1:

To a solution of valerolactone (containing 25% polymer, 5 g, 37.5 mmol) in THF (100 mL) at −78° C., is added LHMDS (52.4 mL) over 20 min. The solution is stirred for 0.5 h, then 1,3-dimethyl-2-imidazolidinone (6.84 g, 59.9 mmol) and allyl idodide (5.02 mL, 54.9 mmol) is added, and the reaction is stirred for 1 h. The reaction is quenched with saturated $NH_4Cl$ aqueous solution (50 mL). The mixture is extracted by EtOAc (250 mL), washed with saturated $NaHCO_3$ and brine. The EtOAc layer is concentrated and the residue is purified by flash chromatography, eluting with heptane/EtOAc to afford 3.4 g (64.8% yield) of the olefin.

Step 2:

To a solution of the olefin (1.1 g, 7.854 mmol) and 5-hexenoic acid methylester (5.03 g, 39.226 mmol) in DCM (110 mL) at reflux is added a solution of Grubbs II (332 mg, 0.392 mmol) in DCM (11 mL) and the resulting mixture is stirred for 1 hour at reflux. The residue is purified with flash chromatography, eluting with hepatane/EtOAc to afford 1.227 g (65% yield) of the lactone.

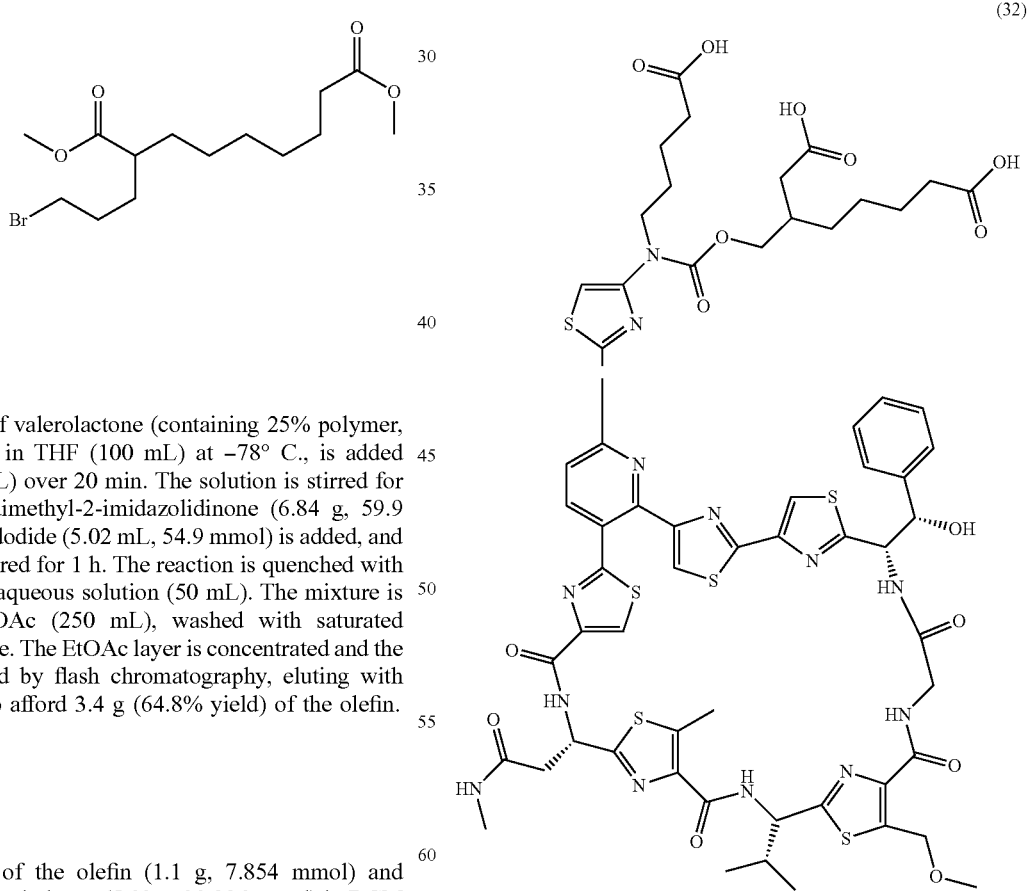

(32)

Compound 32 is prepared according to the procedures described in example 2, using the alcohol prepared in scheme 13. LC/MS: m/z [M+H]$^+$1426, $R_t$=1.05 min (method 6).

Scheme 13:

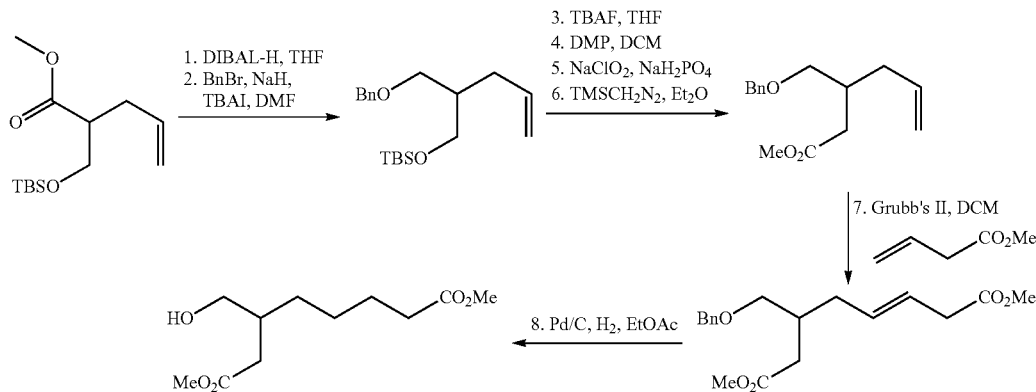

Step 1:
To a solution of the ester (1.0 g, 3.7 mmol) in THF (20 mL) at −10° C. is added DIBAL-H (8.44 mL, 8.4 mmol, 1.0 M solution in hexanes) dropwise and the resulting mixture is stirred for 1 hour. MeOH (10 mL), Rochelle's Salt (100 mL) and EtOAc (100 mL) are added and the biphase is stirred vigorously for 3 h. The layers are separated and the aqueous phase is extracted with EtOAc (3×100 mL). The combined extracts are washed with brine, dried (MgSO$_4$), filtered and concentrated furnishing 895 mg of the alcohol, which is used without further purification. $^1$H NMR (400 MHz; CDCl$_3$) δ 5.86-5.71 (m, 1H), 5.09-4.98 (m, 2H), 3.78 (ddd, 10.4, 6.2, 4.0 Hz, 1H), 3.71-3.57 (m, 2H), 3.52-3.43 (m, 1H), 3.11-2.82 (br s, 1H), 2.18-1.97 (m, 2H), 1.82-1.63 (m, 2H), 1.59-1.47 (m, 1H), 0.91 (s, 9H), 0.08 (s, 6H).

Step 2:
To a solution of the alcohol (895 mg, 3.7 mmol) in DMF (12 mL) at room temperature is added NaH (220 mg, 5.5 mmol). After stirring for 30 minutes, benzyl bromide (524 μL, 4.4 mmol) and tetrabutylammonium iodide (678 mg, 1.8 mmol) are added and the resulting mixture is allowed to stir 12 h. Saturated aqueous NH$_4$Cl is added to quench the reaction and the resulting mixture is diluted with EtOAc (100 mL). The layers are separated and the organic phase is washed with H$_2$O (3×30 mL), brine, then dried (MgSO$_4$), filtered and concentrated and the residue is purified by flash chromatography (gradient elution: 0-30% EtOAc/heptane) furnishing 1.22 g of the benzyl ether. $^1$H NMR (400 MHz; CDCl$_3$) δ 7.43-7.24 (m, 5H), 5.86-5.70 (m, 1H), 5.11-4.96 (m, 2H), 4.50 (s, 2H), 3.73-3.61 (m, 1H), 3.61-3.45 (m, 1H), 3.45-3.34 (m, 1H), 2.28-2.00 (m, 2H), 1.95-1.83 (m, 1H), 1.77-1.49 (m, 3H), 0.90 (s, 9H), 0.05 (s, 6H).

Step 3:
To a solution of the benzyl ether (1.32 g, 4.0 mmol) in THF (20 mL) at 0° C. is added TBAF (5.92 mL, 5.9 mmol, 1.0 M solution in THF) and the resulting mixture is allowed to warm to room temperature and stirred for 2 hours. Saturated aqueous NH$_4$Cl is added to quench the reaction and the resulting mixture is diluted with EtOAc (50 mL). The layers are separated and the aqueous phase is extracted with EtOAc (3×30 mL). The combined organic extracts are washed with brine, then dried (MgSO$_4$), filtered and concentrated and the residue is purified by flash chromatography (gradient elution: 0-80% EtOAc/heptane) furnishing 865 mg of the alcohol. $^1$H NMR (400 MHz; CDCl$_3$) δ 7.41-7.24 (m, 5H), 5.84-5.68 (m, 1H), 5.09-4.94 (m, 2H), 4.53 (s, 2H), 3.76-3.58 (m, 2H), 3.49 (dd, 9.2, 7.2 Hz, 1H), 3.37 (dd, 9.2, 7.2 Hz, 1H), 2.56 (br s, 1H), 2.21-2.01 (m, 2H), 1.98-1.84 (m, 1H), 1.79-1.65 (m, 1H), 1.65-1.52 (m, 1H).

Step 4:
To a solution of the alcohol (600 mg, 2.7 mmol) in DCM (14 mL) at room temperature is added Dess-Martin periodinane (1.4 g, 3.3 mmol) and the resulting mixture is stirred for 1 hour. The reaction mixture is diluted with Et$_2$O (50 mL) and a solution of Na$_2$S$_2$O$_3$ (5.5 g) in saturated aqueous Na$_2$CO$_3$ (10 mL) is added and the biphase is stirred until clear. The layers are separated and the organic phase is washed with saturated aqueous Na$_2$CO$_3$, brine, then dried (MgSO$_4$), filtered and concentrated and the residue is purified by flash chromatography (gradient elution: 0-30% EtOAc/heptane) furnishing 535 mg of the aldehyde. $^1$H NMR (400 MHz; CDCl$_3$) δ 9.77 (s, 1H), 7.38-7.27 (m, 5H), 5.80-5.69 (m, 1H), 5.10-5.03 (m, 2H), 4.48 (s, 2H), 3.49 (dd, 9.2, 4.7 Hz, 1H), 3.33 (dd, 9.2, 6.7 Hz, 1H), 2.51-2.37 (m, 2H), 2.32-2.16 (m, 1H), 2.12-2.02 (m, 1H), 1.33-1.22 (m, 1H).

Step 5:
To a solution of the aldehyde (535 mg, 2.5 mmol) and 2-methyl-2-butene (2.6 mL, 24.5 mmol) in H$_2$O (6 mL) and tert-butanol (6 mL) at room temperature is added a solution of NaH$_2$PO$_4$ (1.47 g, 12.3 mmol) in H$_2$O (500 μL) followed by a solution of NaClO$_2$ (665 mg, 7.4 mmol) in H$_2$O (500 μL). The resulting mixture is allowed to stir for 15 minutes, then brine (10 mL) is added and the mixture is extracted with CHCl$_3$ (3×15 mL). The combined organic extracts are dried (Na$_2$SO$_4$), filtered and concentrated furnishing 574 mg of the acid which is used without further purification.

Step 6:
The ester is prepared in an identical manner to that described previously for example 28 and purified by flash chromatography (gradient elution: 0-30% EtOAc/heptane) furnishing 470 mg. $^1$H NMR (400 MHz; CDCl$_3$) δ 7.37-7.26 (m, 5H), 5.81-5.70 (m, 1H), 5.09-5.01 (m, 2H), 4.49 (s, 2H), 3.69 (s, 3H), 3.46 (dd, 9.3 5.1 Hz, 1H), 3.38 (dd, 9.3, 6.3 Hz, 1H), 2.45-2.18 (m, 3H), 2.13-2.08 (m, 1H), 1.35-1.24 (m, 1H).

Step 7:
The olefin metathesis product is prepared in an identical manner to that described previously for example 27 and purified by flash chromatography (gradient elution: 0-30% EtOAc/heptane) furnishing 500 mg. $^1$H NMR (400 MHz; CDCl$_3$) δ 7.37-7.26 (m, 5H), 5.62-5.43 (m, 2H), 4.52-4.43

(m, 2H), 3.68 (s, 3H), 3.63 (s, 3H), 3.43 (dd, 9.2, 4.8 Hz, 1H), 3.36 (dd, 9.2, 5.9 Hz, 1H), 2.43-2.06 (m, 7H).

Step 8:

The alcohol is prepared in an identical manner to that described previously in example 27 and purified by flash chromatography (gradient elution: 0-80% EtOAc/heptane) furnishing 200 mg. $^1$H NMR (400 MHz; C$_6$D$_6$) δ 3.37 (dd, 10.6, 4.5 Hz, 1H), 3.35 (s, 3H), 3.33 (s, 3H), 3.25 (dd, 10.6, 6.3 Hz, 1H), 2.29 (dd, 15.7, 7.6 Hz, 1H), 2.12 (dd, 15.7, 5.8 Hz, 1H), 2.05 (t, 7.5 Hz, 2H), 1.92-1.85 (m, 1H), 1.49-1.36 (m, 3H), 1.19-1.02 (m, 3H).

Example 31

Preparation of Triacid 33 of Table A

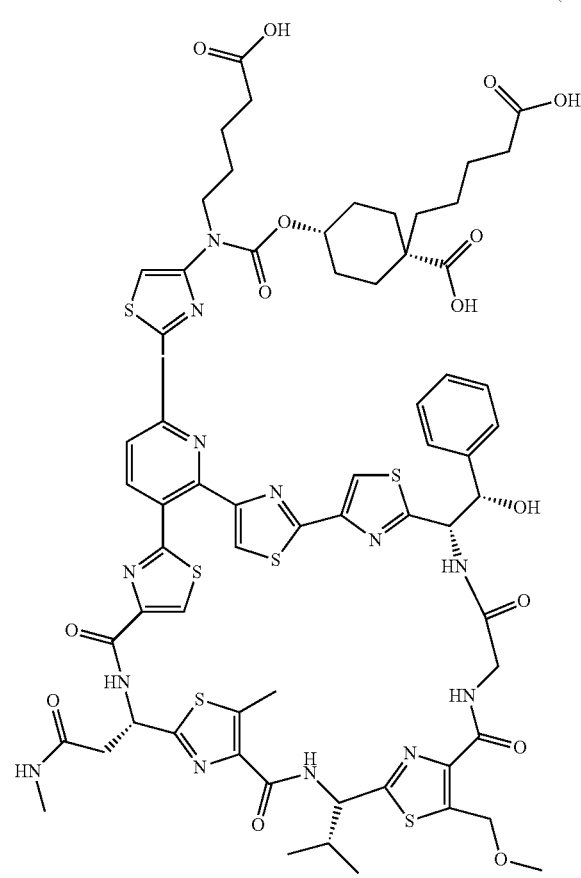

Compound 33 is prepared according to the procedures described in example 23, using the following deprotection conditions (MgI$_2$).

To the suspension of the triester (24 mg, 0.016 mmol) in toluene is added magnesium iodide (27 mg, 0.095 mmol) and the reaction mixture is heated to 100° C. for 12 h. The reaction mixture is concentrated and re-dissolved in DMF and filtered, purified by HPLC (40 to 80% CAN in water, 01% TFA). The fractions are collected and lyophilized to afford 33 (1.3 mg). LC/MS: m/z [M+2H]$^+$1467, R$_t$=1.05 min (method 6). $^1$H NMR (400 MHz, DMSO-d6) δ ppm 9.10 (d, 2H), 8.54 (t, 2H), 8.52 (s, 3H), 8.49 (m, 1H), 8.47 (d, 1H), 8.25 (s, 1H), 8.2 (d. 1H), 7.75 (s, 1H), 7.4-7.2 (m, 7H), 6.05 (s, 1H), 5.35-5.15 (m, 3H), 4.9 (m, 3H), 4.65 (s, 1H), 4.25 (m, 1H), 3.9 (s, 1H), 3.8 (d, 1H), 3.35 (s, 3H), 2.65 (m, 1H), 2.6 (s, 3H), 2.35-1.75 (m, 10H), 1.70-1.10 (m, 16H), 0.85 (m, 6H).

Example 32

Preparation of Triacid 34 of Table A

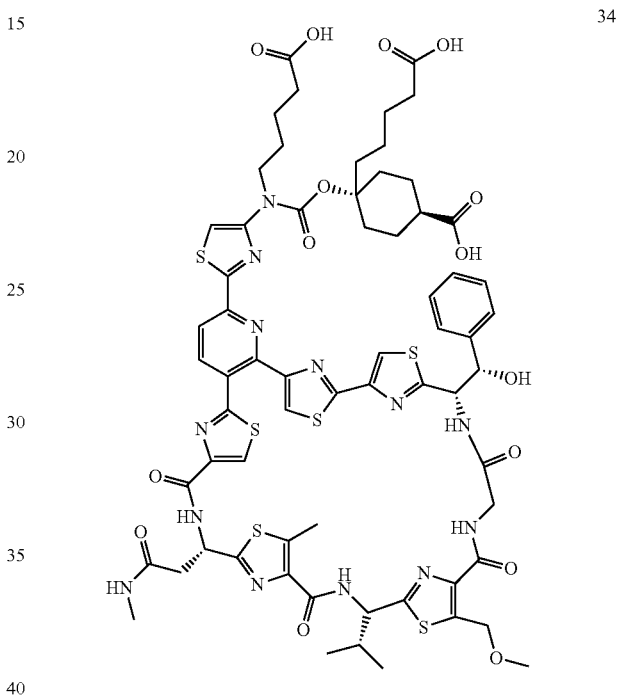

Compound 34 is prepared according to the procedures described in example 2, using the alcohol prepared in scheme 14. LC/MS: m/z [M+H]$^+$1467, R$_t$=1.45 min (method 6).

Scheme 14:

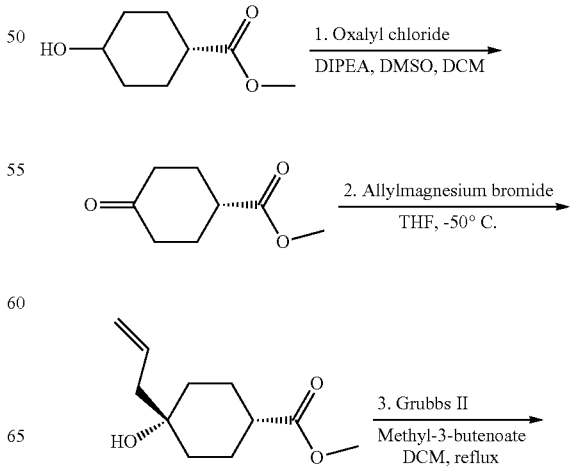

-continued

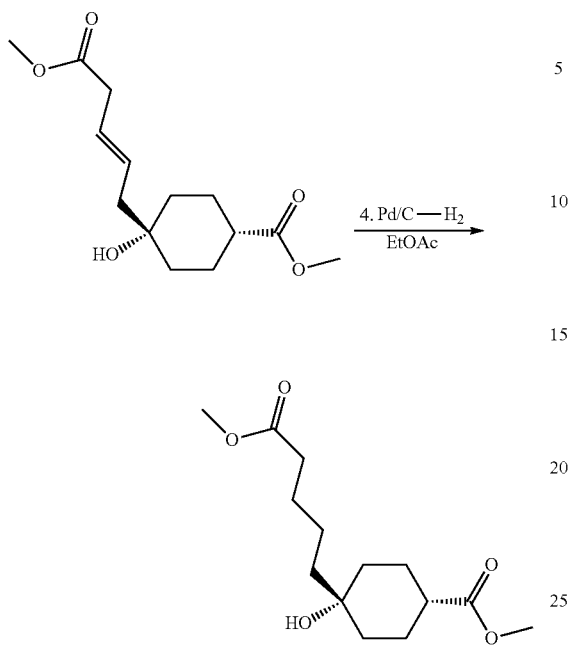

Step 1:

To a solution of oxalyl chloride in DCM (120 mL) at −70° C. is added DMSO (5.60 mL, 79 mmol). Then to the mixture, a solution of the alcohol (5.0 g, 31.6 mmol) in DCM (940 mL) is added dropwise within 2 min. The mixture is stirred for 15 min. at −70° C. After addition of i-Pr$_2$EtN, the mixture is allowed to reach room temperature and poured in to water (300 mL). The aqueous phase is extracted with DCM (30 mL). The combined extracts are dried over Na$_2$SO$_4$, filtered, concentrated and then purified by flash chromatography (eluent: EtOAc/heptane, gradient) to afford the ketone (2.8 g). $^1$H NMR (400 MHz, CDCl$_3$) δ 3.80 (s, 3H), 2.84 (m, 1H), 2.53 (m, 2H), 2.45 (m, 2H), 2.31 (m, 2H), 2.15 (m, 2H).

Step 2:

A solution of the ketone (500 mg, 3.20 mmol) in THF (20 mL) is cooled to −50° C. and allyl magnesium bromide (3.2 mL, 3.20 mmol) is added and the reaction stirred for 30 min. To the reaction mixture is added sat. aq NH$_4$Cl and the product is extracted with ethyl acetate, dried over Na$_2$SO$_4$, and purified by flash chromatography (eluent: EtOAc/heptane, gradient) to afford the alcohol (150 mg). $^1$H NMR (400 MHz, CDCl$_3$) δ 5.89 (m, 1H), 5.19 (m, 2H), 3.70 (s, 3H), 2.47 (m, 1H), 2.29 (d, 2H), 1.74 (m, 3H), 1.51-1.40 (m, 3H).

Step 3:

The diester is synthesized according to the procedure described in example 27. Obtained 122 mg, $^1$H NMR (400 MHz, CDCl$_3$) δ 5.67 (m, 2H), 3.71 (s, 3H), 3.17 (d, 2H), 2.30 (m, 1H), 2.29 (d, 2H), 1.91 (m, 2H), 1.69 (m, 3H), 1.47 (m, 2H).

Step 4:

The saturated diester-alcohol is synthesized according to the procedure described in example 27. Obtained 120 mg: $^1$H NMR (400 MHz, CDCl$_3$) δ 3.61 (s, 6H), 2.35 (m, 1H), 2.25 (m, 4H), 1.8 (m, 2H), 1.80-1.10 (m, 10H).

Example 33

Preparation of Diacid 35 of Table A

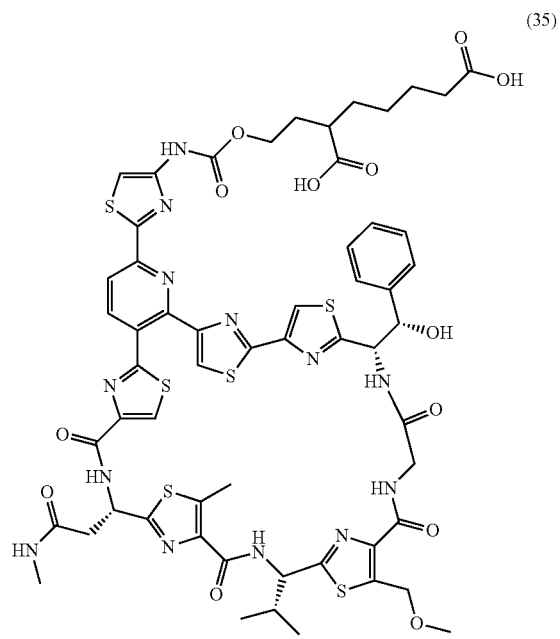

Compound 35 is prepared according to the procedures described in example 2, using the alcohol prepared in scheme 11. LC/MS: m/z [M+H]$^+$1326, R$_t$=1.04 min (method 6).

Example 34

Preparation of Diacid 2 of Table A

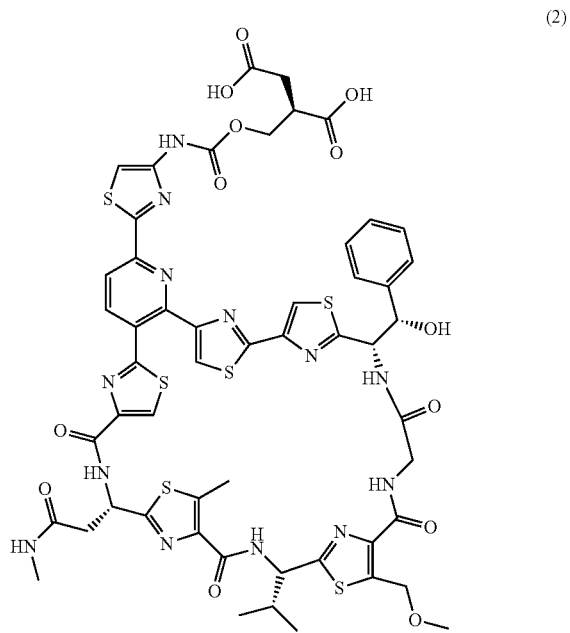

Scheme 15:
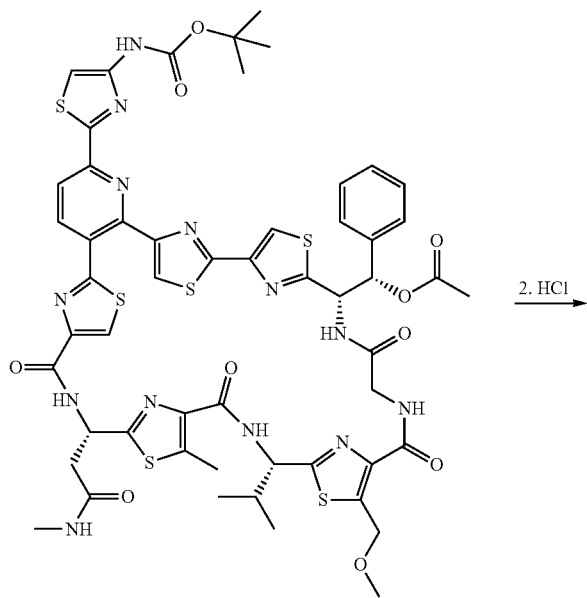
2. HCl →
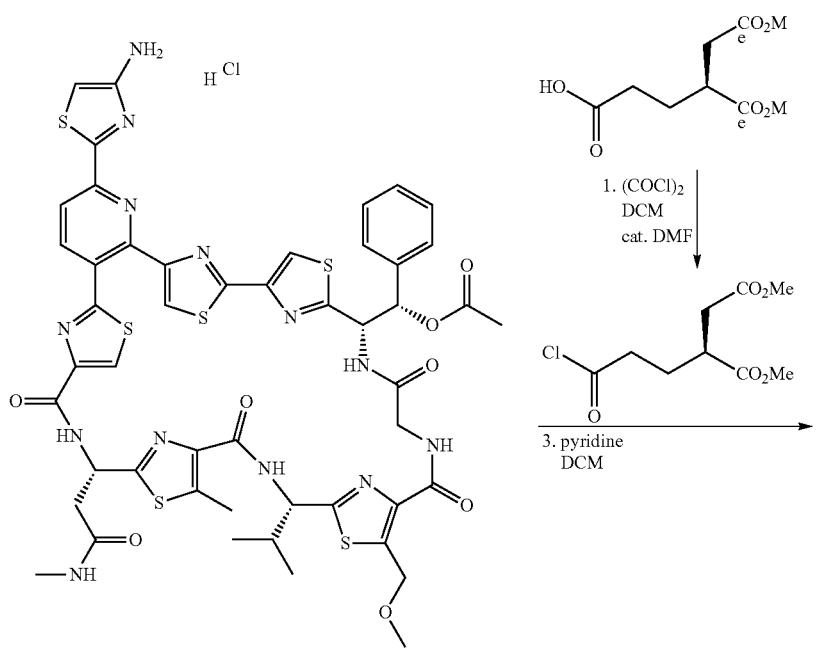
3. pyridine
DCM →

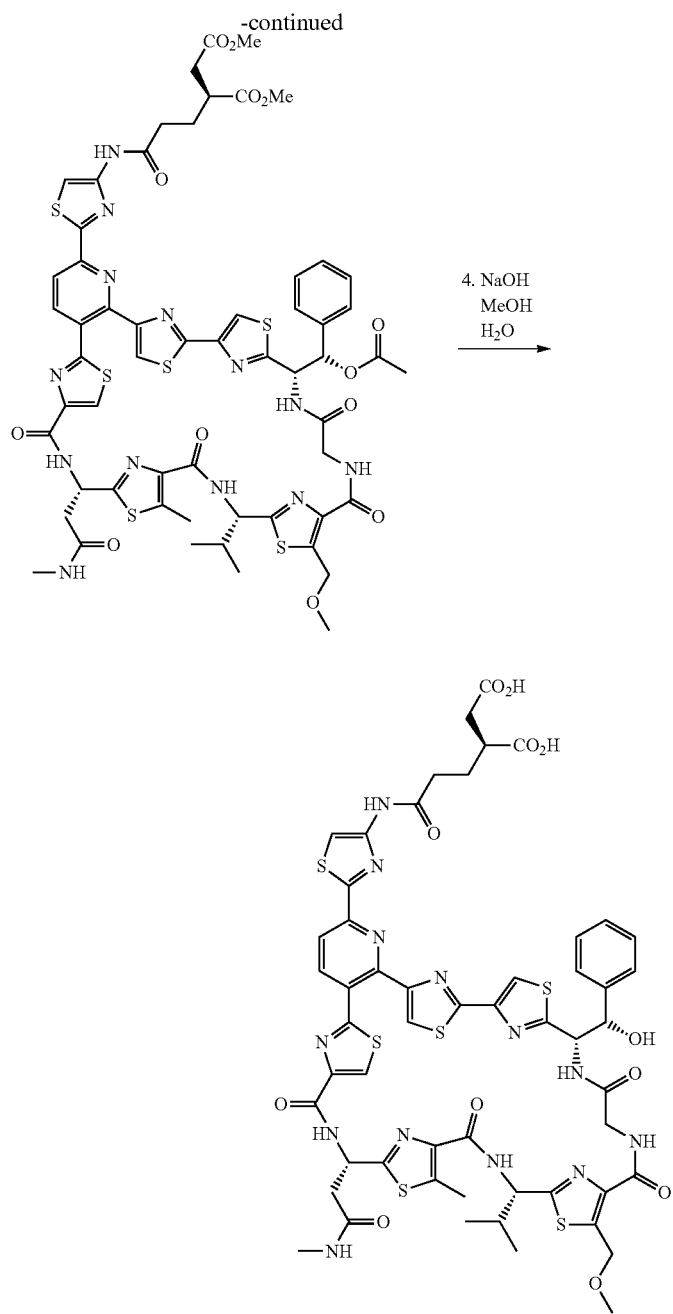

Step 1:

To a solution of the diester-acid (1 g, 4.6 mmol) in DCM (20 mL) is added oxalyl chloride (1.9 mL, 22.2 mmol), followed by 20 μL of DMF. The reaction is stirred for 90 min at 22° C. Reaction proceeds to a clear solution after 60 min. Volatiles are removed by concentration with DCM to afford 1.08 g (4.6 mmol, quant.) of a pale yellow solid that is used without further handling.

Step 2:

Hydrochloric acid is bubbled through a solution of acetate protected boc-amine (as prepared in example 8, scheme 4; 1.4 g, 1.1 mmol) in DCM (20 mL) for thirty min. The reaction mixture is then tightly capped and stirred for thirty minutes after which the reaction mixture is sparged with nitrogen. The mixture loses its gel like appearance. DCM (5 mL) is added to the solution, and HCl gas is bubbled through it for an additional 20 min, followed by nitrogen for 30 min. Crude product (1.32 g) is obtained after concentration as a bright orange solid, and taken on to the next step with no further purification. LC/MS: m/z [M+H]$^+$1138, R$_f$=1.5 min (method 1).

Step 3:

To a solution of the amine (1.24 g, 1.1 mmol) in DCM (120 mL), is added pyridine (445 μL, 5.5 mmol), followed by the acid chloride (0.510 g, 2.2 mmol). The reaction is stirred at 22° C. for 20 minutes. Subsequently, SiO$_2$ is added, and the resulting mix is concentrated to afford a slurry. Purification using flash column chromatography (elution with 500 mL of 50% EtOAc/heptane, 500 mL 75% EtOAc/ heptane, to 1 L 100% EtOAc) affords 1.29 g (0.97 mmol, 88% yield) of a pale yellow solid that is used without further modification.

Step 4:

To a solution of the diester (0.42 g, 0.31 mmol) in MeOH (30 mL) and $H_2O$ (10 mL) is added NaOH crystals (53 mg, 1.3 mmol) and this mixture is stirred at 22° C. for 24 hrs. The mixture is then concentrated to dryness. HPLC purification (30-100% $ACN/H_2O$ in 0.1% TFA, 10 min) then lypholization affords 300 mg (0.24 mmol, 77%) as a pale yellow solid, LC: $R_t$=10.24 min. $^1$H NMR (DMSO-d6, 400 MHz) δ (ppm) 11.15 (s, 2H), 9.12 (s, 1H), 8.69 (d, 1H), 8.68 (d, 1H), 8.65 (d, 1H), 8.59 (s, 1H), 8.43 (d, 1H), 8.37 (d, 1H), 8.25 (s, 1H), 8.16 (d, 1H), 7.82 (s, 1H), 7.46 (s, 1H), 7.37 (s, 1H), 7.32 (d, 1H), 7.29 (t, 1H), 7.24 (t, 1H), 6.36 (s, 1H), 5.30 (m, 1H), 5.24 (t, 1H), 5.21 (dd, 1H), 5.01 (d, 1H), 4.98 (s, 2H), 4.28 (dd, 1H), 3.80 (dd, 1H), 3.39 (s, 3H), 2.78 (m, 1H), 2.71 (m, 2H), 2.70 (m, 1H), 2.59 (s, 3H), 2.49 (d, 3H), 2.45 (m, 1H), 2.32 (m, 2H), 2.17 (m, 1H), 1.95 (m, 1H), 1.64 (m, 1H), 1.37 (m, 1H), 0.88 (d, 3H), 0.86 (d, 3H). HRMS (ES+) for $C_{54}H_{53}N_{13}O_{12}S_6$: Calc: $[M+2H]^{2+}$634.6198. Found: 634.6197.

Example 35

Preparation of Diacid 1 of Table A

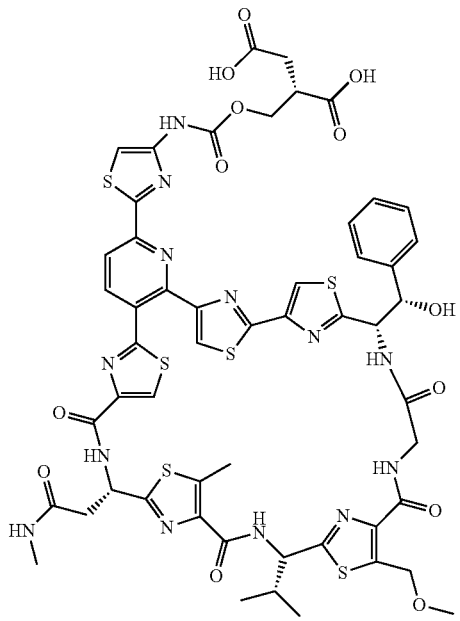

(1)

Compound 1 is prepared according to the procedures described in example 34. LC: $R_t$=10.05 min. $^1$H NMR (DMSO-d6, 400 MHz) δ (ppm) 13.5 (s, 2H), 9.24 (s, 1H), 8.73 (d, 1H), 8.68 (d, 1H), 8.65 (d, 1H), 8.59 (s, 1H), 8.43 (d, 1H), 8.37 (d, 1H), 8.23 (s, 1H), 8.16 (d, 1H), 7.77 (s, 1H), 7.46 (s, 1H), 7.37 (s, 1H), 7.32 (d, 1H), 7.29 (t, 1H), 7.24 (t, 1H), 6.36 (s, 1H), 5.30 (m, 1H), 5.25 (t, 1H), 5.21 (dd, 1H), 5.01 (d, 1H), 4.98 (s, 2H), 4.28 (dd, 1H), 3.81 (dd, 1H), 3.39 (s, 3H), 2.78 (m, 1H), 2.71 (m, 2H), 2.70 (m, 1H), 2.59 (s, 3H), 2.49 (d, 3H), 2.45 (m, 1H), 2.32 (m, 2H), 2.17 (m, 1H), 2.09 (m, 1H), 1.75 (m, 1H), 1.31 (m, 1H), 0.88 (d, 3H), 0.86 (d, 3H). HRMS (ES+) for $C_{54}H_{53}N_{13}O_{12}S_6$: Calc: $[M+2H]^{2+}$=634.6198. Found: 634.6197.

Biological Results:

Using the standard MIC test described above with the bacteria *Enterococcus faecalis*, *Enterococcus faecium* or *Staphylococcus aureus*, compounds 1-35 demonstrate a minimum inhibitory concentration ranging from 0.0010 µg/mL to 128 µg/mL.

In vitro assay for inhibition of prokaryotic transcription-translation [as described in the following references: 1. Zubay, G. (1973) In vitro synthesis of protein in microbial systems. *Annu. Rev. Genet.* 7, 267.87. 2. Zubay, G. (1980) The isolation and properties of CAP, the catabolite gene activator. *Meth. Enzymol.* 65, 856.77]. Antibiotic and compound dilutions: stock solutions of compound to be assayed at 2 µM are 80 µM in 40% DMSO. Stock solutions of compounds to be assayed at 10 µM are 400 µM in 40% DMSO.

Assay setup and protocol for Promega *E. coli* S30 Extract System

TABLE 1

*E. coli* S30 Extract system master mix

| Component | Final volume (16 µl) |
| --- | --- |
| "Methionine minus" amino acid mix | 1.0 µl |
| "Cysteine minus" amino acid mix | 1.0 µl |
| S30 premix | 8.0 µl |
| S30 extract | 6.0 µl |

TABLE 2

*E. coli* S30 Extract system assay components

| Components/Reagents | Final volume (20 µl total volume) |
| --- | --- |
| Template (pBESTluc ™) 286 ng/µl | 3.5 µl |
| Compound (40x final concentration) in 40% DMSO | 0.5 µl |
| Master mix (see table 1) | 16 µl |

The assay is performed as follows: pipet 3.5 µl of 286 ng/µl template DNA (pBESTluc™) into assay wells. Negative control wells receive $sdH_2O$ only. Transfer 0.5 µl of 40× compound stock solution to assay wells. Positive control wells (no compound) receive 0.5 µl 40% DMSO $sdH_2O$. Pipet 16 µl of master mix into assay wells. Incubate plate for two hours at 37° C. Rapidly chill the assay plate on ice for five minutes to stop the reaction. Add an equal volume (20 µl) of room temperature Steady-Glo® Luciferase assay reagent to all assay wells. Incubate 20 minutes and read light emitted with luminometer. Results are reported as % inhibition a 2 µM or 10 µM.

TABLE 2

| (1) | % inh. @ 2 uM = 65.4 | (2) | % inh. @ 2 uM = 72.8 | (3) | % inh. @ 2 uM = 67.8 |
| --- | --- | --- | --- | --- | --- |
| (4) | % inh. @ 2 uM = 85.3 | (5) | % inh. @ 2 uM = 78.5 | (6) | % inh. @ 2 uM = 86.8 |
| (7) | % inh. @ 2 uM = 86.0 | (8) | % inh. @ 2 uM = 59.7 | (9) | % inh. @ 2 uM = 67.1 |
| (10) | % inh. @ 2 uM = 2.0 | (11) | % inh. @ 2 uM = 92.3 | (12) | % inh. @ 2 uM = 82.4 |
| (13) | % inh. @ 2 uM = 74.9 | (14) | % inh. @ 2 uM = 55.5 | (15) | % inh. @ 2 uM = 64.5\ |
| (16) | % inh. @ 2 uM = 64.3 | (17) | % inh. @ 2 uM = 63.9 | (18) | % inh. @ 2 uM = 52.7 |
| (19) | % inh. @ 2 uM = 76.4 | (20) | % inh. @ 2 uM = 80.6 | (21) | % inh. @ 2 uM = 37.4 |
| (22) | % inh. @ 2 uM = 79.8 | (23) | % inh. @ 2 uM = 79.8 | (24) | % inh. @ 2 uM = 70.3 |

TABLE 2-continued

| | | | | | |
|---|---|---|---|---|---|
| (25) | % inh. @ 2 uM = 83.7 | (26) | % inh. @ 2 uM = 68.2 | (27) | % inh. @ 2 uM = 81.9 |
| (28) | % inh. @ 2 uM = 77.0 | (29) | % inh. @ 2 uM = 79.6 | (30) | % inh. @ 2 uM = 83.93 |
| (31) | % inh. @ 2 uM = 79.4 | (32) | % inh. @ 2 uM = 78.0 | (33) | % inh. @ 2 uM = 46.8 |
| (34) | % inh. @ 2 uM = 63.1 | (35) | % inh. @ 2 uM = 87.0 | | |

EQUIVALENTS

Those skilled in the art will recognize, or be able to ascertain using no more than routine experimentation, many equivalents to the specific embodiments and methods described herein. Such equivalents are intended to be encompassed by the scope of the following claims.

What is claimed is:

1. A compound of the formula I:

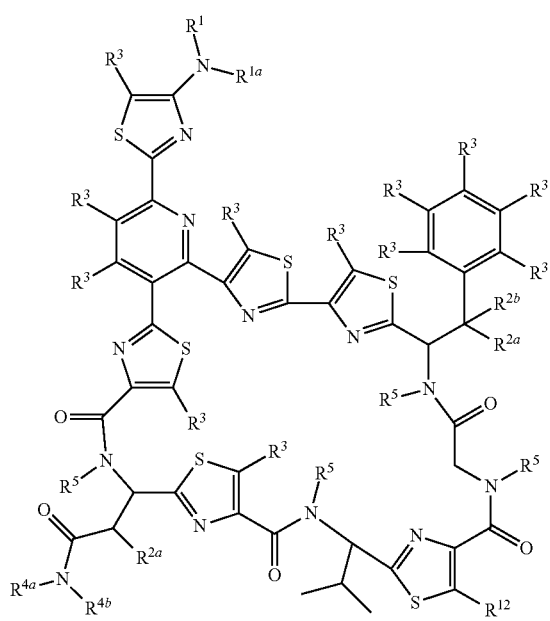

I or a pharmaceutically acceptable salt thereof, including the pyridine N-oxide thereof,
wherein:

$R^1$ and $R^{1a}$, taken in combination, form a saturated, partially unsaturated or aromatic heterocycle having 4 to 7 ring atoms and having 0-3 additional ring heteroatoms selected from N, O and S, wherein the heterocycle is substituted by at least two residues independently selected from $CO_2H$, —Z—$CO_2H$, and -A-Z—$CO_2H$;

A is independently selected at each occurrence from the group consisting of a —C(O)—, —C(O)O—, —C(O)N($R^{8a}$)—, —S(O)$_2$—, —S(O)—, —C(H)=N—, —S(O)$_2$N($R^{8a}$)—, and —S(O)N($R^{8a}$)—;

Z is $C_1$-$C_{10}$alkylene, $C_3$-$C_8$cycloalkylene, $C_3$-$C_8$heterocycloalkylene, phenylene, or 5-6 membered heteroarylene, each of which is optionally substituted with one or more groups independently selected from $C_1$-$C_4$alkyl, $C_1$-$C_4$alkoxy, hydroxy, amino, mono- and di-$C_1$-$C_6$alkylamino, C(O)OH, or halogen;

$R^{2a}$ is selected from the group consisting of H, substituted or unsubstituted alkyl, OH, $OR^{4a}$, $OC(O)R^{4a}$, $OC(O)N(R^{8a})_2$ and $N(R^{8a})_2$;

$R^{2b}$ is selected from the group consisting of absent, H and alkyl, or $R^{2a}$ and $R^{2b}$ may together form =O or =NH;

$R^3$ and $R^{12}$ are each, independently, selected from the group consisting of H, halogen, $OR^{4b}$, -A-J, and $N(R^{8a})_2$;

$R^{4a}$ is selected from the group consisting of H, and alkyl;

$R^{4b}$ is selected from the group consisting of alkyl and —($CH_2$—$CH_2$—O—)$_n$—$R^9$, wherein n is an integer of 1-500, 1,000, 2,000, 3,000, 4,000, 5,000, 10,000, 20,000, 30,000, 40,000, 50,000, or 60,000 or is a mean of a plurality of integers having a value of 1-500, 1,000, 2,000, 3,000, 4,000, 5,000, 10,000, 20,000, 30,000, 40,000, 50,000, or 60,000;

$R^5$ is selected from the group consisting of H, alkyl, and $R^{4b}$;

J is selected from the group consisting of H, F, O-alkyl, $N(R^{8a})_2$, $N^+(R^{8a})_3$, $N(R^{8a})C(O)$alkyl, $CO_2H$, C(=O)$N(R^{8a})_2$, $CO_2$-alkyl, $P(O)(OH)_2$, $P(O)(O$-alkyl$)_2$, and a substituted nitrogen-containing heterocycle;

$R^{8a}$ is absent, or selected from the group consisting of H, -(alkyl)-, -(cycloalkyl)-, C(alkyl)$_2$-J, —$R^{4b}$, wherein $R^{8a}$ can also cyclize with the atom to which $R^{8a}$ is bonded to form a 3, 4, 5, 6 or 7-membered ring that is aromatic or non-aromatic and may contain one or more heteroatoms, wherein the ring may be further substituted one or more times with substituents that are the same or different; and $R^9$ is selected from the group consisting of H, alkyl and $CH_2CO_2H$.

2. The compound of claim 1, wherein $R^{2b}$, $R^{4b}$ and $R^5$ are H, and $R^{4a}$ is $CH_3$.

3. The compound of claim 1, wherein $R^{2b}$, $R^{4b}$ and $R^5$ are H, $R^{4a}$ is $CH_3$, and $R^{12}$ is $CH_2$—O—$CH_3$.

4. The compound of claim 1, wherein formula I is represented by a compound of formula II:

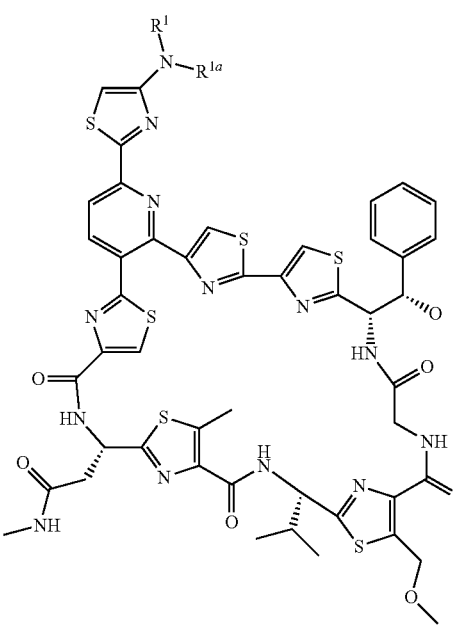

II or a pharmaceutically acceptable salt thereof.

5. The compound of claim 1, wherein formula I is represented by a compound of formula V:

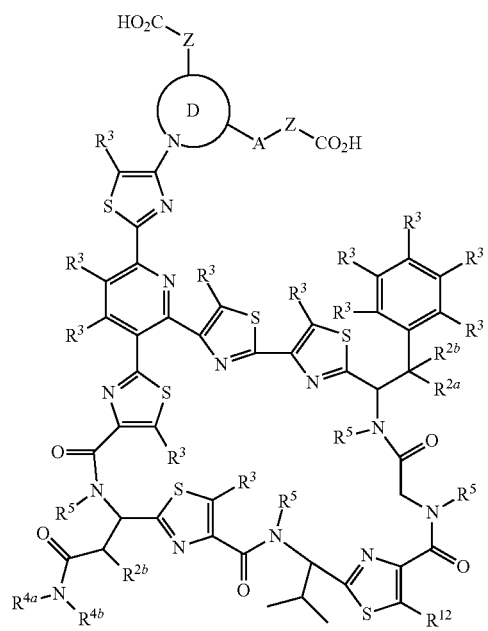

V or a pharmaceutically acceptable salt thereof, wherein
D represents a five or six membered heterocyclic ring which is saturated or aromatic, which ring comprises 0-2 additional ring heteroatoms selected from N, O or S.

6. The compound of claim 5, wherein $R^{2b}$, $R^{4b}$ and $R^5$ are H, and $R^{4a}$ is $CH_3$.

7. The compound of claim 5, wherein $R^{2b}$, $R^{4b}$ and $R^5$ are H, $R^{4a}$ is $CH_3$, and $R^{12}$ is $CH_2$—O—$CH_3$.

8. The compound of claim 5, wherein formula V is represented by a compound of formula VI:

VI

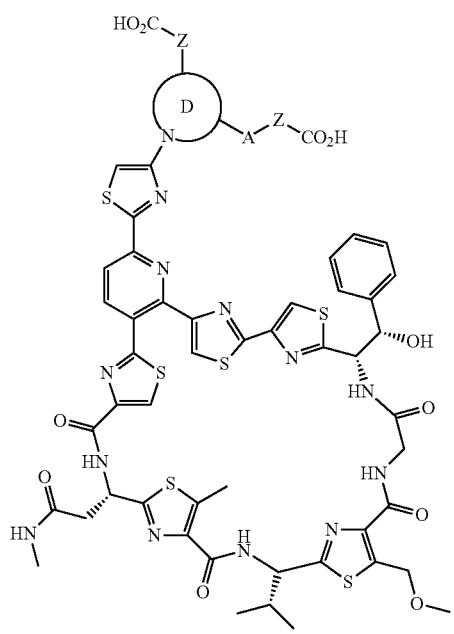

or a pharmaceutically acceptable salt thereof.

9. The compound of claim 8, wherein
A is selected from the group consisting of —C(O)O—, C(O)—NH—, —C(O)—, —S(O)$_2$—, and —S(O)$_2$NH—; and
Z is independently selected at each occurrence from the group consisting of $C_1$-$C_{10}$alkylene,

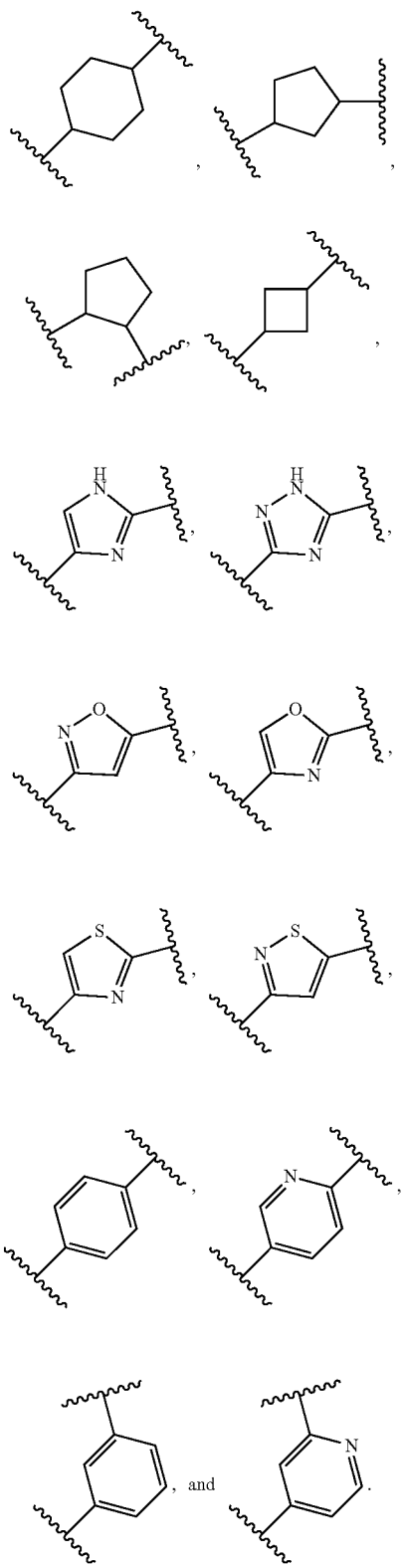

, and

10. The compound of claim 1, wherein $R^{2a}$ is OH or OAc.
11. The compound of claim 1, wherein the core pyridine functionality is of the following N-oxide formula:
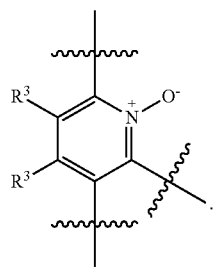
12. A compound selected from the group consisting of:
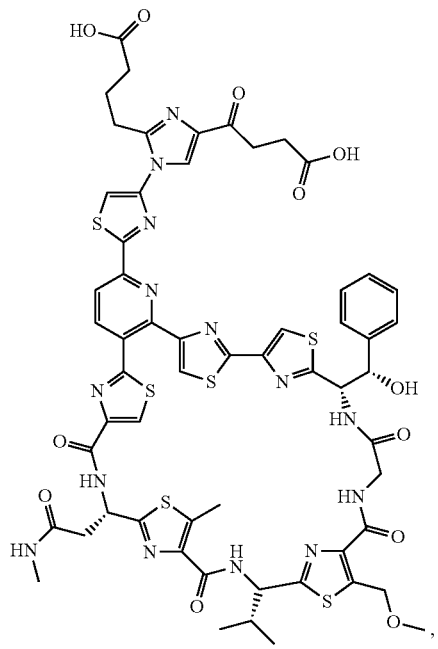
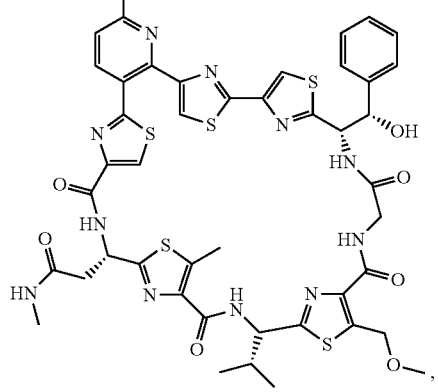
-continued
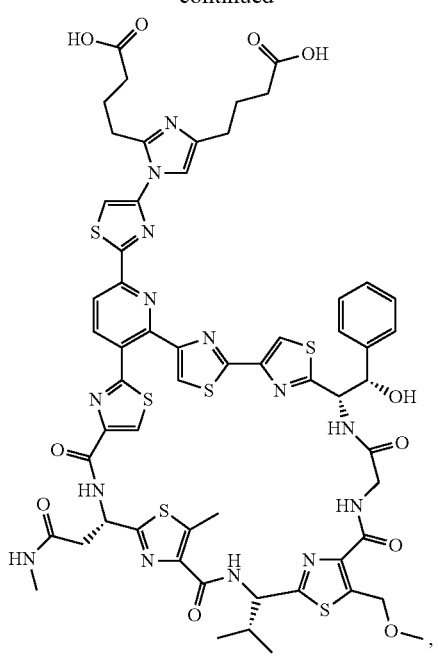
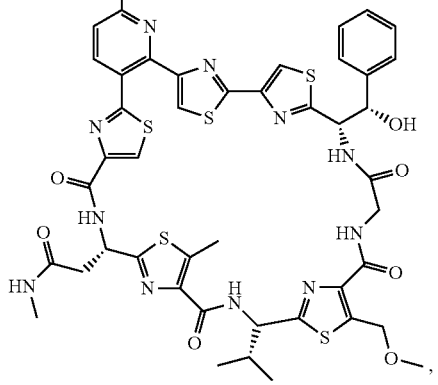

-continued

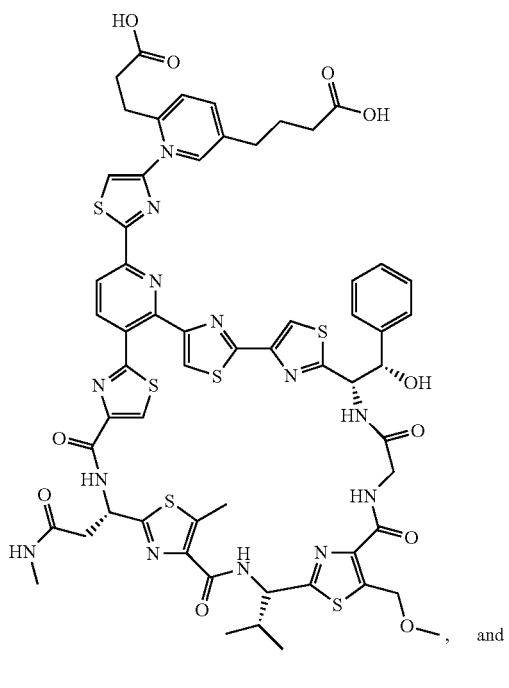

and

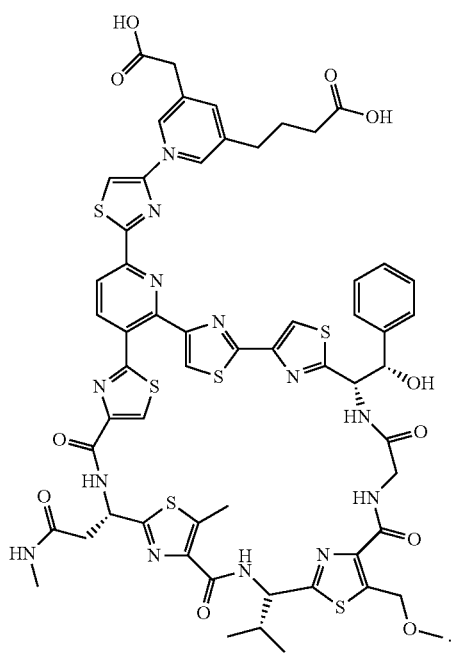

13. A compound of formula VII:

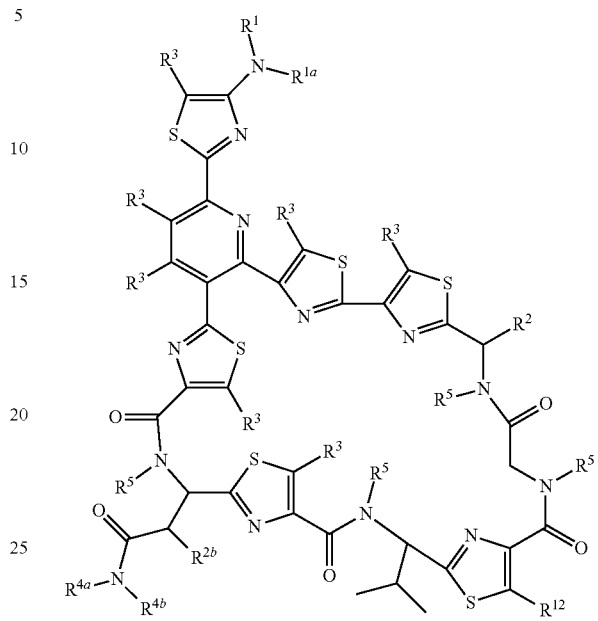

VII or a pharmaceutically acceptable salt thereof, including the pyridine N-oxide thereof;
wherein
$R^1$ and $R^{1a}$, taken in combination, form a saturated, partially unsaturated or aromatic heterocycle having 4 to 7 ring atoms and having 0-3 additional ring heteroatoms selected from N, O and S, wherein the heterocycle is substituted by at least two residues independently selected from $CO_2H$, —Z—$CO_2H$, and -A-Z—$CO_2H$;
A is independently selected at each occurrence from the group consisting of a —C(O)—, —C(O)O—, —C(O)N($R^{8a}$)—, —S(O)$_2$—, —S(O)—, —C(H)=N—, —S(O)$_2$N($R^{8a}$)—, and —S(O)N($R^{8a}$)—;
Z is $C_1$-$C_{10}$alkylene, $C_3$-$C_8$cycloalkylene, $C_3$-$C_8$heterocycloalkylene, phenylene, or 5-6 membered heteroarylene, each of which is optionally substituted with one or more groups independently selected from $C_1$-$C_4$alkyl, $C_1$-$C_4$alkoxy, hydroxy, amino, mono- and di-$C_1$-$C_6$alkylamino, C(O)OH, or halogen;
$R^2$ is hydrogen, $C_{1-6}$alkyl, hydroxy$C_{1-6}$alkyl, $C_{1-6}$alkoxy$C_{0-6}$alkyl, $C_{3-7}$cycloalkyl$C_{0-4}$alkyl, aryl$C_{0-4}$alkyl, or a residue of the formula:

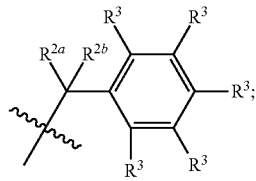

$R^{2a}$ is selected from the group consisting of H, substituted or unsubstituted alkyl, OH, $OR^{4a}$, $OC(O)R^{4a}$, $OC(O)N(R^{8a})_2$ and $N(R^{8a})_2$;
$R^{2b}$ is selected from the group consisting of absent, H and alkyl, or $R^{2a}$ and $R^{2b}$ may together form =O or =NH;

$R^3$ and $R^{12}$ are each, independently, selected from the group consisting of H, halogen, $OR^{4b}$, -A-J, and $N(R^{8a})_2$;

$R^{4a}$ is selected from the group consisting of H, and alkyl;

$R^{4b}$ is selected from the group consisting of alkyl and —$(CH_2$—$CH_2$—O—$)_n$—$R^9$, wherein n is an integer of 1-500, 1,000, 2,000, 3,000, 4,000, 5,000, 10,000, 20,000, 30,000, 40,000, 50,000, or 60,000 or is a mean of a plurality of integers having a value of 1-500, 1,000, 2,000, 3,000, 4,000, 5,000, 10,000, 20,000, 30,000, 40,000, 50,000, or 60,000;

$R^5$ is selected from the group consisting of H, alkyl, and $R^{4b}$;

J is selected from the group consisting of H, F, O-alkyl, $N(R^{8a})_2$, $N^+(R^{8a})_3$, $N(R^{8a})C(O)$alkyl, $CO_2H$, $C(=O)N(R^{8a})_2$, $CO_2$-alkyl, $P(O)(OH)_2$, $P(O)(O$-alkyl$)_2$, and a substituted nitrogen-containing heterocycle;

$R^{8a}$ is absent, or selected from the group consisting of H, -(alkyl)-, -(cycloalkyl)-, $C(alkyl)_2$-J, —$R^{4b}$, wherein $R^{8a}$ can also cyclize with the atom to which $R^{8a}$ is bonded to form a 3, 4, 5, 6 or 7-membered ring that is aromatic or non-aromatic and may contain one or more heteroatoms, wherein the ring may be further substituted one or more times with substituents that are the same or different; and $R^9$ is selected from the group consisting of H, alkyl and $CH_2CO_2H$.

14. A pharmaceutical composition comprising a compound of claim 1, and at least one pharmaceutically acceptable carrier or diluent.

* * * * *